(12) United States Patent
Baldwin et al.

(10) Patent No.: US 6,864,080 B2
(45) Date of Patent: Mar. 8, 2005

(54) **CRYSTALLIZATION AND STRUCTURE OF *STAPHYLOCOCCUS AUREUS* PEPTIDE DEFORMYLASE**

(75) Inventors: Eric T. Baldwin, Portage, MI (US); Melissa S. Harris, Marshall, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 89 days.

(21) Appl. No.: 09/896,580

(22) Filed: Jun. 29, 2001

(65) Prior Publication Data

US 2003/0170868 A1 Sep. 11, 2003

Related U.S. Application Data

(60) Provisional application No. 60/215,550, filed on Jun. 30, 2000, and provisional application No. 60/215,555, filed on Jun. 30, 2000.

(51) Int. Cl.$^7$ ................................................ C12N 9/80
(52) U.S. Cl. ..................................... 435/227; 435/228
(58) Field of Search ................................ 435/227, 228, 435/212; 536/23.2, 23.7

(56) References Cited

U.S. PATENT DOCUMENTS 6,410,688 B1 * 6/2002 Lonetto et al. ............. 530/350

FOREIGN PATENT DOCUMENTS

| EP | 0 786 519 A2 A3 | 7/1998 |
|---|---|---|
| EP | 0 879 879 A2 | 11/1998 |
| WO | WO 99/47639 | 9/1999 |
| WO | WO 99/47662 | 9/1999 |
| WO | WO 00/12678 | 3/2000 |
| WO | WO 01/16292 | 3/2000 |

OTHER PUBLICATIONS

Chen et al., "Actinonon, a naturally occurring antibacterial agent, is a potent deformylase inhibitor," *Biochemistry*. 2000;39(6):1256–62.

Greer, "Protein structure and function by comparative model building," *Ann N Y Acad Sci*. 1985;439:44–63.

Huntington et al., "Synthesis and antibacterial activity of peptide deformylase inhibitors," *Biochemistry*. 2000;39(15):4543–51.

Kuntz et al., "Structure–based Molecular Design," *Accounts of Chemical Research, US, American Chemical Society.* 1994;27:117–23.

Martin, "3D Database Searching in Drug Design," *Journal of Medicinal Chemistry*, 35(12):2145–2154 (1992).

Matthews, "Structural Basis of the Action of Thermolysin and Related Zinc Peptidases," *Accounts of Chemical Research*, 21:333–340 (1988).

Mazel et al., "Genetic characterization of polypeptide deformylase, a distinctive enzyme of eubacterial translation," *The EMBO Journal*, 13(4):914–923 (1994).

Meinnel et al., "The *Escherichia coli* fmt Gene, Encoding Methionyl–tRNA$_F$ $^{MET}$ Formyltransferase, Escapes Metabolic Control," *Journal of Bacteriology*, 175(4):993–1000 (1993).

Meinnel et al., "Enzymatic Properties of *Escherichia coli* Peptide Deformylase," *Journal of Bacteriology*, 177(7):1883–1887 (1995).

(List continued on next page.)

*Primary Examiner*—Nashaat T. Nashed
(74) *Attorney, Agent, or Firm*—Mueting, Raasch & Gebhardt, P.A.

(57) ABSTRACT

*Staphylococcus aureus* peptide deformylase has been crystallized, and the three-dimensional x-ray crystal structure has been solved to 1.9 Å resolution. The x-ray crystal structure is useful for solving the structure of other molecules or molecular complexes, and designing modifiers of peptide deformylase activity.

3 Claims, 17 Drawing Sheets

OTHER PUBLICATIONS

Meng et al., "Automated Docking with Grid–Based Energy Evaluation," *Journal of Computational Chemistry*, 13(4):505–524 (1992).

Merritt et al., "Raster3D Version 2.0. A Program for Photorealistic Molecular Graphics," *Acta Crystallographica*, D50(6):869–873 (1994).

Miranker et al., "Functionality Maps of Binding Sites: A Multiple Copy Simultaneous Search Method," *Proteins: Structure, Function, and Genetics*, 11(1):29–34 (1991).

Nishibata et al., "Automatic Creation of Drug Candidate Structures Based on Receptor Structure. Starting Point for Artificial Lead Generation," *Tetrahedron*, 47(43):8985–8990 (1991).

Rajagopalan et al., "Purification, Characterization, and Inhibition of Peptide Deformylase from *Escherichia coli*," *Biochemistry*, 36(45):13910–13918 (1997).

Rajagopalan et al., "Peptide Deformylase: A New Type of Mononuclear Iron Protein," *Journal of the American Chemical Society*, 119(50):12418–12419 (1997).

Rossmann, ed., *The Molecular Replacement Method A Collection of Papers on the Use of Non–Crystallographic Symmetry*, Gordon & Breach, Science Publishers, Inc., New York, Title page, publication page, and table of contents only, 6 pages (1972).

Sack, "CHAIN—A Crystallographic Modeling Program," *Journal of Molecular Graphics*, 6(4):224–225 (1988).

Schechter et al., "On the size of the active site in proteases. I. Papain," *Biochemical and Biophysical Research Communications*, 27(2):157–162 (1967).

Schmitt et al., "Molecular recognition governing the initiation of translation in *Escherichia coli*. A review," *Biochimie*, 78(7):543–544 (1996).

Schulman et al., "Anticodon loop size and sequence requirements for recognition of formylmethionine tRNA by methionyl–tRNA synthetase," *Proceedings of the National Academy of Sciences, USA*, 80(22):6755–6759 (1983).

Sheldrick et al., "Structure Solution by Iterative Peaklist Optimization of Tangent Expansion in Space Group P1," *Acta Crystallographica*, B51(4):423–431 (1995).

Solbiati et al., "Processing of the N Termini of Nascent Polypeptide Chains Requires Deformylation Prior to Methionine Removal," *Journal of Molecular Biology*, 290(3):607–614 (1999).

Tatusova et al., "BLAST 2 Sequences, a new tool for comparing protein and nucleotide sequences," *FEMS Microbiology Letters*, 174(2):247–250 (1999).

Travis, "Proteins and Organic Solvents Make an Eye–Opening Mix," *Science*, 262(5138):1374 (1993).

Van Duyne et al., "Atomic Structures of the Human Immunophilin FKBP–12 Complexes with FK506 and Rapamycin," *Journal of Molecular Biology*, 229(1):105–124 (1993).

Weiner et al., "An All Atom Force Field for Simulations of Proteins and Nucleic Acids," *Journal of Computational Chemistry*, 7(2):230–252 (1986).

Wyckoff et al., eds., "Diffraction Methods for Biological Macromolecules, Part A," *Methods in Enzymology*, vol. 114, Title page, publication page and table of contents only, 3 pages (1985).

Wycoff et al., eds., "Diffraction Methods for Biological Macromolecules, Part B," *Methods in Enzymology*, vol. 115, Title page, publication page and table of contents only, 3 pages (1985).

Hendrickson et al., "Stereochemically Restrained Crystallographic Least–Squares Refinement of Macromolecule Structures," in *Biomolecular Structure, Conformation, Function, and Evolution*, Srinivasan, ed., Pergamon Press Ltd., Oxford, UK, Title page, publication page and pp. 43–57 (1981).

Hirel et al., "Genetic engineering of methionyl–tRNA synthetase: in vitro regeneration of an active synthetase by proteolytic cleavage of a methionyl–tRNA synthetase–β–galactosidase chimeric protein," *Biochimie*, 70(6):773–782 (1988).

Hirel et al., "Extent of N–terminal methionine excision from *Escherichia coli* proteins is governed by the side–chain length of the penultimate amino acid," *Proceedings of the National Academy of Sciences, USA*, 86(21):8247–8251 (1989).

Jancarik et al., "Sparse matrix sampling: a screening method for crystallization of proteins," *Journal of Applied Crystallography*, 24(4):409–411 (1991).

Jongeneel et al., "A unique signature identifies a family of zinc–dependent metallopeptidases," *FEBS Letters*, 242(2):211–214 (1989).

Kozak, "Comparison of Initiation of Protein Synthesis in Procaryotes, Eucaryotes, and Organelles," *Microbiological Reviews*, 47(1):1–45 (1983).

Kraulis, "MOLSCRIPT: a program to produce both detailed and schematic plots of protein structures," *Journal of Applied Crystallography*, 24(5):946–950 (1991).

Kuntz et al., "A Geometric Approach to Macromolecule–Ligand Interactions," *Journal of Molecular Biology*, 161(2):269–288 (1982).

Laskowski et al., "PROCHECK: a program to check the stereochemical quality of protein structures," *Journal of Applied Crystallography*, 26(2):283–291 (1993).

Lattman, "Use of the Rotation and Translation Functions," *Methods in Enzymology*, 115:55–77 (1985).

Lauri et al., "CAVEAT: A program to facilitate the design of organic molecules," *Journal of Computer–Aided Molecular Design*, 8(1):51–66 (1994).

Livingston et al., "Deformylation and Protein Biosynthesis," *Biochemistry*, 8(1):435–443 (1969).

Makarova et al., "The Zn–peptidase Superfamily: Functional Convergence After Evolutionary Divergence," *Journal of Molecular Biology*, 292(1):11–17 (1999).

Blundell, "Metalloproteinase superfamilies and drug design," *Nature Structural Biology*, 1(2):73–75 (1994).

Böhm, "The computer program LUDI: A new method for the de novo design of enzyme inhibitors," *Journal of Computer–Aided Molecular Design*, 6(1):61–78 (1992).

Bünger, "Extension of Molecular Replacement: a New Search Strategy based on Patterson Correlation Refinement," *Acta Crystallographica*, A46:46–57 (1990).

Bünger, *X–PLOR Version 3.1: A System for X–ray Crystallography and NMR*, Yale University Press, New Haven, Title page, publication page and table of contents only, 13 pages (1992).

Chan et al., "Crystal Structure of the *Escherichia coli* Peptide Deformylase," *Biochemistry*, 36)45):13904–13909 (1997).

Collaborative Computational Project, No. 4, SERC Daresbury Laboratory, "The CPP4 Suite: Programs for Protein Crystallography," *ACTA Crystallographica*, D50(5):760–763 (1994).

Dalbøge et al., "In vivo processing of N–terminal methionine in *E. coli*," *FEBS Letters,* 266(1,2):1–3 (1990).

Eisen et al., "HOOK: A Program for Finding Novel Molecular Architectures That Satisfy the Chemical and Steric Requirements of a Macromolecule Binding Site," *Proteins: Structure, Function, and Genetics,* 19(3):199–221 (1994).

Finzel, "LORE: Exploiting Database of Known Structures," *Methods in Enzymology,* 277:230–242 (1997).

Gillet et al., "SPROUT: A program for structure generation," *Journal of Computer–Aided Molecular Design,* 7(2):127–153 (1993).

Goodford, "A Computational Procedure for Determining Energetically Favorable Binding Sites on Biologically Important Macromolecules," *Journal of Medicinal Chemistry,* 28(7):849–857 (1985).

Goodsell et al., "Automated Docking of Substrates to Proteins by Simulated Annealing," *Proteins: Structure, Function, and Genetics,* 8(3):195–202 (1990).

Hao et al., "Structural Basis for the Design of Antibiotics Targeting Peptide Deformylase," *Biochemistry,* 38(15):4712–4719 (1999).

Adams, "On the Release of the Formyl Group from Nascent Protein," *Journal of Molecular Biology,* 33(3):571–589 (1968).

Ball et al., "Cleavage of the N–terminal Formylmethionine Residue from a Bacteriophage Coat Protein in vitro" *Journal of Molecular Biology,* 79(3):531–537 (1973).

Bartlett et al., "CAVEAT: A Program to Facilitate the Structure–derived Design of Biologically Active Molecules," in *Molecular Recognition: Chemical and Biological Problems,* Special Publication No. 78, Roberts, ed., Royal Chemical Society, University of Exeter, Title page, publication page and pp. 182–196 (1989).

Benson et al., "An enzyme–substrate complex involved in bacterial cell wall biosynthesis," *Nature Structural Biology,* 2(8):644–653 (1995).

BLAST 2 Sequences. [online] National Center for Biotechnology Information, National Institutes of Health, United States, [retrieved Aug. 29, 2001]. Retrieved from the Internet: <URl:http://www.ncbi.nlm.gov/gorf/bl2.html>, 1 page.

Blundell et al., *Protein Crystallography,* Academic Press, New York, NY, Title page, publication page and table of contents only, 8 pages (1976).

Becker et al., "Structure of Peptide Deformylase and Identification of the Substrate Binding Site," *The Journal of Biological Chemistry,* 273(19):11413–11416 (1998).

Becker et al., "Iron center, substrate recognition and mechanism of peptide deformylase," *Nature Structural Biology,* 5(12):1053–1058 (1998).

Brizzard et al., "Immunoaffinity Purification of FLAG® Epitope–Tagged Bacterial Alkaline Phosphastase Using a Novel Monoclonal Antibody and Peptide Elution," *BioTechniques,* 16(4):730–735 (1994).

Chang et al., "Methionine Aminopeptidase Gene of *Escherichia coli* Is Essential for Cell Growth," *Journal of Bacteriology,* 171(7):4071–4072 (1989).

Chen et al., "Mechanistic Studies on the Aminopeptidase from *Aeromonas proteolytica:* A Two–Metal Ion Mechanism for Peptide Hydrolysis," *Biochemistry,* 36(14):4278–4286 (1997).

Chiang et al., "Expression and Purification of General Transcription Factors by FLAG Epitope–Tagging and Peptide Elution," *Peptide Research,* 6(2):62–64 (1993).

Dardel et al., "Solution Structure of Nickel–peptide Deformylase," *Journal of Molecular Biology,* 280)3):501–513 (1998).

Ford et al., "Fusion Tails for the Recovery and Purification of Recombinant Proteins," *Protein Expression and Purification,* 2:95–107 (1991).

Groche et al., "Isolation and Crystallization of Functionally Competent *Escherichia coli* Peptide Deformylase Forms Containing either Iron or Nickel in the Active Site," *Biochemical and Biophysical Research Communications,* 246(2):342–346 (1998).

Hopp et al., "A Short Polypeptide Marker Sequence Useful for Recombinant Protein Identification and Purification," *Biotechnology,* 6(10):1204–1210 (1988).

Hu et al., "H–Phosphonate Derivatives as Novel Peptide Deformylase Inhibitors," *Bioorganic & Medicinal Chemistry Letters,* 8:2479–2482 (1998).

Hu et al., "Determination of Substrate Specificity for Peptide Deformylase through the Screening of Combinatorial Peptide Library," *Biochemistry,* 38(2):643–650 (1999).

Laemmli, "Cleavage of Structural Proteins during the Assembly of the Head of Bacteriophage T4," *Nature,* 227(5259):680–685 (1970).

Lazennec et al., "Formate Dehydrogenase–Coupled Spectrophotometric Assay of Peptide Deformylase," *Analytical Biochemistry,* 244:180–182 (1997).

Meinnel et al., "Mapping of the Active Site Zinc Ligands of Peptide Deformylase," *Journal of Molecular Biology,* 254(2):175–183 (1995).

Miennel et al., "A New Subclass of the Zinc Metalloproteases Superfamily Revealed by the Solution Structure of Peptide Deformylase," *Journal of Molecular Biology,* 262(3):375–386 (1996).

Meinnel et al., "Structure–Function Relationships within the Peptide Deformylase Family. Evidence for a Conserved Architecture of the Active Site Involving Three Conserved Motifs and a Metal Ion," *Journal of Molecular Biology,* 267(3):749–761 (1997).

Meinnel et al., "Design and Synthesis of Substrate Analogue Inhibitors of Peptide Deformylase," *Biochemistry,* 38(14):4287–4295 (1999).

Prescott et al., "Aeromonas Aminopeptidase," *Methods in Enzymology,* 45(Part B):530–543 (1976).

QIAexpress®—The Complete System Ni–NTA Technology and the 6xHis Tag. Datasheet [online]. Qiagen [retrieved on Nov. 6, 2001]. Retrieved from the Internet: <URL:www-.qiagen.com/catalog/chapter_03/chap3.asp>, 3 pages.

QIAexpress® Expression System. Datasheet [online]. Qiagen [retrieved Nov. 6, 2001]. Retrieved from the Internet: <URL:www.qiagen.com/catalog/chapter_03/chap3.asp>, 5 pages.

QIAexpress® Protein Purification System. Datasheet [online]. Qiagen [retrieved on Nov. 6, 2001]. Retrieved from the Internet: <URL:www.qiagen.com/catalog/chapter_03/chap3.asp>, 5 pages.

Qiagen, *QIAexpress Detection and Assay Handbook,* pp. 9–45, 52–76 (1999).

Wei et al., "Continuous Spectrophotometric Assay of Peptide Deformylase," *Analytical Biochemistry,* 250:29–34 (1997).

\* cited by examiner

```
                       1                                                    50
SEQ ID NO:6 Pseudo pdf  ~~~~~~~~~~ ~~~~~~~~~~ ~~~~~~~~~~ ~~~~~~~~~M AIKKLVPASH
SEQ ID NO:2 E. coli pdf ~~~~~~~~~~ ~~~~~~~~~~ ~~~~~~~~~~ ~~~~~~~~~~ SVLQVLHIPD
SEQ ID NO:3 Haemop influ ~~~~~~~~~~ ~~~~~~~~~~ ~~~~~~~~~~ ~~~~~~~~~M TALNVLIYPD
SEQ ID NO:4 Bacillus sub ~~~~~~~~~~ ~~~~~~~~~~ ~~~~~~~~~~ ~~~~~~~~~M AVKKVVTHPA
SEQ ID NO:5 Mycopl pneu MTKILPVSTI SIFRIILILP QINMELLPTK AWLVLDDVKE INEPTKPVQF
SEQ ID NO:1 Active pdf  MYEYLNNLFT VIQ..LKQIK IRKVQYMLTM KDIIRDGHPT LRQKAAELEL 51                                                  100
            Pseudo pdf  PILTKKAQAV KTFDDSLKRL LQDLEDTMYA .QEAAGLCAP QINQSLQVAI
            E. coli pdf ERLRKVAKPV EEVNAEIQRI VDDMFETMYA .EEGIGLAAT QVDIHQRIIV
            Haemop influ DHLKVVCEPV TKVNDAIRKI VDDMFDTMYQ .EKGIGLAAP QVDILQRIIT
            Bacillus sub EVLETPAETV TVFDKKLKKL LDDMYDTMLE .MDGVGLAAP QIGILKRAAV
            Mycopl pneu PLDQASLDCI AKMMAYVDAS YNGD.AEKYG IIPGIGIAAN QIGYWKQM.F
            Active pdf  PLTKEEKETL IAMREFLVNS QDEEIAKRYG LRSGVGLAAP QINISKRM.I 101                                                 150
            Pseudo pdf  ....IDMEM. ...EGLLQLV N......PKI ISQSNETITD IEGSITLPDV
            E. coli pdf ....IDVSEN RDER..LVLI N......PEL LEKSGET.GI EEGCLSIPEQ
            Haemop influ ....IDVEGD KQNQ..FVLI N......PEI LASEGET.GI EEGCLSIPGF
            Bacillus sub ....VEIGDD R.GR..IDLV N......PEI LEKSGEQ.TG IEGCLSFPNV
            Mycopl pneu YIHLMD..GG VEHKCLLINP KIINLSANKS FLKSG..... .EGCLSVPKM
            Active pdf  AVLIPDDGSG KSYDYMLVNP KIVSHSVQEA YLPTG..... .EGCLSVDDN 151                                                 200
            Pseudo pdf  YG.EVTRSKM IVVESYD.VN GNKVELTAHE DVARMILHII DQMNGIPFTE
            E. coli pdf RA.LVPRAEK VKIRALD.RD GKPFELEADG LLAICIQHEM DHLVGKLFMD
            Haemop influ RA.LVPRKEK VTVRALD.RD GKEFTLDADG LLAICIQHEI DHLNGILFVD
            Bacillus sub YG.DVTRADY VKVRAFN.RQ GKPFILEARG FLARAVQHEM DHLDGVLFTS
            Mycopl pneu HQGYVIRHEW ITITGFDWLQ QKEITITATG LFGMCLQHEF DHLQGRFYYH
            Active pdf  VAGLVHRHNK ITIKAKD.IE GNDIQLRLKG YPAIVFQHEI DHLNGVMFYD 201                       235
            Pseudo pdf  RADRILTDKE VEAYFINDRS HHHHHH ~~ ~~~~~
            E. coli pdf YLSPLKQQRI RQKVEKLDRL KARA~~~~~~ ~~~~~
            Haemop influ YLSPLKRQRI KEKLIKYKKQ IAKS~~~~~~ ~~~~~
            Bacillus sub KISKYYTEDE LADMEG~~~~ ~~~~~~~~~~ ~~~~~
            Mycopl pneu RINPLNPLFT NKEWKVINPA LPSDSE~~~~ ~~~~~
            Active pdf  HIDKDHPLQP HTDAVEVHQH HHH~~~~~~~ ~~~~~
```

Fig. 3

SEQ ID NO:7 S.aureus    MLTMKDIIRDGHLRQKAAELELPLTEEKETLIMREFLVNSQDEEIAKRYG

SEQ ID NO:8 E.coli      SV           LRKVAKPVEEV    EIQRIVDMFETMY

S.aureus    GVGLAAPQINISKRMIAVLIPDDGSGKSYDLVNPKIVS SVQEAYLPTEGCL

E.coli      GIGLAATQVDIHQRIIVIDVSEN        LINPELLE S GETGI   EGCL

S.aureus    VDDNVALVHRHNRI IKAKDIEGNDIQLRLKGYPAIVFQHEIDHLNGVMFYDHI

E.coli      IPEQR LVPRAEKV IRALDRDGKPFELEADGLLAICIQHEMDHLVGKLFMDYL

S.aureus    DKDHPLQPHTDAVEVHHH

E.coli                                   SPLKQQRIRQKVEKLDRLK

CRYSTALLIZATION AND STRUCTURE OF *STAPHYLOCOCCUS AUREUS* PEPTIDE DEFORMYLASE

This application claims the benefit of the U.S. Provisional Application No. 60/215,550, filed Jun. 30, 2000, and U.S. Provisional Application No. 60/215,555, filed Jun. 30, 2000, both of which are incorporated herein by reference in their entireties,

FIELD OF THE INVENTION

The present invention is related to the crystallization and structure determination of *Staphylococcus aureus* peptide deformylase (*S. aureus* pdf).

BACKGROUND OF THE INVENTION

In all bacteria as well as mitochondria and chloroplasts the initiation of protein synthesis normally requires an N-formylated methionine residue. The special initiation tRNA, $tRNA_f^{Met}$, is charged with methionine by the Methionyl-tRNA synthetase (EC 6.1.10) which adds a methionine to either of the methionine tRNAs with the consumption of ATP. The formyl group is added to the charged $tRNA_f^{Met}$ from 10-formyltetraydrofolate which is catalyzed by methionine-$tRNA_f^{Met}$ formyl-transferase (EC 2.1.2.9). The formylated tRNA is transferred to the ribosome where protein synthesis is initiated (FIG. 1). All nascent polypeptides are synthesized with N-formyl methionine at the n-terminus.

Mature proteins do not by and large retain n-formyl methionine at the n-terminus. In fact, a rather heterogenous population of amino acids are normally found at the n-terminus of mature proteins—alanine, glycine, serine, threonine, or methionine. Larger amino acids are rarely found, which suggests that multiple catabolic processing might occur after or in concert with protein synthesis. All known amino-terminal peptidases cannot use formylated peptides as substrates. After translation, the formyl group is removed by Peptide Deformylase (pdf) as illustrated in FIG. 2. This metalloenzyme (EC 3.5.1.27) removes the formyl group from the peptide amino-terminus and releases the protein for possible further processing by methionine aminopeptidase (MAP; EC 3.4.11.18). The formylation/deformylation cycle is unique to eubacteria and does not occur in eucaryotic protein synthesis. The essential deformylation activity of pdf makes it an attractive target for crystallization and structural studies. Such studies may lead to the design of new antibiotics.

SUMMARY OF THE INVENTION

In one aspect, the present invention provides crystalline *S. aureus* peptide deformylase. Optionally, one or more methionine may be replaced with selenomethionine. The crystal may optionally include a coordinated metal ion selected from the group of metals consisting of Fe, Zn, Ni and combinations thereof.

In one embodiment, the crystal has the orthorhombic space group symmetry $C222_1$. Preferably, the unit cell has dimensions a, b, and c; wherein a is about 90 Å to about 100 Å, b is about 116 Å to about 128 Å, and c is about 45 Å to about 50 Å; and wherein $\alpha=\beta=\gamma=90°$. More preferably, a is about 92 Å to about 95 Å, b is about 121 Å to about 124 Å, and c is about 47 Å to about 49 Å.

In another embodiment, the present invention provides a crystal of *S. aureus* peptide deformylase having the monoclinic space group symmetry C2. Preferably, the unit cell has dimensions a, b, and c; wherein a is about 85 Å to about 100 Å, b is about 35 Å to about 50 Å, and c is about 90 Å to about 110 Å; and wherein $\alpha=\gamma=90°$ and $\beta$ is about 90° to about 95°. More preferably, a is about 91 Å to about 95 Å, b is about 41 Å to about 44 Å, and c is about 102 Å to about 105 Å.

In still another embodiment, the present invention provides a crystal of *S. aureus* peptide deformylase having the tetragonal space group symmetry $P4_1$ or $P4_22_12$. Preferably, the unit cell has dimensions a, b, and c; wherein a and b are about 130 Å to about 190 Å, and c is about 30 Å to about 70 Å; and wherein $\alpha=\beta=\gamma=90°$. More preferably, a and b are about 160 Å to about 164 Å, and c is about 45 Å to about 49 Å.

In another aspect, the present invention provides a method for crystallizing an *S. aureus* peptide deformylase molecule or molecular complex. In one embodiment the method includes preparing a stock solution of purified *S. aureus* peptide deformylase at a concentration of about 1 mg/ml to about 50 mg/ml; contacting the stock solution with a precipitating solution containing about 1% by weight to about 35% by weight PEG having a number average molecular weight between about 300 and about 20,000; about 0 M to about 0.2 M $MgCl_2$; and about 0% by weight to about 25% by weight DMSO; the precipitating solution being buffered to a pH of about 5 to about 9; and allowing *S. aureus* peptide deformylase to crystallize from the resulting solution. Preferably, the precipitating solution contains about 15% by weight to about 25% by weight PEG having a number average molecular weight between about 3000 and about 5,000; about 0.05 M to about 0.15 M $MgCl_2$ and is buffered to a pH of about 8 to about 9.

In another embodiment the method for crystallizing an *S. aureus* peptide deformylase molecule or molecular complex includes preparing a stock solution of purified *S. aureus* peptide deformylase at a concentration of about 1 mg/ml to about 50 mg/ml; contacting the stock solution with a precipitating solution containing about 1% by weight to about 40% by weight PEG having a number average molecular weight between about 300 and about 20,000; about 0.005 M to about 0.5 M citric acid; about 0% by weight to about 25% by weight DMSO; and sufficient base to adjust the pH of the precipitating solution to about 5.0 to about 6.5; and allowing *S. aureus* peptide deformylase to crystallize from the resulting solution. Preferably, the precipitating solution contains about 1% by weight to about 40% by weight PEG having a number average molecular weight between about 2000 and about 4,000; about 0.05 M to about 0.2 M citric acid, and sufficient base to adjust the pH of the precipitating solution to about 5.0 to about 5.5.

In still another embodiment the method for crystallizing an *S. aureus* peptide deformylase molecule or molecular complex includes preparing a stock solution of purified *S. aureus* peptide deformylase at a concentration of about 1 mg/ml to about 50 mg/ml; contacting the stock solution with a precipitating solution containing about 0.2 M to about 1.5 M sodium citrate; about 0.005 M to about 0.5 M Hepes; about 0% by weight to about 25% by weight DMSO; and sufficient base to adjust the pH of the precipitating solution to about 7.0 to about 8.5; and allowing *S. aureus* peptide deformylase to crystallize from the resulting solution. Preferably, the precipitating solution contains about 25% by weight to about 35% by weight PEG having a number average molecular weight between about 2000 and about 4,000; about 0.05 M to about 0.2 M citric acid, and sufficient base to adjust the pH of the precipitating solution to about 5.0 to about 5.5.

In still another embodiment the method for crystallizing an *S. aureus* peptide deformylase molecule or molecular complex includes preparing a stock solution of purified *S. aureus* peptide deformylase at a concentration of about 1 mg/ml to about 50 mg/ml; contacting the stock solution with a precipitating solution containing about 1% by weight to about 40% by weight PEG having a number average molecular weight between about 300 and about 20,000; about 0 M to about 0.4 M $MgCl_2$; and about 0% by weight to about 25% by weight DMSO; the precipitating solution being buffered to a pH of about 7 to about 9; and allowing *S. aureus* peptide deformylase to crystallize from the resulting solution. Preferably, the precipitating solution contains about 15% by weight to about 35% by weight PEG having a number average molecular weight between about 3,000 and about 5,000; about 0.05 M to about 0.3 M $MgCl_2$; and the precipitating solution being buffered to a pH of about 8 to about 9.

In another aspect, the present invention provides a molecule or molecular complex including at least a portion of an *S. aureus* peptide deformylase or an *S. aureus* peptide deformylase-like active site including amino acids Gly58, Gly60, Leu61, Gln65, Glu109, Gly110, Cys111, Leu112, Ile150, His154, Glu155, and His158, the active site being defined by a set of points having a root mean square deviation of less than about 0.35 Å from points representing the backbone atoms of said amino acids as represented by structure coordinates listed in Table 1. Optionally, the molecule or molecular complex further includes a coordinated metal ion selected from the group of metals consisting of Fe, Zn, Ni and combinations thereof. Preferably, the metal ion is coordinated by the amino acids Cys111, His154, and His158.

In another aspect, the present invention provides a scalable three-dimensional configuration of points, at least a portion of said points, and preferably all of said points, derived from structure coordinates of at least a portion of an *S. aureus* peptide deformylase molecule or molecular complex listed in Table 1 and having a root mean square deviation of less than about 1.4 Å from said structure coordinates. Preferably, at least a portion of the points are derived from the *S. aureus* peptide deformylase structure coordinates are derived from structure coordinates representing the locations of at least the backbone atoms of a plurality of the amino acids defining at least one *S. aureus* peptide deformylase or *S. aureus* peptide deformylase-like active site, the active site including amino acids Gly58, Gly60, Leu61, Gln65, Glu109, Gly110, Cys111, Leu112, Ile150, His154, Glu155, and His158.

In another aspect, the present invention provides a machine-readable data storage medium including a data storage material encoded with machine readable data which, when using a machine programmed with instructions for using said data, displays a graphical three-dimensional representation of at least one molecule or molecular complex selected from the group consisting of (i) a molecule or molecular complex including at least a portion of an *S. aureus* peptide deformylase or an *S. aureus* peptide deformylase-like active site including amino acids Gly58, Gly60, Leu61, Gln65, Glu109, Gly110, Cys111, Leu112, Ile150, His154, Glu155, and His158, the active site being defined by a set of points having a root mean square deviation of less than about 0.35 Å from points representing the backbone atoms of said amino acids as represented by structure coordinates listed in Table 1.

In another aspect, the present invention provides a computer-assisted method for obtaining structural information about a molecule or a molecular complex of unknown structure including: crystallizing the molecule or molecular complex; generating an x-ray diffraction pattern from the crystallized molecule or molecular complex; applying at least a portion of the structure coordinates set forth in Table 1 to the x-ray diffraction pattern to generate a three-dimensional electron density map of at least a portion of the molecule or molecular complex whose structure is unknown.

In another aspect, the present invention provides a computer-assisted method for homology modeling an *S. aureus* peptide deformylase homolog including: aligning the amino acid sequence of an *S. aureus* peptide deformylase homolog with the amino acid sequence of *S. aureus* peptide deformylase SEQ ID NO:12 and incorporating the sequence of the *S. aureus* peptide deformylase homolog into a model of *S. aureus* peptide deformylase derived from structure coordinates set forth in Table 1 to yield a preliminary model of the *S. aureus* peptide deformylase homolog; subjecting the preliminary model to energy minimization to yield an energy minimized model; remodeling regions of the energy minimized model where stereochemistry restraints are violated to yield a final model of the *S. aureus* peptide deformylase homolog.

In another aspect, the present invention provides a computer-assisted method for identifying a potential modifier of *S. aureus* peptide deformylase activity including: supplying a computer modeling application with a set of structure coordinates of a molecule or molecular complex, the molecule or molecular complex including at least a portion of at least one *S. aureus* peptide deformylase or *S. aureus* peptide deformylase-like active site, the active site including amino acids Gly58, Gly60, Leu61, Gln65, Glu109, Gly110, Cys111, Leu112, Ile150, His154, Glu155, and His158; supplying the computer modeling application with a set of structure coordinates of a chemical entity; and determining whether the chemical entity is expected to bind to the molecule or molecular complex, wherein binding to the molecule or molecular complex is indicative of potential modification of *S. aureus* peptide deformylase activity.

In another aspect, the present invention provides a computer-assisted method for designing a potential modifier of *S. aureus* peptide deformylase activity including: supplying a computer modeling application with a set of structure coordinates of a molecule or molecular complex, the molecule or molecular complex including at least a portion of at least one *S. aureus* peptide deformylase or *S. aureus* peptide deformylase-like active site, the active site including amino acids Gly58, Gly60, Leu61, Gln65, Glu109, Gly110, Cys111, Leu112, Ile150, His154, Glu155, and His158; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity; and determining whether the modified chemical entity is expected to bind to the molecule or molecular complex, wherein binding to the molecule or molecular complex is indicative of potential modification of *S. aureus* peptide deformylase activity.

In another aspect, the present invention provides a computer-assisted method for designing a potential modifier of *S. aureus* peptide deformylase activity de novo including: supplying a computer modeling application with a set of structure coordinates of a molecule or molecular complex, the molecule or molecular complex including at least a portion of at least one S. aureus peptide deformylase or S. aureus peptide deformylase-like active site, wherein the active site includes amino acids Gly58, Gly60, Leu61, Gln65, Glu109, Gly110, Cys111, Leu112, Ile150, His154, Glu155, and His158; forming a chemical entity represented by set of structure coordinates; and determining whether the chemical entity is expected to bind to the molecule or molecular complex, wherein binding to the molecule or molecular complex is indicative of potential modification of S. aureus peptide deformylase activity.

In another aspect, the present invention provides a method for making a potential modifier of S. aureus peptide deformylase activity, the method including chemically or enzymatically synthesizing a chemical entity to yield a potential modifier of S. aureus peptide deformylase activity, the chemical entity having been identified during a computer-assisted process including supplying a computer modeling application with a set of structure coordinates of a molecule or molecular complex, the molecule or molecular complex including at least a portion of a S. aureus peptide deformylase or S. aureus peptide deformylase-like active site; supplying the computer modeling application with a set of structure coordinates of a chemical entity; and determining whether the chemical entity is expected to bind to the molecule or molecular complex at the active site, wherein binding to the molecule or molecular complex is indicative of potential modification of S. aureus peptide deformylase activity.

In another aspect, the present invention provides a method for making a potential modifier of S. aureus peptide deformylase activity, the method including chemically or enzymatically synthesizing a chemical entity to yield a potential modifier of S. aureus peptide deformylase activity, the chemical entity having been designed during a computer-assisted process including supplying a computer modeling application with a set of structure coordinates of a molecule or molecular complex, the molecule or molecular complex including at least a portion of a S. aureus peptide deformylase or S. aureus peptide deformylase-like active site; supplying the computer modeling application with a set of structure coordinates for a chemical entity; evaluating the potential binding interactions between the chemical entity and the active site of the molecule or molecular complex; structurally modifying the chemical entity to yield a set of structure coordinates for a modified chemical entity; and determining whether the chemical entity is expected to bind to the molecule or molecular complex at the active site, wherein binding to the molecule or molecular complex is indicative of potential modification of S. aureus peptide deformylase activity.

In another aspect, the present invention provides a method for making a potential modifier of S. aureus peptide deformylase activity, the method including chemically or enzymatically synthesizing a chemical entity to yield a potential modifier of S. aureus peptide deformylase activity, the chemical entity having been designed during a computer-assisted process including supplying a computer modeling application with a set of structure coordinates of a molecule or molecular complex, the molecule or molecular complex including at least a portion of a S. aureus peptide deformylase or S. aureus peptide deformylase-like active site; forming a chemical entity represented by set of structure coordinates; and determining whether the chemical entity is expected to bind to the molecule or molecular complex at the active site, wherein binding to the molecule or molecular complex is indicative of potential modification of S. aureus peptide deformylase activity.

Table 1 lists the atomic structure coordinates for molecule Staphylococcus aureus peptide deformylase (S. aureus pdf) as derived by x-ray diffraction from a crystal of the protein. The following abbreviations are used in Table 1:

"Atom type" refers to the element whose coordinates are measured. The first letter in the column defines the element.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

Abbreviations

The following abbreviations are used throughout this disclosure:
Staphylococcus aureus (S. aureus)
Escherichia coli (E. coli)
Haemophilis influenzae (Haemop. influenzae)
Bacillus subtilis (B. subtilis)
Mycoplasma pneumoniae (Mycopl. pneumoniae)
Peptide deformylase (pdf)
Isopropylthio-β-D-galactoside (IPTG)
(S)-2-O-(H-phosphonoxy)-L-caproyl-L-leucyl-p-nitroanilide (PCLNA)
Dimethyl sulfoxide (DMSO)
Polyethylene glycol (PEG)
Beta-mercaptoethanol (BME)
Optical density (OD)
Multiple anomalous dispersion (MAD)
Root mean square (r.m.s.)
Root mean square deviation (r.m.s.d.)
PNU-172550 is a compound having the following structure:

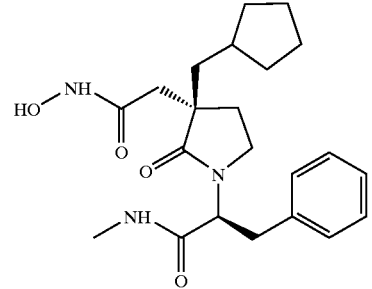

The following abbreviations are used for amino acids throughout this disclosure:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE FIGURES

FIG. 3 lists the amino acid sequences of peptide deformylases from various species of bacteria including *Staphylococcus aureus* peptide deformylase (pdf) with C-terminal 6xHis tag (SEQ ID NO: 1); *Escherichia coli* pdf (SEQ ID NO:2); *Haemophilis influenzae* pdf (SEQ ID NO:3); *Bacillus subtilis* (SEQ ID NO:4); and *Mycoplasma pneumoniae* (SEQ ID NO:5); and *Staphylococcus aureus* def1 gene (a related but inactive form of the protein, also called Pseudo pdf) (SEQ ID NO:6). Alignments were generated from GCG SeqLab (Wisconsin Package Version 10.1, Genetics Computer Group, Madision, Wis.). The underlined residues show regions of importance to the activity of peptide deformylases. The boxed amino acids show mutations for *S. aureus* pdf (SEQ ID NO:1).

FIG. 10 is a sequence alignment based on x-ray structure comparisons for *E. coli* pdf (SEQ ID NO:8) and *S. aureus* pdf (SEQ ID NO:7) proteins.

Figure 1:
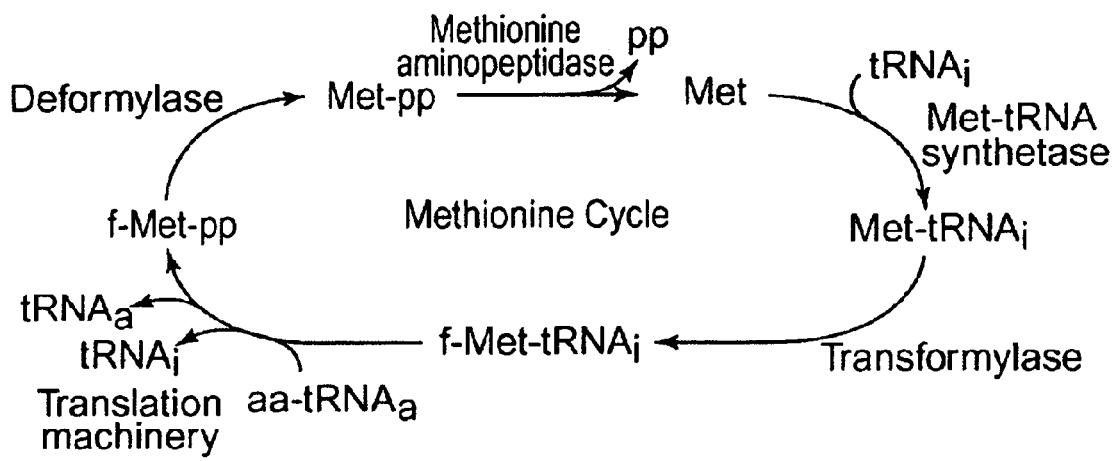
FIG. 1 is a schematic representation of the methionine cycle in bacteria.
Figure 2:
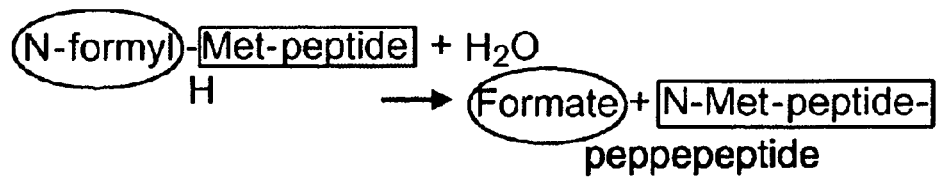
FIG. 2 is a schematic representation of the reaction catalyzed by peptide deformylase.

DETAILED DESCRIPTION OF THE INVENTION $C222_1$ Space Group Crystals

In one embodiment, crystals of *S.aureus* pdf have been obtained and belong to the $C222_1$ orthorhombic space group. Crystals were grown in four conditions, but crystals used for the structure solution were grown from 20% PEG 4000, 0.1M Tris pH=8.5 and 0.1M $MgCl_2$. Se-methionine pdf crystals were also grown and data was used to solve the pdf structure. Variation in buffer and buffer pH as well as other additives such as PEG is apparent to those skilled in the art and may result in similar crystals.

The *S. aureus* pdf protein was over-expressed and purified from *E.coli*. Crystallization attempts using pdf purified only by affinity Ni-NTA chromatography did not yield crystals, but the addition of an anion exchange purification step improved results. This further purified material resulted in many promising crystallization leads including four unique hits. Each of these hits were followed up using finely focused grid screens. All four conditions were pursued and characterized according to crystal behavior and quality. All small crystals were optimized though micro-seeding. Large, single crystals suitable for data collection were soaked in stabilization solution containing 25% glycerol prior to freezing for low temperature data collection. The useful crystals grown from the four diverse starting conditions all belong to the space group $C222_1$ with one molecule in the asymmetric unit. The unit cell parameters were a=94.1 b=121.87 c=47.58 Å.

Identical crystals of pdf were grown with Se-methionine pdf protein. One crystal was grown from 20% PEG 4000, 0.1M Tris pH=8.5 and 0.1 m $MgCl_2$ and measured 0.22× 0.22×0.6 micrometer. Data from this crystal was collected at the IMCA synchrotron facility and was found to belong to the space group $C222_1$ as well. The pdf structure was solved using this MAD data. However, the resulting structure could not be completely refined with the MAD data; so refinement was abandoned in favor of a new data set (see below).

A second crystal was grown in the presence of 2 mM of a potential inhibitor, 10% DMSO, 20% PEG 4000, 0.1M Tris pH=8.5 and 0.1M $MgCl_2$. This crystal measured 0.28× 0.28×0.98 micrometer. No evidence for this compound was observed in the electron density map. After freezing the crystal, data was collected on a Siemens dual Hi-star. The crystal diffracted to 1.9 Å and molecular replacement was successfully performed using the MAD-derived model. This structure was refined to a final R-factor of 18.62%.

The orthorhombic crystal form could be prepared with or without compounds. The crystals belonging to the $C222_1$ space group generally have unit cell parameters with a=91.6 to 95.1 Å; b=121.3 to 123.5 Å; and c=47.6 to 48.4 Å. Crystals may be grown at 20° C., for example, by mixing a buffered protein sample with 19% PEG4000, 0.1M Tris pH 8.5 and 0.2M $MgCl_2$. Crystals may be stabilized in 25% PEG4000; 10% glycerol; 0.1M Tris pH 8.5 and 0.2M $MgCl_2$ for data collection.

C2 Space Group Crystals

The Monoclinic crystal form of S. aureus pdf, C2, with unit cell parameters ranging from a=90.8 to 95.1 Å; b=42.4 to 42.7 Å; and c=104.1 to 104.4 Å. Crystals were grown at 20° C. by mixing a buffered protein sample that included 5 mM PNU-172550 with an equal volume of 30% PEG 3000; 0.1M Na Citrate pH 5.2. Other compounds could be crystallized using the same procedure with variation in PEG concentration or pH. Crystals were stabilized in a solution containing PEG; Citrate, PNU-172550 and 10% glycerol for diffraction studies.

$P4_22_12$ Space Group Crystals

Another crystal form could also be prepared with PNU-172550. This tetragonal crystal form $P4_22_12$ has unit cell parameters ranging from a=b=160.4 to 163.5 Å and c=45.2 to 48.3 Å. Crystals are grown at 20° C. by mixing a buffered protein sample that included 5 mM PNU-172550 with an equal volume of 1.375 M Na Citrate and 0.1 M Na Hepes pH 7.5. Other compounds could be crystallized using the same procedure with variation in salts and buffers. Most often no stabilization solution was employed.

Comparision of S. aureus pdf and E. coli pdf Crystals

A number of structure determination reports have reported the crystallization of the pdf from E.coli as shown in Table 2. The present disclosure is believed to be the first crystallization of S.aureus pdf, and the reported crystal forms are also unique.

TABLE 2

The Space group and unit cell parameters for a variety of E. coli pdf crystals.

| PDB No. | Space Group | A edge | B edge | C edge | Beta angle | A.U. |
|---|---|---|---|---|---|---|
| 1 bs4 | $C2_1$ | 140.70 | 63.30 | 86.8 | 120.6 | 3 |
| 1 bs5 | $C2_1$ | 143.4 | 64.10 | 84.6 | 123.2 | 3 |
| 1 bs6 | $C2_1$ | 143.8 | 64.10 | 85.10 | 123.3 | 3 |
| 1 bs7 | $C2_1$ | 143.4 | 64.0 | 84.50 | 123.0 | 3 |
| 1 bs8 | $C2_1$ | 143.1 | 64.2 | 84.7 | 123.3 | 3 |
| 1 bsz | $C2_1$ | 141.0 | 63.4 | 86.8 | 120.6 | 3 |
| 1 dff | $P6_122$ | 55.35 | 55.35 | 230.92 | 120 | 1 |
| 1 icj | $C2_1$ | 140.7 | 63.4 | 86.9 | 120.6 | 3 |
| 1 bsj | $P6_522$ | 98.38 | 98.38 | 109.37 | 120 | 1 |
| 1 bsk | $P6_522$ | 100.11 | 100.11 | 111.34 | 120 | 1 |

X-ray Crystallographic Analysis

Each of the constituent amino acids of S. aureus pdf is defined by a set of structure coordinates as set forth in Table 1. The term "structure coordinates" refers to Cartesian coordinates derived from mathematical equations related to the patterns obtained on diffraction of a monochromatic beam of x-rays by the atoms (scattering centers) of an S. aureus pdf complex in crystal form. The diffraction data are used to calculate an electron density map of the repeating unit of the crystal. The electron density maps are then used to establish the positions of the individual atoms of the S. aureus pdf protein or protein/ligand complex.

Slight variations in structure coordinates can be generated by mathematically manipulating the S. aureus pdf or S. aureus pdf/ligand structure coordinates. For example, the structure coordinates set forth in Table 1 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the S. aureus pdf or S. aureus pdf/ligand complex, as defined above, would not be expected to significantly alter the nature of ligands that could associate with the active sites. Thus, for example, a ligand that bound to the active site of S. aureus pdf would also be expected to bind to or interfere with another active site whose structure coordinates define a shape that falls within the acceptable error.

Binding Pockets/Active Sites/Other Structural Features

The present invention has provided, for the first time, information about the shape and structure of the active site of S. aureus pdf.

Active sites are of significant utility in fields such as drug discovery. The association of natural ligands or substrates with the active sites of their corresponding receptors or enzymes is the basis of many biological mechanisms of action. Similarly, many drugs exert their biological effects through association with the active sites of receptors and enzymes. Such associations may occur with all or any parts of the active site. An understanding of such associations helps lead to the design of drugs having more favorable associations with their target, and thus improved biological effects. Therefore, this information is valuable in designing potential modifiers of S. aureus pdf-like activity, as discussed in more detail below.

The term "active site (or binding pocket)," as used herein, refers to a region of a molecule or molecular complex, that, as a result of its shape, favorably associates with another chemical entity or compound. Thus, an active site may include or consist of features such as interfaces between domains. Chemical entities or compounds that may associate with an active site include, but are not limited to, cofactors, substrates, inhibitors, agonists, antagonists, etc.

The active site of S. aureus peptide deformylase may be represented by the amino acids in the following table, which are believed would fall within 5 Å of an incorporated modifier. Using structure coordinates of E. coli pdf with bound PCLNA and the present S. aureus pdf, the structures were superimposed using the Pharmacia program SUPER-PDB.

In Model A, the 12 residues that are identical between E. coli pdf and S. aureus pdf were superimposed and chosen as the set to be minimized. The resulting distances between the α-Cs for the 12 residues, and the RMS for all the atoms in each of the corresponding residues were calculated and are reported in Table 3.

In Model B, the three residues which coordinate the metal atom (Cys111, His154, and His158 for S. aureus pdf) were chosen as the set to be minimized, and other residues within 2 Å were brought into the refinement. The resulting distances between the α-Cs for 18 active site amino acids and the RMS for all the atoms in each of the corresponding residues were calculated and are reported in Table 3.

In Model C, the 12 residues that are identical between *E. coli* pdf and *S. aureus* pdf were chosen as the set to be minimized, and other residues within 2 Å were brought into the refinement. The distances between the α-Cs for 18 active site amino acids and the RMS for all the atoms in each of the corresponding residues were calculated and are reported in Table 3.

sufficiently similar to at least a portion of the active site of *S. aureus* pdf as to be expected to bind related structural analogues. A structurally equivalent active site is defined by a root mean square deviation from the structure coordinates of the backbone atoms of the amino acids that make up the active sites in *S. aureus* pdf (as set forth in Table 1) of at most about 0.8 Å, and preferably less than about 0.35 Å. How this calculation is obtained is described below.

The term "associating with" refers to a condition of proximity between a chemical entity or compound, or portions thereof, and an *S. aureus* pdf molecule or portions thereof. The association may be non-covalent, wherein the

TABLE 3

Active Site Residues

| | | Model A | | Model B | | Model C | |
|---|---|---|---|---|---|---|---|
| *S. aureus* | *E. coli* | α-C Dist., Å | RMS (all atoms) | α-C Dist., Å | RMS (all atoms) | α-C Dist., Å | RMS (all atoms) |
| Arg56 | Glu41 | — | — | Too Long | | Too Long | |
| Ser57 | Glu42 | — | — | 1.8337 | 2.1387 | 1.8194 | 2.1266 |
| Gly58 | Gly43 | 0.4093 | 0.4619 | 0.7992 | 0.8537 | 0.7834 | 0.8379 |
| Val59 | Ile44 | — | — | 0.4870 | 1.4130 | 0.4875 | 1.4151 |
| Gly60 | Gly45 | 0.5142 | 0.5109 | 0.4953 | 0.4869 | 0.4944 | 0.4876 |
| Leu61 | Leu46 | 0.4495 | 0.4802 | 0.4177 | 0.4842 | 0.4293 | 0.4902 |
| Gln65 | Gln50 | 0.1933 | 0.2696 | 0.4340 | 0.4239 | 0.4216 | 0.4156 |
| Leu105 | Ile86 | — | — | 0.9699 | 1.5517 | 0.9858 | 1.5510 |
| Pro106 | none | — | — | — | — | — | — |
| Thr107 | none | — | — | — | — | — | — |
| Gly108 | Glu87 | — | — | 1.7757 | 1.7415 | 1.7446 | 1.7150 |
| Glu109 | Glu88 | 0.2880 | 0.3478 | 0.6969 | 0.5832 | 0.6699 | 0.5618 |
| Gly110 | Gly89 | 0.2008 | 0.1993 | 0.6020 | 0.4590 | 0.5843 | 0.4439 |
| Cys111 | Cys90 | 0.3367 | 0.4177 | 0.3111 | 0.4429 | 0.3104 | 0.4398 |
| Leu112 | Leu91 | 0.6834 | 0.9241 | 0.6170 | 0.8266 | 0.6151 | 0.8243 |
| Asn117 | Arg97 | — | — | Too Long | | Too Long | |
| Tyr147 | Leu125 | — | — | 1.1351 | 1.1966 | 1.1011 | 1.1681 |
| Ile150 | Ile128 | 0.1519 | 0.3571 | 0.4175 | 0.5381 | 0.3877 | 0.5129 |
| Val151 | Cys129 | — | — | 0.5516 | 0.5981 | 0.5282 | 0.5765 |
| His154 | His132 | 0.2017 | 0.3312 | 0.2066 | 0.2882 | 0.2093 | 0.2909 |
| Glu155 | Glu133 | 0.2294 | 0.3944 | 0.3929 | 0.4743 | 0.3869 | 0.4745 |
| His158 | His136 | 0.2387 | 0.3944 | 0.2444 | 0.3116 | 0.2330 | 0.3050 |
| Composite RMS | | 0.36 | 0.46 | 0.83 | 0.98 | 0.81 | 0.97 |

The active site of *S. aureus* pdf preferably includes at least a portion of the amino acids Gly58, Gly60, Leu61, Gln65, Glu109, Gly110, Cys111, Leu112, Ile150, His154, Glu155, and His158; and more preferably at least a portion of the amino acids Arg56, Ser57, Gly58, Val59, Gly60, Leu61, Gln65, Leu105, Pro106, Thr107, Gly108, Glu109, Gly110, Cys111, Leu112, Asn117, Tyr147, Ile150, Val151, His154, Glu155, and His158, as shown in Table 1. As used herein, "at least a portion of the amino acids" means at least about 50% of the amino acids, preferably at least about 70% of the amino acids, more preferably at least about 90% of the amino acids, and most preferably all the amino aicds. It will be readily apparent to those of skill in the art that the numbering of amino acids in other isoforms of *S. aureus* pdf may be different.

The amino acid constituents of an *S. aureus* pdf active site as defined herein, as well as selected constituent atoms thereof, are positioned in three dimensions in accordance with the structure coordinates listed in Table 1. In one aspect, the structure coordinates defining the active site of *S. aureus* pdf include structure coordinates of all atoms in the constituent amino acids; in another aspect, the structure coordinates of the active site include structure coordinates of just the backbone atoms of the constituent atoms.

The term "*S. aureus* pdf-like active site" refers to a portion of a molecule or molecular complex whose shape is juxtaposition is energetically favored by hydrogen bonding, van der Waals forces, or electrostatic interactions, or it may be covalent.

Accordingly, the invention thus provides molecules or molecular complexes including an *S. aureus* pdf active site or *S. aureus* pdf-like active site, as defined by the sets of structure coordinates described above.

The crystal structure of the *Staphylococcus aureus* peptide deformylase enzyme (the def2 gene product) has been determined by MAD phased X-ray crystallography to 2.0 Å resolution. The protein structure reveals a fold similar to but not identical to the well characterized *E. coli* enzyme. Differences also extend into the active site region and will play a role in the elaboration of peptide deformylase (pdf) specific inhibitors.

Description of the Structure of pdf

Figure 5:
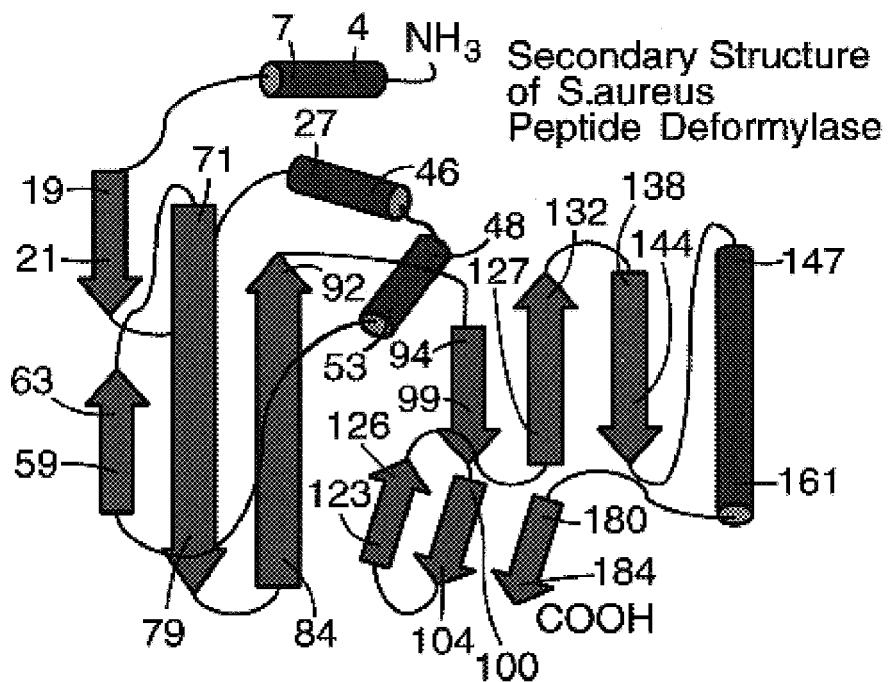
FIG. 5 is a schematic secondary structure diagram of *S. aureus* pdf. The cylinders represent helices and the arrows represent sheets.

The pdf structure is composed mostly of β-sheet with two lengthy helical regions near the n and c-terminus (FIG. 5). The last helical region (147-161) forms the core of the structure and is also involved in catalysis. The β-sheet regions surround the centrally located, c-terminal helix and help to create the shallow cavity into which the substrates, formylated peptides, fit. The conserved motif HEXXH (H154 through H158) is found on this c-terminal helix and is involved in the coordination of the active site metal ion. Glutamic acid 155 is also likely essential for the catalytic process. Residues nearer the beginning of the helix are likely involved in specificity and are found near the opening of the cavity.

Figure 6:
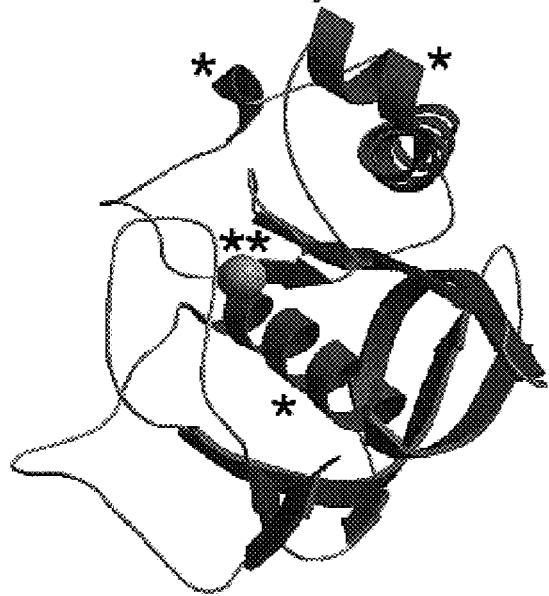
FIG. 6 is a depiction of the secondary structure of *S. aureus* peptide deformylase. The α-helices are starred and the β-sheets are not starred. The single Zn/Fe atom is labeled **.
Figure 7:
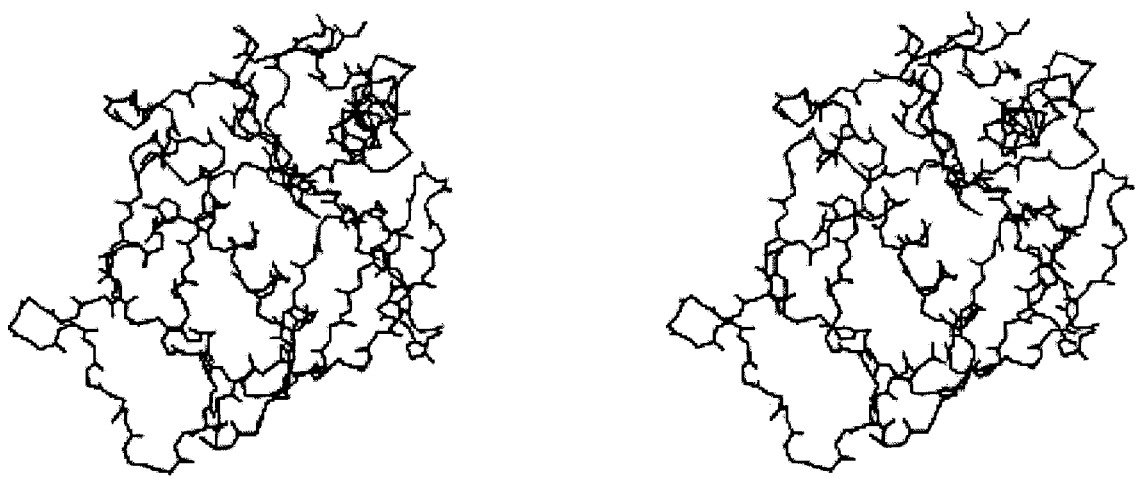
FIG. 7 is a stereo pair view of *S. aureus* peptide deformylase backbone from the same view as in FIG. 6.

The n-terminal helical segments form a knot-like cluster on the "top" of the protein while the β-sheet regions are found on the lower half of the protein. A "thumb" region of coil extends from the lower sheet and covers the top of the metal ion (Center left FIG. 6). The β-sheet rich section is composed of three β-sheet elements, an n-terminal anti-paralell three stranded β-sheet, a central anti-paralell three stranded β-sheet and a c-terminal mixed β-sheet. The β-sheet elements pack around the active site helix and form the walls of the active site cavity. The c-terminus of the protein forms a last short strand of mixed β-sheet and is poised at the mouth of the active site (FIG. 7).

The structure has a large number of well ordered waters which have been placed into the electron density maps based upon 3 sigma difference density during the refinement as well as the potential for good hydrogen bonding. Many waters fill the active site cavity.

Figure 8:
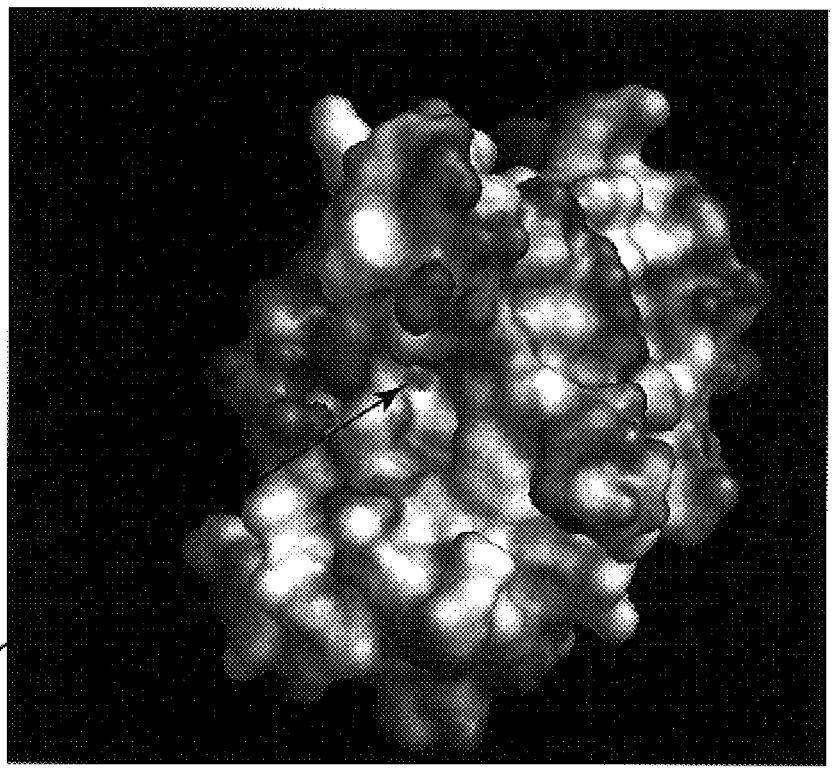
FIG. 8 is a model showing the electrostatic surface potential for pdf. The positively charged region is indicated by the arrow (+100 kcal) while the negatively charged regions are gray (–100 kcal). The surface potential was created in MOSAIC2 (Computer Aided Drug Discovery) using point charge parameters derived from the AMBER force field (Weiner et al., *J. Comput. Chem.*, 7:230–52 (1986)) and a formal charge of plus 2 for the metal ion.
Figure 9:
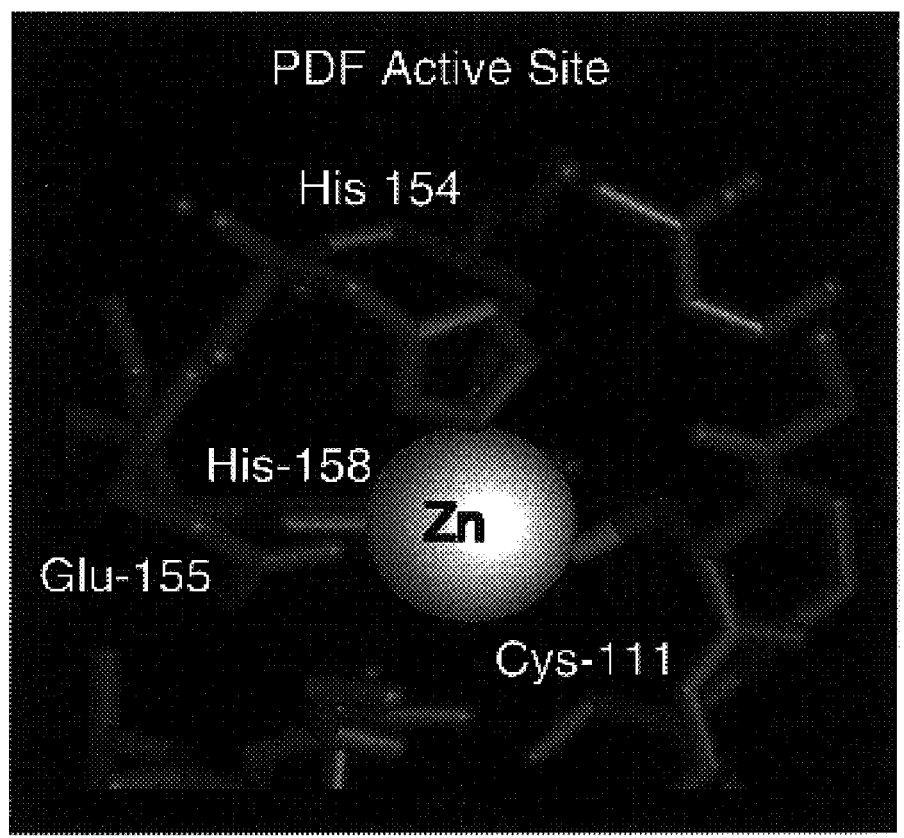
FIG. 9 is a schematic model showing the active site metal ion (gray sphere). The metal ion may be Zn, Ni, or Fe. The ion is coordinated by protein sidechains H154, H158 and C111.

The electrostatic surface potential of pdf indicates an intense positively charged surface at the back of the active site cavity—due to the presence of the metal ion. The upper surface of the protein is richly decorated with negatively charged residues, while the lower surface is generally more neutral in potential (FIG. 8).

The Active Site Metal Ion

A large body of experimental data including X-ray and NMR structures suggests that pdf contains a metal ion in the active site (Meinnel et al., *J. Bacteriol.*, 175:993–1000 (1993); Meinnel et al., *J. Bacteriol.*, 177:1883–87 (1995); Chan et al., *Biochemistry*, 36:13904–09 (1997)). In addition, activity data (Rajagopalan et al., *Biochemistry*, 36:13910–18 (1997); Rajagopalan et al., *J.Am.Chem.Soc.*, 119:12418–19 (1997)) point to iron as the most active metal ion. Data is consistent with this view; however, we have no experimental evidence based upon the present X-ray data to distinguish among ions like nickel, iron or zinc. From the initial MAD map it was clear that that a tetrahedrally coordinated metal ion is found in the three-dimensional structure of *S.aureus* pdf with water and the protein sidechains H154, H158, and C111 coordinating the metal ion. The sequence motif HEXXH (Mazel et al., *EMBO J.*, 13:914–23 (1994)) in the c-terminal helix is a signature motif which is found in many metalloproteases including thermolysin (Blundell, *Nat.Struct.Biol.*, 1:73–75 (1994); Jongeneel et al., *FEBS Lett.*, 242: 211–14 (1989); Makarova et al., *J. Mol. Biology*, 292:11–17 (1999)). The glutamic acid residue of this motif probably plays a dual role in metal coordination and catalysis. The water molecule, which is a metal ligand, is tightly held in place by this glutamate residue in the present crystal structure. This residue likely plays a role in the protonation and deprotonation of reaction intermediates during the catalytic cycle in a manner similar to the role of the conserved glutamate in thermolysin (Matthews, *Acc.Chem.Res.*, 21: 333–40 (1988); Chan et al., *Biochemistry*, 36:13904–09 (1997)).

Comparison of *S. aureus* pdf to *E. coli* Structure

With the availability of numerous *E.coli* pdf X-ray and NMR structures (Table 1), it is possible to carry out a detailed comparison between these related enzymes. It should first be noted that the sequence identity between the *E.coli* and *S.aureus* enzymes is 45/134 or 33.5%. The rmsd for 134 α-carbons is 1.101 Å (1.457 Å for 861 common atoms; 1.189 Å for 536 main chain atoms). The vast majority of the identities (shown in FIG. 10) are limited to the conserved motifs (metal binding regions). A structure-based alignment of the protein sequence is given in FIG. 10. The poor sequence identity is not reflected in overall structural similarity. Both enzymes possess similar features in tertiary structure (FIG. 11).

*S.aureus* pdf has seven insertions with respect to the *E.coli* sequence (FIG. 10). The first insertion T3-M4 adds some additional hydrophobic surface area which forms a small surface for interaction with the third insertion (the extended n-terminal helix) N43-G54. The insertion after P25 adds one additional residue to the turn, which leads into the first long helix of pdf. The n-terminal helix is extended by an additional helix (insertion three N43-G54) which is not present in the *E.coli* structure. In the *E.coli* structure this helix is followed by a beta turn which drops down into the very conserved GXGLAA (SEQ ID NO:9) sequence which forms the third (and edge) strand of the n-terminal β-sheet. This strand also forms part of the wall of the active site crevice and provides loci for hydrogen bonding of peptide substrates (Hao et al., *Biochemistry*, 38: 471–19 (1999)). The insertion of residues G81–G83 in the *S.aureus* structure extends the turn between strands II and III of the n-terminal β-sheet. The insertion of V100 is in the turn between strand I of the central anti-parallel β-sheet and the central strand of the c-terminal mixture sheet. Insertion six occurs at the end of the central strand of the mix sheet and includes P106 and T107. These residues are positioned at opening of the active site crevice and may be important determinates of *S.aureus* specificity. The subsequent conserved residues EGCLS (SEQ ID NO:10) form the other wall of the active site crevice. Residue C111 at the center of the sequence is one of the active site metal ligands. The conserved glutamic acid projects downward to form a part of the crevice wall and makes a conserved salt bridge with R124, which is found in the center of the first strand of the mix β-sheet. The insertion of A119 results in a slight bulge of the connecting strand (with respect to the *E.coli* structure) which precedes the first strand of the c-terminal mixed β-sheet. The seventh insertion, the sixth insertion (P106/T107) and the c-terminal extension are all in close proximity and constitute a *S.aureus* specific surface.

Figure 11A:
FIG. 11 is a depiction of the secondary structure of pdf for a) *S. aureus* pdf and b) *E. coli* pdf. The n-terminus ends are starred.
Figure 11B:
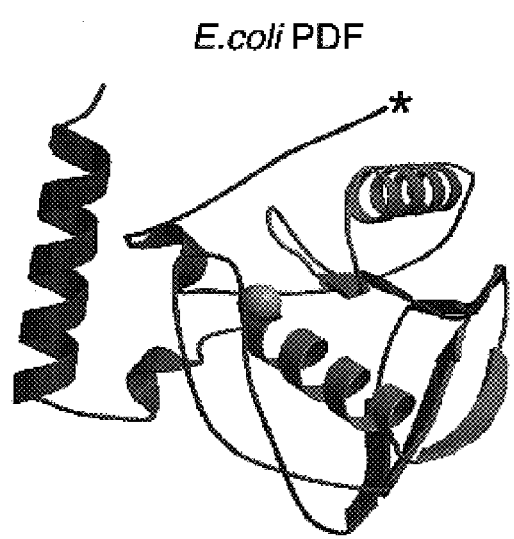
Figure 12:
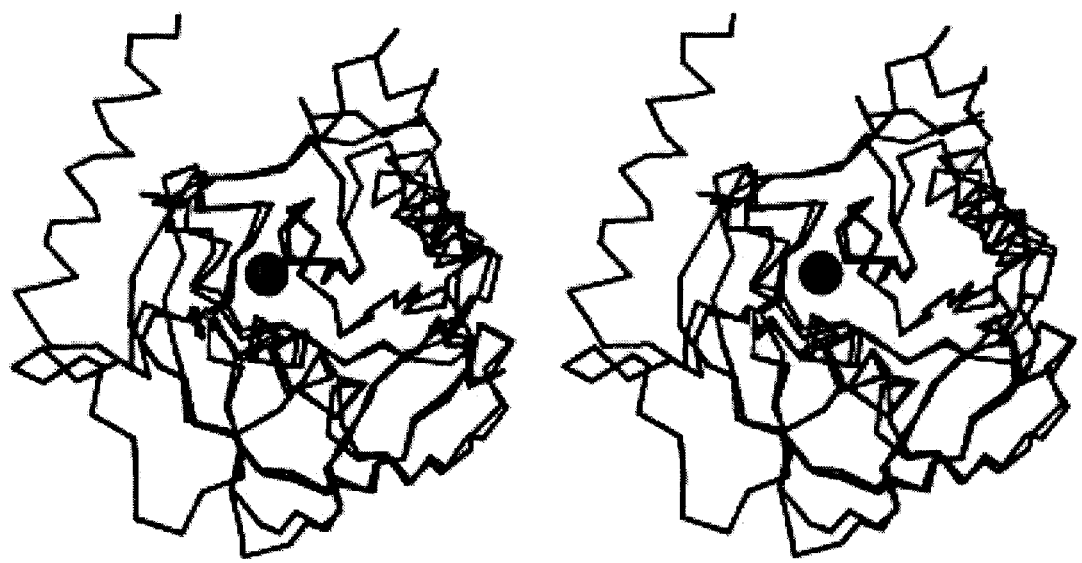
FIG. 12 is a stereo pair view of the superimposed alpha carbons from *S. aureus* pdf and *E. coli* pdf. The metal ion is indicated by the sphere.

From the simplest comparison of these two X-ray structures one is immediately struck by the obvious difference at the c-terminus (FIG. 11). The *E.coli* enzyme has a long protruding α-helix which abutts the protein surface behind the active site cavity. The c-terminus of the *S.aureus* enzyme does not contain an equivalent α-helix, but wraps around the lower aspect of the thumb region to make a short stretch of β-sheet, terminating near the opening of the active site cavity. This is the major topological difference between the two structures, otherwise the proteins follow the same pattern and direction of secondary structure. Superposition of the two proteins permits a more detailed comparison of the alignment of secondary structural elements (FIG. 12) and was the basis of the structure-based sequence alignment of FIG. 10. A superficial evaluation would suggest that the core α-helix and the surrounding β-sheet is the most closely conserved region of the two proteins. Loops near the surface tend to be the location of insertions as is discussed above.

Figure 13:
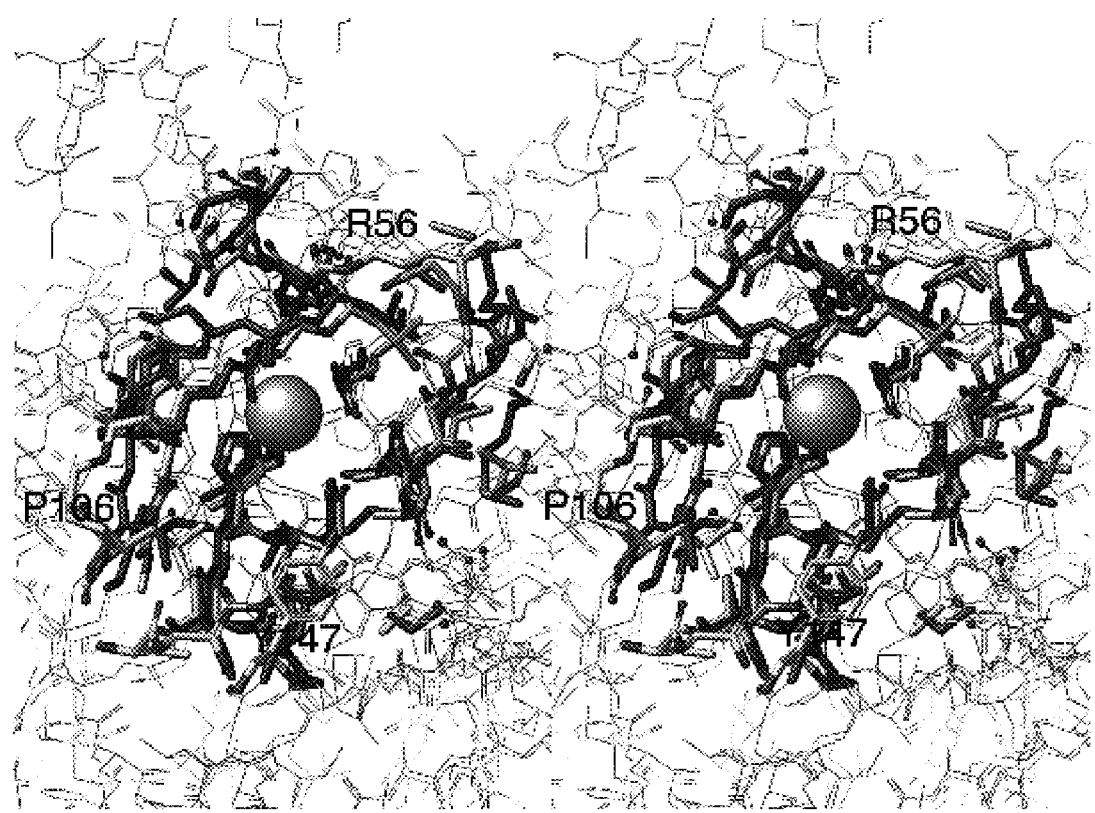
FIG. 13 is a stereo pair view of the superposition of the active site cavity of the *E. coli* pdf structure. Some selected residues from *S. aureus* pdf are labeled.

It follows from the low sequence identity between these two proteins, that the lining of the active site cavity would not be identical between *S.aureus* and *E.coli*. This expectation is in fact born out by the present structure (FIG. 13). Analysis of the active site cavity suggests that 9 residue changes are found in the crevice and the annulus about the crevice. These changes are indicated in the table below (Table 4). Some particularly interesting changes include the replacement of R56 (*S.aureus*) for R97 (*E.coli*) where the arginine sidechain is conserved but changes the side of the cavity from which it projects. A number of subtle hydrophobic-hydrophobic changes are observed as are a number of polar-polar changes.

TABLE 4

Difference in the active site residue between S. aureus and E. coli pdf.

| S. aureus | E. coli | S. aureus | E. coli |
|---|---|---|---|
| V59 | I44 | T107 | E87 |
| S57 | E42 | P106 | — |
| R56 | E41 | L105 | I86 |
| N117 | R97 | Y147 | L125 |
| I150 | I128 | V151 | C129 |

Figure 14A:
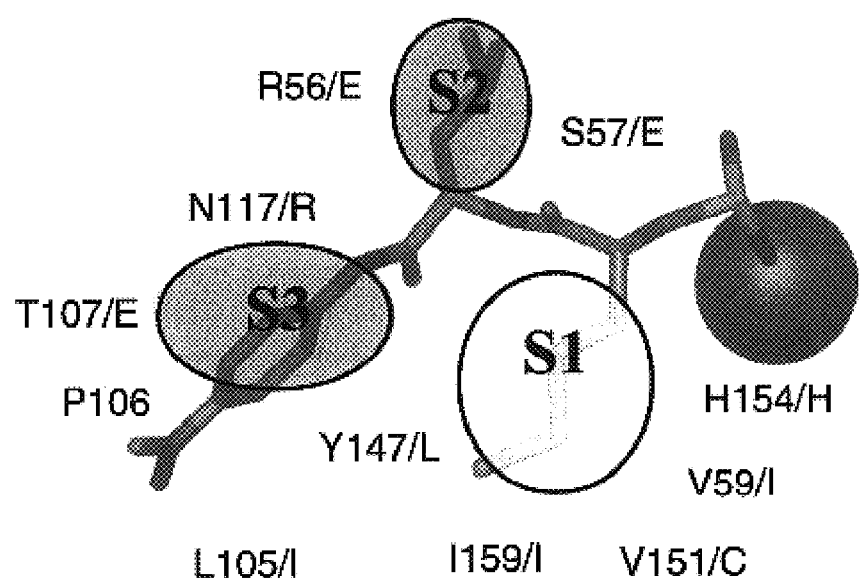
FIG. 14a is a schematic illustration of PCLNA inhibitor (Hao et al., *Biochemistry*, 38: 4712–19 (1999)) placing subsituents into three pdf subsites. The *S. aureus* residue number is given first with the equivalent *E. coli* amino acid subsequent. The metal ion is the labeled sphere.
Figure 14B:
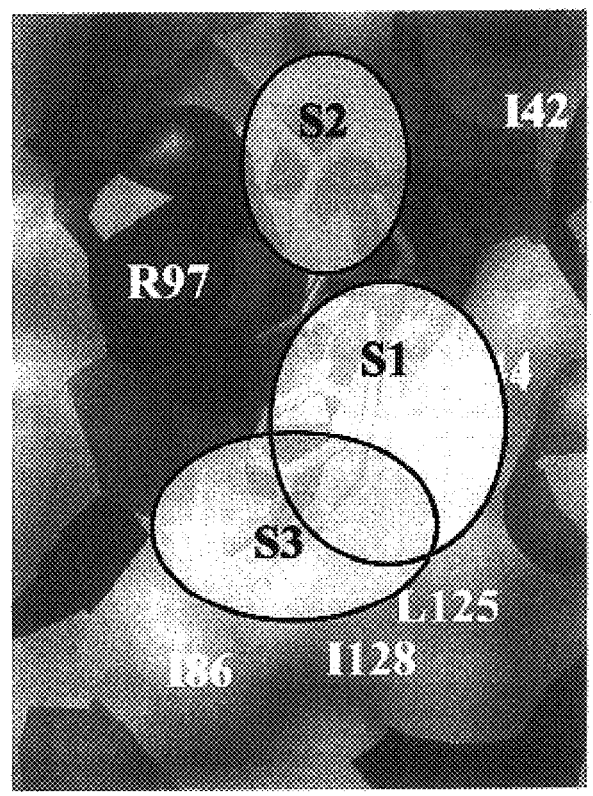
FIG. 14b is a view of a surface rendering for the PCLNA complex with the *E. coli* enzyme with the location of the subsites indicated.

The X-ray structure of the (S)-2-O-(H-phosphonoxy)-L-caproyl-L-leucyl-p-nitroanilide (PCLNA) with the E.coli pdf enzyme (Hao et al., Biochemistry, 38: 4712–19 (1999)) can be used to guide the identification of the subsites (active sites) within the enzyme which accommodate the substrate amino acid sidechains (Schechter et al., BBRC, 27:157–62 (1967)). Using this scheme, the methionine analogue (caproyl), the P1 subsituent, would occupy the S1 subsite; leucine, P2, the S2 subsite; and the p-nitroanilide, P3, the S3 subsite. With the PCLNA inhibitor as a frame of reference, superposition (as above) with the present S.aureus pdf X-ray structure permits the general comparison of the S.aureus with the corresponding E.coli subsites. This comparison is schematically shown in FIG. 14. The β-sheet mainchain conformation of the inhibitor forces the inhibitor subsituents to adopt the typical down-up-down disposition observed for most peptidomimetic inhibitors. The P1 and P3 subsituents interact via the intra-molecular hydrophobic interface (between the caproyl and aromatic ring) to form a continuous surface which fills the S1 and S3 subsites. The P2 subsituent projects away from the protein surface toward solvent.

Figure 15:
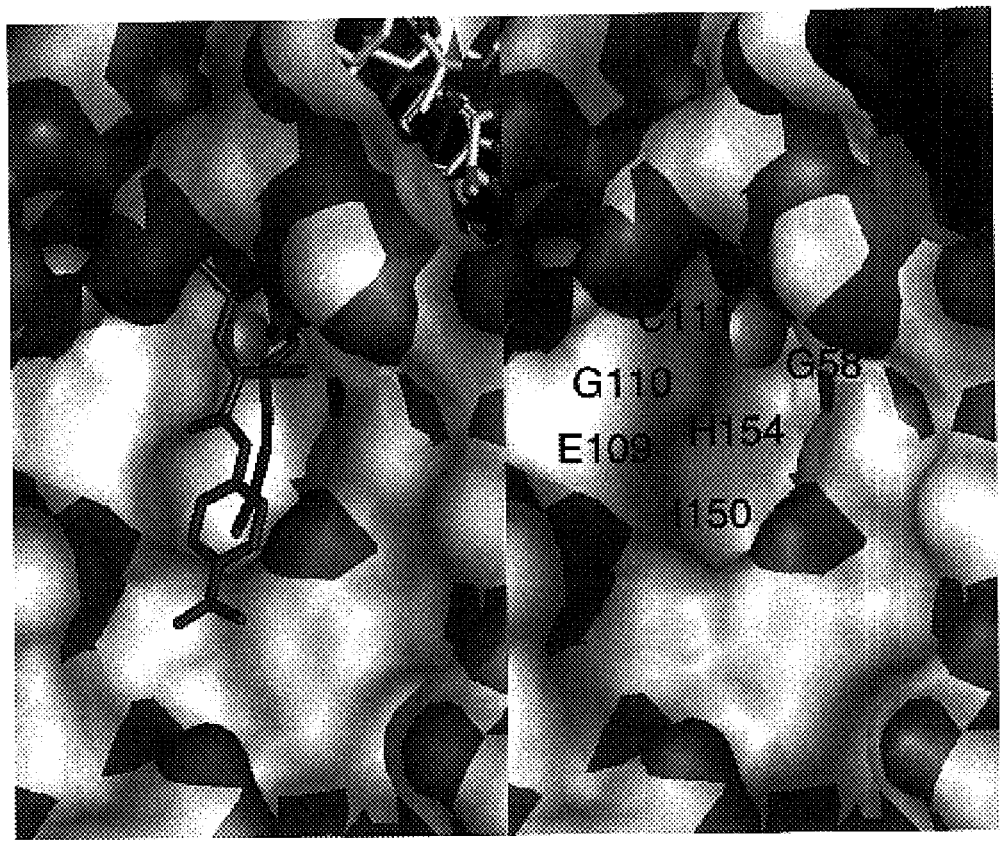
FIG. 15 is a view of a model of the active site cleft of *S. aureus* pdf with PCLNA (from Hao et al., *Biochemistry*, 38:4712–19 (1999)). The six active site residues which are conserved between *E. coli* and *S. aureus* pdf are indicated. These residues line the bottom of the active site.
Figure 16:
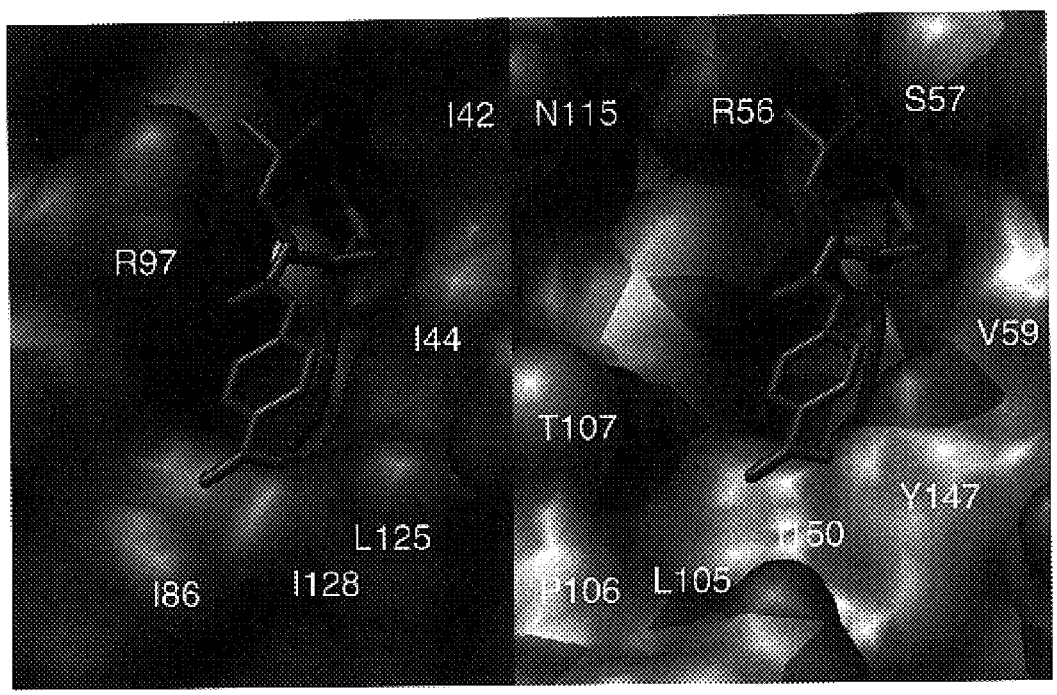
FIG. 16 is a view of a model of the surface rendering for PCLNA complex with *E. coli* enzyme (left) and of PCLNA with *S. aureus* enzyme (right). Amino acid labeling indicates the surface corresponding to various residues.

Comparison of the E.coli and S.aureus crystal structures indicates that six residues in the region of the active site are conserved. In fact, five are always conserved in pdf sequence (ETB data not shown). The residues come from the three regions of greatest sequence identity; Gxglaa (SEQ ID NO;9), EGCls (SEQ ID NO:10), and IxxqHexdhl (SEQ ID NO:11), where the capitization indicates a conserved residue in the active site crevice. The glycine is the lone invariant amino acid on the right side of cleft (FIG. 15). The glutamic-glycine-cysteine triplet forms the invariant left side of the crevice. Finally, isoleucine and histidine are found at the bottom of the active site crevice (FIG. 15). These conserved residues form a continuous invariant surface which extends from the methionine (caproyl) site (S1) and up the left wall of the crevice. The variable residues encircle the upper aspect of the crevice. The differences account for the subtle differences in crevice shape when the two enzymes are compared—and presumably will be important determinates for inhibitor specificity.

Figure 17:
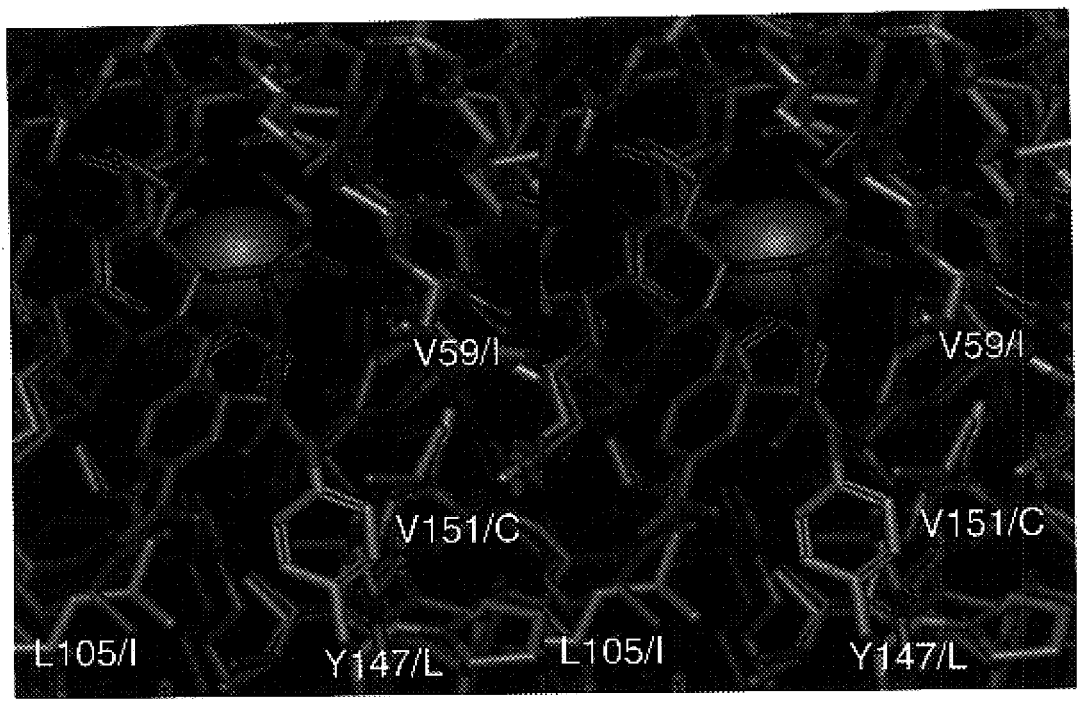
FIG. 17 is a stereo view of the S1 subsite of pdf with PCLNA inhibitor. The amino acid sidechains which surround the P1, caproyl group, are indicated. Labels indicate the *S.aureus* amino acid first and the equivalent *E. coli* second.

The S1 subsite has the greatest surface conservation between E.coli and S.aureus. This is due to the sequence conservation (outlined above) of the amino acids which form the bottom of the crevice—primarily H154, which also coordinates the metal ion, and I150. The long and fairly narrow hydrophobic subsite appears well-designed to cradle the preferred methionine residue. The rightside crevice wall is defined by V59(I, E.coli), Y147L, I150I, V151C, and L105I (FIG. 17). The subsite is an exclusive hydrophobic surface in E.coli; whereas, the hydroxyl group of Y147 introduces a potential hydrogen bonding group in the upper aspect of the rightside of the equivalent S. aureus subsite. The presence of the cysteine in the E.coli enyzme may contribute to the instability of the enzyme and may offer an advantage when working with S.aureus pdf.

Figure 18:
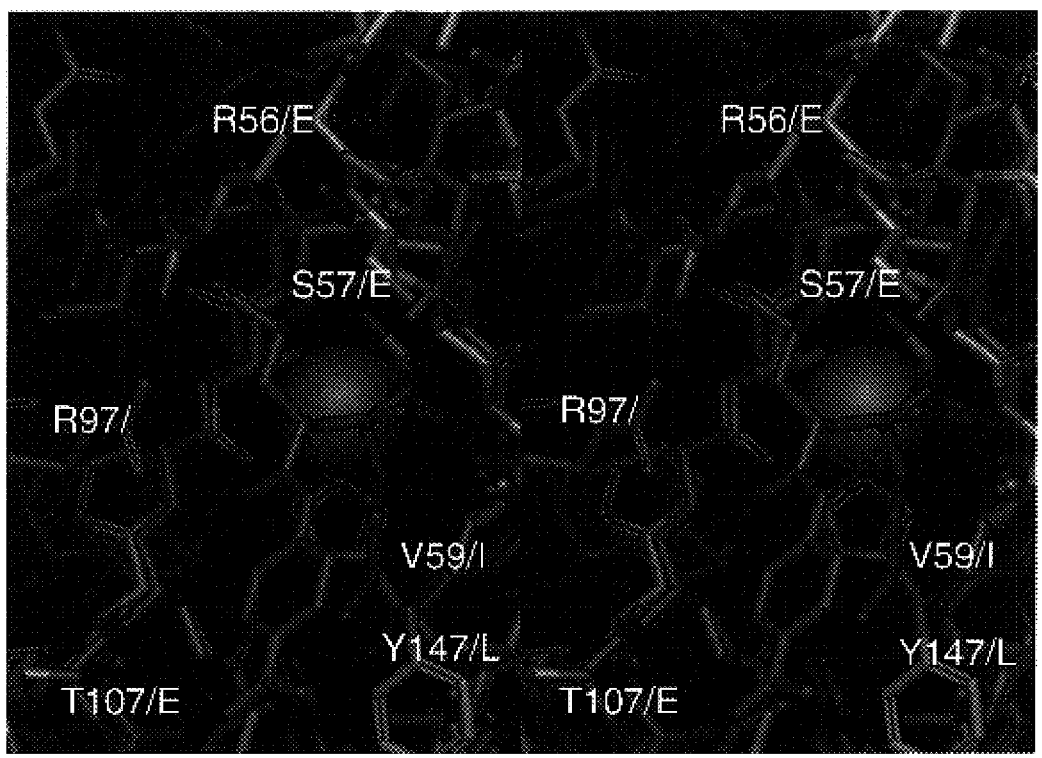
FIG. 18 is a stereo view of the S2 subsite of pdf with PCLNA inhibitor. The amino acid sidechains which surround the P2, leucyl group, are indicated. Labels indicate the *S.aureus* amino acid first and the equivalent *E.coli* residue second. However, R97/N is indicated with the opposite nomenclature.

The S2 subsite is quite different between the two enzymes (FIG. 18). In E.coli R97 projects over the central leftside of the crevice and with E42 slightly narrows the entrance to the subsite. The principle hydrophobic interaction of the P2, leucyl, is with L91(L112, in S.aureus). This residue is always hydrophobic, but not strictly conserved among pdf from different bacteria. The subsite continues unobstructed across the protein surface and is completely accessible to bulk solvent. In S.aureus pdf the E.coli R97 is lost and replaced with R56, which projects from the leftside of the crevice. Also, on the leftside the E.coli E42 is replaced with S57. The sidechain hydroxyl project directly into the S2 subsite and may provide a handle for P2 specific inhibitors directed towards S.aureus. Finally, the S2 subsite in S.aureus is obstructed by R56 which projects across the subsite limiting its depth, and concomitantly providing additional hydrogen bonding determinates.

Figure 19:
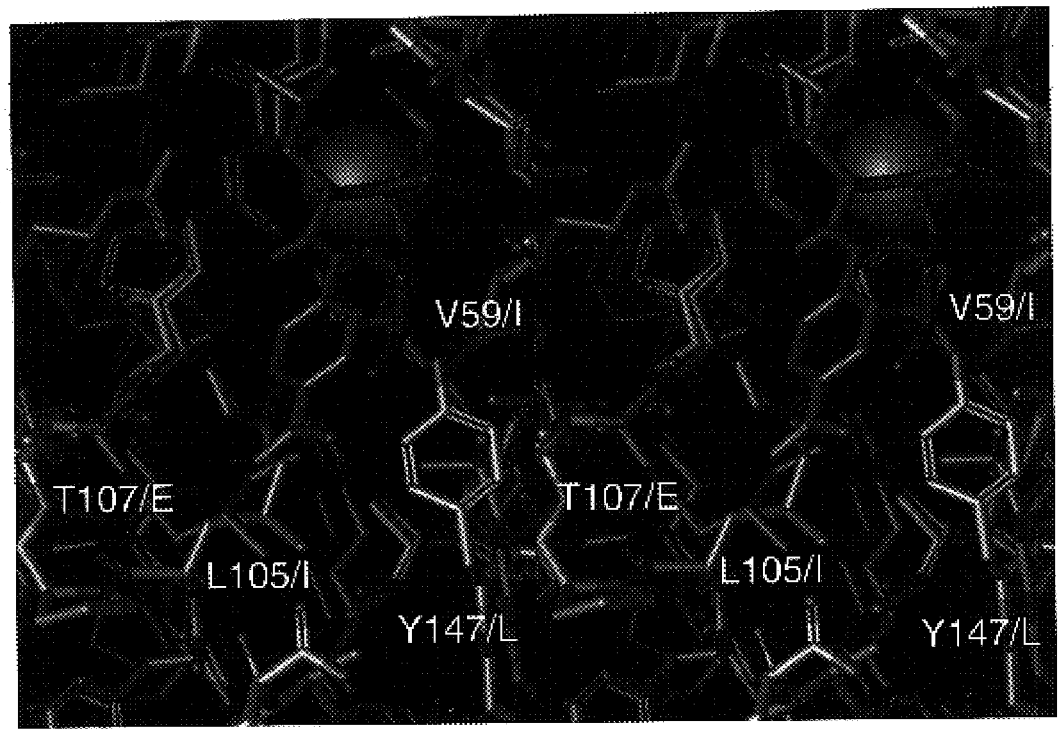
FIG. 19 is a stereo view of the S3 subsite of pdf with PCLNA inhibitor. The amino acid sidechains which surround the P3, p-nitroanilide group, are indicated. Labels indicate the *S.aureus* amino acid first and the equivalent *E.coli* residue second.

The S3 subsite is a broad somewhat flat hydrophobic surface in both enzymes (FIG. 19). Aside from an aliphatic contribution from E109, which is conserved among all pdf enzymes, there are no strictly conserved amino acids in the S3 subsite. The insertion of P106 broadens the subsite in the S.aureus species. The introduction of T107 for glutamatic acid is important as is the amino acid Y147 (as noted above). In the former case, the polar group projects into the subsite in the S.aureus protein and is available for a unique hydrogen bond. In addition the aromatic Y147 and the possible hydrogen bond from the hydroxyl differentiate the rightside of the S3 subsite. These differences between S.aureus and E.coli create distinct features for the S3 subsite, which may be exploited for bacteria-specific pdf inhibitors.

Three-Dimensional Configurations

The structure coordinates generated for S. aureus pdf or the S. aureus pdf/ligand complex or one of its active sites shown in Table 1 define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the three-dimensional configuration of points derived from the structure coordinates of at least a portion of an S. aureus pdf molecule or molecular complex, as shown in Table 1, as well as structurally equivalent configurations, as described below. Preferably, the three-dimensional configuration includes points derived from structure coordinates representing the locations of a plurality of the amino acids defining the S. aureus pdf active site. In one embodiment, the three-dimensional configuration includes points derived from structure coordinates representing the locations the backbone atoms of a plurality of amino acids defining the S. aureus pdf active site, preferably Gly58, Gly60, Leu61, Gln65, Glu109, Gly110, Cys111, Leu112, Ile150, His154, Glu155, and His158; and more preferably Arg56, Ser57, Gly58, Val59, Gly60, Leu61, Gln65, Leu105, Pro106, Thr107, Gly108, Glu109, Gly110, Cys111, Leu112, Asn117, Tyr147, Ile150, Val151, His154, Glu155, and His158. In another embodiment, the three-dimensional configuration includes points derived from structure coordinates representing the locations of the side chain and the backbone atoms (other than hydrogens) of a plurality of the amino acids defining the S. aureus pdf active site, preferably Gly58, Gly60, Leu61, Gln65, Glu109, Gly110, Cys111, Leu112, Ile150, His154, Glu155, and His158; and more preferably Arg56, Ser57, Gly58, Val59, Gly60, Leu61, Gln65, Leu105, Pro106, Thr107, Gly108, Glu109, Gly110, Cys111, Leu112, Asn117, Tyr147, Ile150, Val151, His154, Glu155, and His158.

Likewise, the invention also includes the three-dimensional configuration of points derived from structure coordinates of molecules or molecular complexes that are structurally homologous to S. aureus pdf, as well as structurally equivalent configurations. Structurally homologous molecules or molecular complexes are defined below. Advantageously, structurally homologous molecules can be identified using the structure coordinates of S. aureus pdf (Table 1) according to a method of the invention.

The configurations of points in space derived from structure coordinates according to the invention can be visualized as, for example, a holographic image, a stereodiagram, a model or a computer-displayed image, and the invention thus includes such images, diagrams or models.

Structurally Equivalent Crystal Structures

Various computational analyses can be used to determine whether a molecule or the active site portion thereof is "structurally equivalent," defined in terms of its three-dimensional structure, to all or part of S. aureus pdf or its active sites. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, C$\alpha$, C, and O) for all conserved residues between the two structures being compared. A conserved residue is defined as a residue that is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or active site thereof, or any portion thereof, that has a root mean square deviation of conserved residue backbone atoms (N, C$\alpha$, C, O) of less than about 1.4 Å, when superimposed on the relevant backbone atoms described by the reference structure coordinates listed in Table 1, is considered "structurally equivalent" to the reference molecule. That is to say, the crystal structures of those portions of the two molecules are substantially identical, within acceptable error. Particularly preferred structurally equivalent molecules or molecular complexes are those that are defined by the entire set of structure coordinates in Table 1, ± a root mean square deviation from the conserved backbone atoms of those amino acids of not more than 1.4 Å. More preferably, the root mean square deviation is less than about 0.8 Å, and preferably less than about 0.35 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of S. aureus pdf or an active site portion thereof, as defined by the structure coordinates of S. aureus pdf described herein.

Machine Readable Storage Media

Transformation of the structure coordinates for all or a portion of S. aureus pdf or the S. aureus pdf/ligand complex or one of its active sites, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium including a data storage material encoded with machine readable data which, when using a machine programmed with instructions for using said data, displays a graphical three-dimensional representation of any of the molecule or molecular complexes of this invention that have been described above. In a preferred embodiment, the machine-readable data storage medium includes a data storage material encoded with machine readable data which, when using a machine programmed with instructions for using said data, displays a graphical three-dimensional representation of a molecule or molecular complex including all or any parts of an S. aureus pdf active site or an S. aureus pdf-like active site, as defined above. In another preferred embodiment, the machine-readable data storage medium displays a graphical three-dimensional representation of a molecule or molecular complex defined by the structure coordinates of all of the amino acids in Table 1, ± a root mean square deviation from the backbone atoms of said amino acids of not more than 0.8 Å.

In an alternative embodiment, the machine-readable data storage medium includes a data storage material encoded with a first set of machine readable data which includes the Fourier transform of the structure coordinates set forth in Table 1, and which, when using a machine programmed with instructions for using said data, can be combined with a second set of machine readable data including the x-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid cyrstal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Structurally Homologous Molecules, Molecular Complexes, and Crystal Structures

The structure coordinates set forth in Table 1 can be used to aid in obtaining structural information about another crystallized molecule or molecular complex. A "molecular complex" means a protein in covalent or non-covalent association with a chemical entity or compound. The method of the invention allows determination of at least a portion of the three-dimensional structure of molecules or molecular complexes which contain one or more structural features that are similar to structural features of *S. aureus* pdf. These molecules are referred to herein as "structurally homologous" to *S. aureus* pdf. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., *FEMS Microbiol Lett.*, 174:247–50 (1999), and available on the world wide web at ncbi.nlm.nih.gov/gorf/b12.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with the amino acid sequence of *S. aureus* pdf (SEQ ID NO:12). More preferably, a protein that is structurally homologous to *S. aureus* pdf includes at least one contiguous stretch of at least 50 amino acids that shares at least 80% amino acid sequence identity with the analogous portion of *S. aureus* pdf. Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown including the steps of:

(a) crystallizing the molecule or molecular complex of unknown structure;

(b) generating an x-ray diffraction pattern from said crystallized molecule or molecular complex; and (c) applying at least a portion of the structure coordinates set forth in Table 1 to the x-ray diffraction pattern to generate a three-dimensional electron density map of the molecule or molecular complex whose structure is unknown.

By using molecular replacement, all or part of the structure coordinates of *S. aureus* pdf or the *S. aureus* pdf/ligand complex as provided by this invention (and set forth in Table 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of *S. aureus* pdf or the *S. aureus* pdf/ligand complex according to Table 1 within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions," in *Meth. Enzymol.*, 115:55–77 (1985); M. G. Rossman, ed., "The Molecular Replacement Method," *Int. Sci. Rev. Ser.*, No. 13, Gordon & Breach, New York (1972)).

Structural information about a portion of any crystallized molecule or molecular complex that is sufficiently structurally homologous to a portion of *S. aureus* pdf can be resolved by this method. In addition to a molecule that shares one or more structural features with *S. aureus* pdf as described above, a molecule that has similar bioactivity, such as the same catalytic activity, substrate specificity or ligand binding activity as *S. aureus* pdf, may also be sufficiently structurally homologous to *S. aureus* pdf to permit use of the structure coordinates of *S. aureus* pdf to solve its crystal structure.

In a preferred embodiment, the method of molecular replacement is utilized to obtain structural information about a molecule or molecular complex, wherein the molecule or molecular complex includes at least one *S. aureus* pdf subunit or homolog. A "subunit" of *S. aureus* pdf is an *S. aureus* pdf molecule that has been truncated at the N-terminus or the C-terminus, or both. In the context of the present invention, a "homolog" of *S. aureus* pdf is a protein that contains one or more amino acid substitutions, deletions, additions, or rearrangements with respect to the amino acid sequence of *S. aureus* pdf, but that, when folded into its native conformation, exhibits or is reasonably expected to exhibit at least a portion of the tertiary (three-dimensional) structure of *S. aureus* pdf. For example, structurally homologous molecules can contain deletions or additions of one or more contiguous or noncontiguous amino acids, such as a loop or a domain. Structurally homologous molecules also include "modified" *S. aureus* pdf molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A heavy atom derivative of *S. aureus* pdf is also included as an *S. aureus* pdf homolog. The term "heavy atom derivative" refers to derivatives of *S. aureus* pdf produced by chemically modifying a crystal of *S. aureus* pdf. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (T. L. Blundell and N. L. Johnson, *Protein Crystallography*, Academic Press (1976)).

Because *S. aureus* pdf can crystallize in more than one crystal form, the structure coordinates of *S. aureus* pdf as provided by this invention are particularly useful in solving the structure of other crystal forms of *S. aureus* pdf or *S. aureus* pdf complexes.

The structure coordinates of *S. aureus* pdf in Table 1 are also particularly useful to solve the structure of crystals of *S. aureus* pdf, *S. aureus* pdf mutants or *S. aureus* pdf homologs co-complexed with a variety of chemical entities. This approach enables the determination of the optimal sites for interaction between chemical entities, including candidate *S. aureus* pdf modifiers and *S. aureus* pdf. Potential sites for modification within the various binding site of the molecule can also be identified. This information provides an additional tool for determining the most efficient binding interactions, for example, increased hydrophobic interactions, between *S. aureus* pdf and a chemical entity. For example, high resolution x-ray diffraction data collected from crystals exposed to different types of solvent allows the determination of where each type of solvent molecule resides. Small molecules that bind tightly to those sites can then be designed and synthesized and tested for their potential modification of *S. aureus* pdf.

All of the complexes referred to above may be studied using well-known x-ray diffraction techniques and may be refined versus x-ray data to an R value of about 0.20 or less using computer software, such as X-PLOR (Yale University, (1992), distributed by Molecular Simulations, Inc.; see, e.g., Blundell & Johnson, supra; *Meth. Enzymol.*, Vol. 114 & 115, H. W. Wyckoff et al., eds., Academic Press (1985)). This information may thus be used to optimize known modifiers of *S. aureus* pdf activity, and more importantly, to design new modifiers of *S. aureus* pdf activity.

The invention also includes the unique three-dimensional configuration defined by a set of points defined by the structure coordinates for a molecule or molecular complex structurally homologous to *S. aureus* pdf as determined using the method of the present invention, structurally equivalent configurations, and magnetic storage media including such set of structure coordinates.

Further, the invention includes structurally homologous molecules as identified using the method of the invention.

Homology Modeling

Using homology modeling, a computer model of an *S. aureus* pdf homolog can be built or refined without crystallizing the homolog. First, a preliminary model of the *S. aureus* pdf homolog is created by sequence alignment with *S. aureus* pdf, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. Where the *S. aureus* pdf homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement including molecular dynamics calculations.

Rational Drug Design

Computational techniques can be used to screen, identify, select and design chemical entities capable of associating with *S. aureus* pdf or structurally homologous molecules.

Knowledge of the structure coordinates for S. aureus pdf permits the design and/or identification of synthetic compounds and/or other molecules which have a shape complementary to the conformation of the S. aureus pdf binding site. In particular, computational techniques can be used to identify or design chemical entities that are potential modifiers of *S. aureus* pdf activity, such as inhibitors, agonists and antagonists, that associate with an *S. aureus* pdf active site or an *S. aureus* pdf-like active site. Potential modifiers may bind to or interfere with all or a portion of the active site of *S. aureus* pdf, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block *S. aureus* pdf activity and, thus, block bacterial growth. Structure-activity data for analogs of ligands that bind to or interfere with *S. aureus* pdf or *S. aureus* pdf-like active sites can also be obtained computationally.

The term "chemical entity," as used herein, refers to chemical compounds, complexes of two or more chemical compounds, and fragments of such compounds or complexes. Chemical entities that are determined to associate with *S. aureus* pdf are potential drug candidates. Data stored in a machine-readable storage medium that displays a graphical three-dimensional representation of the structure of *S. aureus* pdf or a structurally homologous molecule, as identified herein, or portions thereof may thus be advantageously used for drug discovery. The structure coordinates of the chemical entity are used to generate a three-dimensional image that can be computationally fit to the three-dimensional image of *S. aureus* pdf or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with *S. aureus* pdf or a structurally homologous molecule, particularly with an *S. aureus* pdf active site or *S. aureus* pdf-like active site. The method of drug design thus includes computationally evaluating the potential of a selected chemical entity to associate with any of the molecules or molecular complexes set forth above. This method includes the steps of: (a) employing computational means to perform a fitting operation between the selected chemical entity and a active site of the molecule or molecular complex; and (b) analyzing the results of said fitting operation to quantify the association between the chemical entity and the active site.

In another embodiment, the method of drug design involves computer-assisted design of chemical entities that associate with *S. aureus* pdf, its homologs, or portions thereof. Chemical entities can be designed in a step-wise fashion, one fragment at a time, or may be designed as a whole or "de novo."

To be a viable drug candidate, the chemical entity identified or designed according to the method must be capable of structurally associating with at least part of an *S. aureus* pdf or *S. aureus* pdf-like active sites, and must be able, sterically and energetically, to assume a conformation that allows it to associate with the *S. aureus* pdf or *S. aureus* pdf-like active site. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the active site, and the spacing between various functional groups of an entity that directly interact with the *S. aureus* pdf-like active site or homologs thereof.

Optionally, the potential binding of a chemical entity to an *S. aureus* pdf or *S. aureus* pdf-like active site is analyzed using computer modeling techniques prior to the actual synthesis and testing of the chemical entity. If these computational experiments suggest insufficient interaction and association between it and the *S. aureus* pdf or *S. aureus* pdf-like active site, testing of the entity is obviated. However, if computer modeling indicates a strong interaction, the molecule may then be synthesized and tested for its ability to bind to or interfere with an *S. aureus* pdf or *S. aureus* pdf-like active site. Binding assays to determine if a compound actually binds to *S. aureus* pdf can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One skilled in the art may use one of several methods to screen chemical entities or fragments for their ability to associate with an *S. aureus* pdf or *S. aureus* pdf-like active site. This process may begin by visual inspection of, for example, an *S. aureus* pdf or *S. aureus* pdf-like active site on the computer screen based on the *S. aureus* pdf structure coordinates in Table 1 or other coordinates which define a similar shape generated from the machine-readable storage medium. Selected fragments or chemical entities may then be positioned in a variety of orientations, or docked, within the active site. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (P. J. Goodford, *J. Med. Chem.*, 28:849–57 (1985); available from Oxford University, Oxford, UK); MCSS (A. Miranker et al., *Proteins: Struct. Funct. Gen.*, 11:29–34 (1991); available from Molecular Simulations, San Diego, Calif.); AUTODOCK (D. S. Goodsell et al., *Proteins: Struct. Funct. Genet.*, 8:195–202 (1990); available from Scripps Research Institute, La Jolla, Calif.); and DOCK (I. D. Kuntz et al., *J. Mol. Biol.*, 161:269–88 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of *S. aureus* pdf. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (P. A. Bartlett et al., in *Molecular Recognition in Chemical and Biological Problems*, Special Publ., Royal Chem. Soc., 78:182–96 (1989); G. Lauri et al., *J. Comput. Aided Mol. Des.,* 8:51–66 (1994); available from the University of California, Berkeley, Calif.); 3D database systems such as ISIS (available from MDL Information Systems, San Leandro, Calif.; reviewed in Y. C. Martin, *J. Med. Chem.* 35:2145–54 (1992)); and HOOK (M. B. Eisen et al., *Proteins: Struc., Funct., Genet.,* 19:199–221 (1994); available from Molecular Simulations, San Diego, Calif.).

S. aureus pdf binding compounds may be designed "de novo" using either an empty binding site or optionally including some portion(s) of a known modifier(s). There are many de novo ligand design methods including, without limitation, LUDI (H.-J. Bohm, *J. Comp. Aid. Molec. Design.,* 6:61–78 (1992); available from Molecular Simulations Inc., San Diego, Calif.); LEGEND (Y. Nishibata et al., *Tetrahedron,* 47:8985 (1991); available from Molecular Simulations Inc., San Diego, Calif.); LeapFrog (available from Tripos Associates, St. Louis, Mo.); and SPROUT (V. Gillet et al., *J. Comput. Aided Mol. Design,* 7:127–53 (1993); available from the University of Leeds, UK).

Once a compound has been designed or selected by the above methods, the efficiency with which that entity may bind to or interfere with an *S. aureus* pdf or *S. aureus* pdf-like active site may be tested and optimized by computational evaluation. For example, an effective *S. aureus* pdf or *S. aureus* pdf-like active site modifier must preferably demonstrate a relatively small difference in energy between its bound and free states (i.e., a small deformation energy of binding). Thus, the most efficient *S. aureus* pdf or *S. aureus* pdf-like active site modifiers should preferably be designed with a deformation energy of binding of not greater than about 10 kcal/mole; more preferably, not greater than 7 kcal/mole. *S. aureus* pdf or *S. aureus* pdf-like active site modifiers may interact with the active site in more than one conformation that is similar in overall binding energy. In those cases, the deformation energy of binding is taken to be the difference between the energy of the free entity and the average energy of the conformations observed when the modifier binds to the protein.

An entity designed or selected as binding to or interfering with an *S. aureus* pdf or *S. aureus* pdf-like active site may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. (1995)); AMBER, version 4.1 (P. A. Kollman, University of California at San Francisco, (1995)); QUANTA/CHARMM (Molecular Simulations, Inc., San Diego, Calif. (1995)); Insight II/Discover (Molecular Simulations, Inc., San Diego, Calif. (1995)); DelPhi (Molecular Simulations, Inc., San Diego, Calif. (1995)); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach encompassed by this invention is the computational screening of small molecule databases for chemical entities or compounds that can bind in whole, or in part, to a *S. aureus* pdf or *S. aureus* pdf-like active site. In this screening, the quality of fit of such entities to the binding site may be judged either by shape complementarity or by estimated interaction energy (E. C. Meng et al., *J. Comp. Chem.,* 13:505–24 (1992)).

This invention also enables the development of chemical entities that can isomerize to short-lived reaction intermediates in the chemical reaction of a substrate or other compound that binds to or with *S. aureus* pdf. Time-dependent analysis of structural changes in *S. aureus* pdf during its interaction with other molecules is carried out. The reaction intermediates of *S. aureus* pdf can also be deduced from the reaction product in co-complex with *S. aureus* pdf. Such information is useful to design improved analogs of known modifiers of *S. aureus* pdf activity or to design novel classes of modifiers based on the reaction intermediates of the *S. aureus* pdf and modifier co-complex. This provides a novel route for designing *S. aureus* pdf modifiers with both high specificity and stability.

Yet another approach to rational drug design involves probing the *S. aureus* pdf crystal of the invention with molecules including a variety of different functional groups to determine optimal sites for interaction between candidate *S. aureus* pdf modifiers and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their hepes protease inhibitor activity (J. Travis, *Science,* 262:1374 (1993)).

In a related approach, iterative drug design is used to identify modifiers of *S. aureus* pdf activity. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three dimensional structure of the complex, and comparing the associations between the new protein/compound complex and previously solved protein/compound complexes. By observing how changes in the compound affected the protein/compound associations, these associations may be optimized.

Pharmaceutical Compositions

Pharmaceutical compositions of this invention include a potential modifier of *S. aureus* pdf activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intra-articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the S. aureus pdf inhibitory compounds described herein are useful for the prevention and treatment of S. aureus pdf mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In order that this invention be more fully understood, the following examples are set forth. These examples are for the purpose of illustration only and are not to be construed as limiting the scope of the invention in any way.

EXAMPLES

Example 1

Analysis of the Structure of S. aureus pdf

Cloning and Expression

The plasmid containing the pdf insert was purified and used to transform a competent strain of E. coli JM109. This cDNA clone used for protein expression and purification (R127K H185Q, highlighted in FIG. 3) contained two mutations. The second mutation is confirmed to be in the HIS6 tag (near the c-terminus) and has no effect on Km or Kcat. The gene encodes a total of 189 residues including a c-terminal hexahis tag (SEQ ID NO:12).

The pdf protein was expressed using LB with ampicillin (100 mg/L) in both the seed and production media. LB was prepared using Bacto-tryptone (10 g), Bacto yeast (5 g), and NaCl (5 g) added per L of deioninzed water. The pH of the media was adjusted to 7.5 before sterilization with KOH. The LB broth was auotclaved for 20 minutes in 100 ml volumes in 500 ml wide mouth fermentation flasks. Ampicillin was filter sterilized and added just before innoculation. The 100 ml seed stock fermentations were carried out in 500 ml wide mouth flasks and were innoculated from agar cultures and were incubated overnight at 37° C. with agitation at 200 revolutions per minute (rpm). The seed fermentations were used to inoculate at 2% the 100 ml production fermentations which were also carried out in 500 ml wide mouth flasks. These fermentations were incubated with agitation at 200 rpm for slightly longer than 2 hours and were then induced (OD 660 nm reached 0.6). IPTG was added to a final concentration of 0.4 mM. The induced fermentations were continued for an additional 3.5 hours until the OD reached 3.0. Multiple fermentations produced a final harvest of 4–6 liters for purification.

For expression of selenomethionyl-Pdf, M9 glucose was utilized in 100 ml volumes containing ampicillin, thiamin, and PAS trace metal solution at 100 mg, 5 mg and 0.3 ml per liter of deionized water, respectively. Multiple shake flasks were used to attain the desired fermentation volume. Since JM109 is not a methionine auxotroph, incorporation of selenomethionine was accomplished through down regulation of methionine biosynthesis just prior to induction (Van Duyne, Standaert, *J. Mol. Biol.*, 229:105–124 (1993)). The culture was grown in 500 ml wide mouth fermentation flasks at 37° C. with an agitation rate of 200 rpm until A600 reached ca. 0.5 unit. At this point, the following filter sterilized amino acids were added to achieve down-regulation. DL-selenomethione, L-lysine, L-threonine and L-phenylalanine were added to final concentrations of 120 micrograms/ml. L-leucine, L-isoleucine and L-valine were added to final concentrations of 60 micrograms/ml. After 15–20 minutes, protein expression was induced by the addition of filter sterilized IPTG added to a final concentration of 0.4 mM. Growth of the culture was continued as described for an additional 3 hours when A600 reached ca. 2 units. Cells were then harvested by centrifugation and stored at −80° C.

Purification

Figure 4:
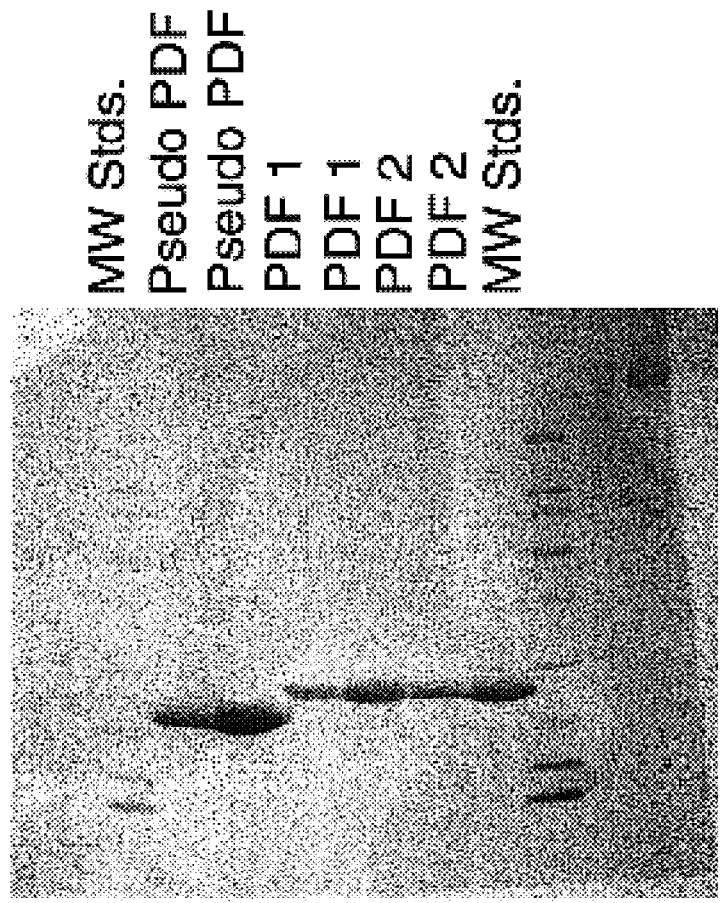
FIG. 4 is a photograph illustrating 4–20% SDS PAGE gel of pseudo pdf, pdf1, and further purified pdf2.

Cell paste from a two liter *E.coli* fermentation expressing *S.aureus* pdf was lysed in 50 mM Tris-HCl pH=8.0 with lysozyme dissolved at 1 mg/ml. The suspension sat on ice for 10 minutes and large strand DNA was broken by repeatedly shearing with a syringe and 19 gauge Needle. Cell extract was collected and centrifuged at 20500 rpm for 40–45 minutes at 5° C. Ni-NTA resin from Qiagen was equilibrated in lysis buffer (without lysozyme) and stirred into the cell extract. The suspension was poured into a column, washed expensively with lysis buffer and pdf was eluted with lysis buffer containing 200 mM imidazole. This protein designated as pdf1 was used for the first crystallization efforts, but required further purification (FIG. 4).

The eluate from the nickel column was concentrated by ultrafiltration with an Amicon stirred cell under nitrogen at room temperature. Two forms of pdf were resolved by anionic (Q fast flow, Pharmacia) exchange chromatography (without baseline resolution) as follows. A concentrated sample was injected onto a 1 mL column equilibrated with 25 mM Tris-HCl, pH=8.0. Proteins were resolved with a linear gradient of NaCl. The two forms of pdf were collected separately for further analysis. No differences in SDS-PAGE mobility or purity were observed. The first fraction had optimal activity while the second fraction had much less specific activity. Protein eluted in the early fraction of the gradient was collected and further concentrated in a stirred cell to the desired volume. Further purified pdf is referred to as pdf2, and improved purification is verified by Isoelectric focussing. Pdf was either delivered for crystallization experiments at this time, or was mixed with 50% glycerol and stored at −20° C. Enzyme assays have demonstrated that pdf is stable for over one year when stored in 50% glycerol at −20° C.

Selenomethionine pdf was purified for crystallization efforts as described above with the inclusion of 5 mM BME to reduce the chance of selenomethionine oxidation.

Protein Preparation

Protein was delivered immediately following concentration of peak material from the anion exchange column. The buffer contained 25 mM Tris pH=8.0 and approximately 50 mM NaCl. Protein was adjusted to 30 mg/ml and exchanged into buffer containing 25 mM Tris pH=8.0. Later batches of protein were received at a protein concentration of 60 mg/ml. This protein was diluted in half with water and frozen immediately in 50 microliter aliquots for later experiments.

Crystallization of *S. aureus* pdf

The first batch of pdf2 was received for crystallization. Crystallization experiments began with commercially available, random sparse matrix screens. Drops of 1 µL protein and 1 µL well solutions were set up in hanging drop vapor diffusion experiments at room temperature. Crystals grew in one week from 4 separate well conditions 6,15,18 and 22 of Hampton Crystal Screen I (Jancarik et al., *J. Appl. Cryst.*, 24:409–11 (1991)). Follow-up grid screens were simultaneously set up to optimize each crystallization condition and are described below.

Hampton Research Crystal Screen I, #6

Hampton Screen I, condition 6 contains 30% PEG 4000, 0.2M $MgCl_2$ and 0.1M Tris pH=8.5. Original crystals grew as long thin needle clusters. Sitting drop vapor diffusion experiments were set up by mixing 2 microliters pdf+2 microliters reservoir solution. Crystals were optimized through a series of grid screens varying both PEG 4000 and $MgCl_2$ concentrations. Results from these screens produced larger rod crystals.

Micro-seeding was utilized in an attempt to grow individual crystals. Seed stocks were made by breaking off a large rod crystal and crushing it in 10 microliters of matching well solution. Serial dilutions of seed stocks were made to $10^{-4}$. Freshly mixed drops of protein and well solution containing 0.1M Tris pH=8.5, 0.075M $MgCl_2$ and varying amounts of PEG 4000 were seeded at setup with a cat whisker by successively streaking the whisker across one row. Single, chunky crystals grew within two weeks up to 0.35×0.35×0.7 micrometer. Large crystals often contained a channel down the middle of the crystal. Crystals were successfully stabilized and slowly transferred into a cryo-preservation solution containing 25% PEG 4000, 0.1M Tris pH=8.5, 0.1M $MgCl_2$ and 25% glycerol. Crystals were frozen in liquid nitrogen for cryogenic data collection.

Hampton Research Crystal Screen I, #15

Condition #15 of Crystal Screen I was the second solution to produce crystals in the original screens. This solution contains 30% PEG 8000, 0.2M ammonium sulfate (A/S) and 0.1M Cacodylic acid pH=6.5. The original hit contained twinned crystalline rods that spread throughout the drop. The crystals were improved by varying both PEG 8000 and ammonium sulfate. Crystals improved significantly through micro-seeding. Crystals could be easily transferred to stabilization solution and slowly soaked into cryo-protective solution containing 22% PEG 8000, 0.2M ammonium sulfate, 0.1M cacodylic acid pH=6.5 and 25% glycerol for freezing.

Hampton Research Crystal Screen I, #18

A third solution to yield crystals was condition #18 of Crystal Screen I. The solution is 20% PEG 8000, 0.1 m Na cacodylate pH=6.5 and 0.2M Mg acetate. Crystals grew as small rods that were very difficult to optimize. Seeding enabled the growth of a few large crystals, but crystals were very fragile. In many cases, crystals could not be stabilized without major crystal cracking. Despite these difficulties, a couple crystals were successfully soaked into cryo-solution containing 20% PEG 8000, 0.1 M NaCacodylate pH=6.5 and 0.2M MgAcetate and 25% glycerol and frozen for data collection.

Hampton Research Crystal Screen I, #22

Crystals also appeared in condition #22 which contains 30% PEG 4000, 0.1M Tris pH=8.5 and 0.2M sodium acetate. Crystals also grew as rod clusters and were optimized as described above for condition #6. Tweaking of the PEG 400 and Na acetate as well as micro-seeding produced large single rods grown from the bridge. Crystals were slowly soaked into cryo-solution of 0.3M Na acetate, 24% PEG 4000, 0.1M Tris pH=8.5 and 25% glycerol. Crystals diffracted well to 2.0 Å.

Selenomethionine pdf

Se-methionine pdf was prepared and initial crystallization experiments were set up in each of the four conditions as described above. An additional 5 mM BME was added to the reservoir solutions to reduce the chance of oxidation. Crystals from condition #6 were optimized through micro-seeding and produced sizable crystals. Crystals were prepared for low temperature data collection.

Data Collection, Space Group Determination

A crystal was grown from 28% PEG 8000, 0.1M cacodylic acid pH=6.5 and 0.1M ammonium sulfate and measured 0.1×0.1×0.5 micrometer. This crystal was the result of the follow up experiments from the Hampton I #15 hits. The crystal was frozen as described above for low temperature data collection. Data was collected on a single Hi Star at a detector distance of 18 cm and a temperature of 100° K. Frames of 300 seconds, 0.25° omega oscillation, and 2θ=15 were collected. Data was not processed because the crystal appeared obviously twinned.

Another crystal was grown from 16% PEG 8000, 0.1M Cacodylic Acid pH=6.5 and 0.4M Mg Acetate. This crystal was the result of the follow up experiments from the Hampton I #18 hits. The crystal was frozen and data was collected on the APS 17-ID beamline. The crystal diffracted to around 1.9 Å and about 400 frames of 0.5 degree oscillation data were collected (Table 5). The space group is $C222_1$ with unit cell parameters of a=94.296 Å, b=120.85 Å, c=47.88 Å, and $\alpha=\beta=\gamma=90°$. Data collection ended since we were at the end of the run and the crystal was recovered at APS and refrozen for additional data collection. Data collection was continued on this crystal. Data was collected on a single Hi Star at detector distance of 12 cm and 300 seconds per frame. The 2θ angle was set to 15° with an omega oscillation of 0.25°. Several water flow problems were encountered during data collection. This data was complete to around 2.7 Å (100% observed) with the I/sigma dropping below 2.0 for the higher resolution data. This data was not used for calculations. Molecular replacement was attempted using this data, but was unsuccessful.

A Se-methionine crystal was grown from 22.5% PEG 4000, 0.1M Tris pH=8.5 and 0.075M $MgCl_2$. This crystal was the result of the follow up experiments from the Hampton I #6 hits. Data was collected on a dual Hi Star at 12 cm and 100° K. Each frame oscillated 0.25° omega for 200 seconds at 2θ=−25°. Data collection statistics are summarized in Table 6. The space group is $C222_1$ with unit cell parameters of a=94.469 Å, b=121.965 Å, c=47.58 Å, and $\alpha=\beta=\gamma=90°$. This crystal diffracted to around 2.0 Å resolution. This data set was used for molecular replacement studies, but these also failed to produce a good solution. This data suggested that a good data set could be obtained from these Se-Methionine crystals at APS.

Preliminary co-crystallization experiments began in an attempt to obtain a pdf complex with several leads as determined from screens. A crystal was grown in the presence of 10% DMSO and 2 mM of a potential inhibitor as well as the reservoir solution containing 20% PEG 4000, 0.1M Tris pH=8.5 and 0.1M $MgCl_2$. This crystal was the result of the follow up experiments from the Hampton I #6 hits. The crystal measured 0.28×0.28×0.98 micrometer and was frozen for low temperature data collection. Data was collected on a dual Hi Star at 100° K. The detector distance was 12 cm and 2θ=30°. Each frame of 0.25° omega oscillation was exposed for 200 seconds. The crystal diffracted to 1.9 Å and was of the $C222_1$ space group with unit cell parameters of a=94.95 Å, b=122.08 Å, c=47.73 Å, and $\alpha=\beta=\gamma 90°$. Data statistics are summarized in Table 7. This data was used for refinement after the pdf structure was solved by MAD phasing, but a bound inhibitor was not observed.

Additional Se-methionine crystals were prepared for MAD data collection at APS. A crystal grew from 19% PEG 4000, 0.075M MgCl$_2$ and 0.1 m Tris pH=8.5. This crystal was the result of the follow up experiments from the Hampton I #6 hits. A total of 3 data sets were collected on the 17-ID beamline at APS. The crystal to detector distance was 15 cm, 2θ=0 and each frame of 0.5° was exposed for 0.5 seconds. The ring current was 96.4 mA. A low data set was collected at a low λ=1.03321, an edge data set was collected at the adsorption edge of λ=0.0.97939, and a peak data set was collected at λ=0.97928. Data collection statistics are summarized in Table 8. The space group is C222$_1$ with unit cell parameters of a=94.113 Å, b=121.873 Å, c=47.579 Å, and α=β=γ=90°.

TABLE 5

Data collection statistics.

| Å | Obs | Theory | % | Redund | Rsym Pairs | % | Rshell | % | 2s |
|---|---|---|---|---|---|---|---|---|---|
| to 4.090 | 2042 | 2343 | 87.15 | 3.86 | 0.065 | 1863 | 79.51 | 0.065 | 85.08 | 2.9 |
| to 3.247 | 4094 | 4584 | 89.31 | 3.99 | 0.067 | 3737 | 81.52 | 0.069 | 62.43 | 4.1 |
| to 2.837 | 6182 | 6780 | 91.18 | 4.07 | 0.067 | 5683 | 83.82 | 0.067 | 42.23 | 5.8 |
| to 2.578 | 8269 | 8975 | 92.13 | 4.11 | 0.069 | 7634 | 85.06 | 0.079 | 26.72 | 7.8 |
| to 2.393 | 10326 | 11156 | 92.56 | 4.13 | 0.071 | 9571 | 85.79 | 0.093 | 21.02 | 11.4 |
| to 2.252 | 12312 | 13339 | 92.30 | 4.08 | 0.074 | 11360 | 85.16 | 0.114 | 17.26 | 12.4 |
| to 2.139 | 14308 | 15515 | 92.22 | 3.96 | 0.077 | 13141 | 84.70 | 0.126 | 14.22 | 15.7 |
| to 2.046 | 16170 | 17685 | 91.43 | 3.82 | 0.079 | 14655 | 82.87 | 0.146 | 12.01 | 18.3 |
| to 1.967 | 17759 | 19839 | 89.52 | 3.70 | 0.081 | 15709 | 79.18 | 0.195 | 8.90 | 22.9 |
| to 1.899 | 19024 | 22028 | 86.36 | 3.60 | 0.083 | 16453 | 74.69 | 0.242 | 6.89 | 28.1 |

TABLE 6

Data collection statistics for data with I/sigma greater than 2.

| Resolution Å | Ref Possible | Ref Observed | observations | R-factor | I/sigma |
|---|---|---|---|---|---|
| 3.76 | 3005 | 2791 | 21889 | 8.88 | 58.19 |
| 2.98 | 2871 | 2629 | 23125 | 9.73 | 43.57 |
| 2.61 | 2852 | 2453 | 18757 | 14.62 | 22.66 |
| 2.37 | 2843 | 2340 | 11384 | 11.83 | 13.50 |
| 2.20 | 2811 | 2148 | 9136 | 23.25 | 9.48 |
| 2.07 | 2809 | 1427 | 4412 | 15.93 | 6.45 |
|  | 17191 | 13788 | 88703 | 10.29 | 28.55 |

TABLE 7

Data collection statistics for data with I/sigma greater than 2.

| Resolution Å | Ref Possible | Ref Observed | observations | R-factor | I/sigma |
|---|---|---|---|---|---|
| 3.61 | 3392 | 3160 | 21173 | 2.27 | 70.5 |
| 2.87 | 3259 | 3117 | 15625 | 3.99 | 37.7 |
| 2.51 | 3214 | 2881 | 8737 | 6.74 | 16.4 |
| 2.28 | 3201 | 2686 | 6898 | 9.37 | 10.8 |
| 2.11 | 3209 | 2520 | 5961 | 10.51 | 8.87 |
| 2.00 | 3176 | 1945 | 4074 | 11.24 | 6.90 |
|  | 19451 | 16309 | 62468 | 3.70 | 27.7 |

TABLE 8

Data collection statistics.

| | Coverage Statistics | | | | | ... Shell | | | | |
|---|---|---|---|---|---|---|---|---|---|---|
| Angstrms | #Obs | Theory | % Compl | Redund | Rsym | Pairs | % Pairs | Rshell | #Sigma | % < 2 s |
| | | | | | stats low | | | | | |
| to 4.091 | 2265 | 2343 | 96.67 | 4.46 | 0.028 | 2072 | 88.43 | 0.028 | 84.43 | 2.0 |
| to 3.247 | 4503 | 4588 | 98.15 | 4.82 | 0.030 | 4249 | 92.61 | 0.032 | 64.10 | 2.4 |
| to 2.837 | 6720 | 6792 | 98.94 | 5.10 | 0.033 | 6444 | 94.88 | 0.041 | 38.38 | 4.0 |
| to 2.578 | 8925 | 8992 | 99.25 | 5.27 | 0.035 | 8646 | 96.15 | 0.048 | 26.64 | 5.6 |
| to 2.393 | 11131 | 11185 | 99.52 | 5.35 | 0.037 | 10850 | 97.00 | 0.053 | 20.55 | 8.2 |
| to 2.252 | 13312 | 13363 | 99.62 | 5.23 | 0.038 | 12969 | 97.05 | 0.056 | 17.44 | 10.4 |
| to 2.139 | 15489 | 15533 | 99.72 | 5.07 | 0.039 | 14978 | 96.43 | 0.062 | 14.57 | 13.6 |
| to 2.046 | 17604 | 17725 | 99.32 | 4.92 | 0.040 | 16869 | 95.17 | 0.067 | 12.58 | 15.0 |
| to 1.967 | 19626 | 19868 | 98.78 | 4.74 | 0.041 | 18446 | 92.84 | 0.081 | 9.67 | 18.8 |
| to 1.899 | 21519 | 22066 | 97.52 | 4.54 | 0.042 | 19661 | 89.10 | 0.107 | 7.97 | 22.2 |
| | | | | | stats edge | | | | | |
| to 4.091 | 2249 | 2343 | 95.99 | 3.74 | 0.034 | 1577 | 67.31 | 0.034 | 81.38 | 2.1 |
| to 3.247 | 4478 | 4588 | 97.60 | 4.17 | 0.037 | 3455 | 75.31 | 0.039 | 60.12 | 2.6 |
| to 2.837 | 6688 | 6792 | 98.47 | 4.51 | 0.043 | 5468 | 80.51 | 0.061 | 33.75 | 5.2 |
| to 2.578 | 8892 | 8992 | 98.89 | 4.76 | 0.048 | 7550 | 83.96 | 0.081 | 22.55 | 7.3 |
| to 2.393 | 11088 | 11185 | 99.13 | 4.94 | 0.053 | 9682 | 86.56 | 0.095 | 16.88 | 10.6 |
| to 2.252 | 13278 | 13363 | 99.36 | 5.03 | 0.057 | 11842 | 88.62 | 0.101 | 14.05 | 12.9 |
| to 2.139 | 15478 | 15533 | 99.65 | 4.97 | 0.060 | 13963 | 89.89 | 0.107 | 11.68 | 17.4 |
| to 2.046 | 17649 | 17725 | 99.57 | 4.86 | 0.062 | 15967 | 90.08 | 0.113 | 10.17 | 18.8 |
| to 1.967 | 19761 | 19868 | 99.46 | 4.76 | 0.064 | 17876 | 89.97 | 0.129 | 7.54 | 24.6 |
| to 1.899 | 21904 | 22066 | 99.27 | 4.62 | 0.065 | 19621 | 88.92 | 0.152 | 5.87 | 29.9 |
| | | | | | stats peak | | | | | |
| to 4.091 | 2280 | 2343 | 97.31 | 3.60 | 0.038 | 1594 | 68.03 | 0.038 | 81.02 | 2.3 |
| to 3.247 | 4480 | 4588 | 97.65 | 4.04 | 0.040 | 3446 | 75.11 | 0.041 | 59.39 | 3.0 |
| to 2.837 | 6677 | 6792 | 98.31 | 4.41 | 0.046 | 5373 | 79.11 | 0.063 | 33.15 | 5.9 |
| to 2.578 | 8881 | 8992 | 98.77 | 4.67 | 0.051 | 7393 | 82.22 | 0.081 | 22.29 | 7.5 |
| to 2.393 | 11072 | 11185 | 98.99 | 4.87 | 0.056 | 9452 | 84.51 | 0.095 | 16.80 | 10.8 |
| to 2.252 | 13247 | 13363 | 99.13 | 4.97 | 0.060 | 11527 | 86.26 | 0.105 | 13.87 | 13.5 |
| to 2.139 | 15449 | 15533 | 99.46 | 4.92 | 0.063 | 13605 | 87.59 | 0.116 | 11.72 | 17.7 |
| to 2.046 | 17637 | 17725 | 99.50 | 4.81 | 0.066 | 15657 | 88.33 | 0.123 | 10.11 | 19.0 |
| to 1.967 | 19798 | 19868 | 99.65 | 4.70 | 0.069 | 17642 | 88.80 | 0.143 | 7.63 | 24.5 |
| to 1.899 | 22008 | 22066 | 99.74 | 4.56 | 0.071 | 19528 | 88.50 | 0.168 | 6.04 | 29.2 |

Phase Determination and Refinement

The structure of *S.aureus* pdf was determined by multiple anomalous dispersion (MAD) using synchrotron radiation. The MAD data set included data to 1.9 Å resolution. Anomalous difference Patterson maps revealed the expected six selenium sites for a single protein molecule in the asymmetric unit. An excellent well-phased map to 1.9 Å resolution was produced into which the protein model could be easily built. However, XPLOR refinement of this model did not result in a model with an R-factor below 30%. This was difficult to understand since the overall map quality was excellent and there was little remaining difference density unaccounted for. This refinement effort was eventually discontinued in favor of a second data set. The 2.0 Å resolution data from the pdf crystal was used for the refinement of the structure. These data did refine well and a final R-factor of 18.6% for this model with good geometry was obtained (Table 9).

The X-ray data for the MAD phasing of pdf was collected at the Advanced Photon Source and consisted of three separate wavelength experiments centered about the Selenium edge (low, 1.03321 Å; edge, 0.97939 Å; high, 0.97928 Å). Each of the data sets were indexed and integrated separately. The data sets were scaled together using the program SCALEIT in the CCP4 Program Suite (Collaborative Computational Project N4, *Acta Cryst.*, D50:760–63 (1994)). Patterson maps revealed six selenium sites whose locations were determined and refined by direct methods using SHELX (Sheldrick et al., *Acta Cryst.*, B51:423–31 (1995)). Heavy atom refinement and phase calculations were carried out using MLPHARE from CCP4 with all the data from 10 to 1.9 Å resolution. The resulting electron density map was readily interpreted and a model built. A density modified map was also calculated (MLPHARE), but the maps were not very different. Model building was done with the program CHAIN (Sack, *J.Mol.Graphics*, 6:224–25 (1988)) and LORE (Finzel, *Meth.Enzymol.*, 277:230–42 (1997)). Initial refinement was carried out with XPLOR (Brunger AT. X-PLOR version 3.1: Asystem for X-ray crystallography and NMR. New Haven: Yale Univ. Press, (1992)). However, the R-factor failed to fall below 30% after several cycles and with the inclusion of many waters. At that point the refinement of this data set was discontinued in favor of another data set.

TABLE 9

Data collection and phasing statistics

| | λ 1.03321 Å | λ 0.97939 Å | λ 0.97928 Å |
|---|---|---|---|
| Resolution | 1.9 Å | 1.9 Å | 1.9 Å |
| Average redundancy | 4.5 | 4.5 | 4.5 |
| # unique reflections | 21519 | 21904 | 22008 |
| % completeness | 97.5% | 99.3% | 99.7% |
| $R_{sym}^\dagger$ | 0.042 | 0.065 | 0.071 |
| $R_{sym}$ (1.96–1.89 shell) | 0.107 | 0.152 | 0.168 |
| $R_{cullis}$ acentrics | 1.70 (19034 refs) | 0.87 (18878 refs) | 0.57 (18899 refs) |
| $R_{cullis}$ anomalous | 0.98 (19178 refs) | 0.64 (18418 refs) | 0.58 (18679 refs) |
| Phasing Power | | | |
| Centrics | — | 0.70 | 1.83 |
| Acentrics | — | 0.80 | 2.15 |
| Mean FOM | overall | centric | acentric |
| Before solvent flattening | 0.714 (21048 ref) | 0.627 (2014 refs) | 0.724 (19034 refs) |
| After solvent flattening | 0.788 | — | — |

Refinement of the Data Set

This data was used for the further refinement of the native pdf structure. The partially refined model derived from the MAD map was rotated to an arbitrary initial position, stripped of water and cations, and used for molecular replacement (XPLOR). The rotation solutions were filtered with PC-refinement (Brunger, *Acta Crystallogr.*, A46:46–47 (1990)). The highest rotation function peak also resulted in the highest PC-filtered peak (PC=0.194). The position of the rotated monomer was obtained by a translation search (again the highest peak in the map and 15.6 sigma above the mean). The solution obtained was consistent with the position of the molecule in the MAD map and had an initial R-factor of 39.6% for data from 20–2.5 Å resolution (9235 reflections). This structure was further refined with XPLOR positional refinement and waters and a Zinc atom incorporated into the model. The R-factor dropped to 21% with a Free-R-factor of just over 25%. A final cycle of refinement and rebuilding was employed using PROLSQ (Hendrickson et al., "Stereochemically restrained crystallographic least-squares refinement of macromolecule structures" in *Biomolecular Structure, Function and Evolution*, (R. Srinivasan, ed. 43–57) Pergamon Press, Oxford UK (1981)) which resulted in a final R-factor of 18.62% for 16266 reflections, 10–2.0 Å resolution data. The final agreement statistics (Table 10) and Ramachandran plot revealed a well-refined structure and are included below. Additional statistics were generated with PROCHECK (Laskowski et al., *J. Appl. Cryst.*, 26:283–91 (1993)). A comparison of the initial MAD map and the final refined map was produced in CHAIN.

TABLE 10

Final model agreement statistics for PDF data set.

Resolution: 2.00 Angstrom
R-value: 18.62% for 16,266 reflections (2sigma)
Atoms 1725 (305 waters); 1 Zinc
Mean B-factor 15.0 Å$^2$
Final Model rmsd from expected for restraint class:

Distances:

| | |
|---|---|
| 1–2 bonds | 0.018 (0.030) |
| 1–3 bond angle | 0.031 (0.040) |
| 1–4 torsional | 0.029 (0.050) |

TABLE 10-continued

Final model agreement statistics for PDF data set.

| Planes | |
|---|---|
| peptides | 0.016 (0.030) |
| Other | 0.014 (0.030) |
| chiral volumes | 0.204 (0.250) |
| NonBonded | |
| 1–4 | 0.174 (0.300) |
| H-bond | 0.204 (0.300) |
| other | 0.172 (0.300) |
| Thermal | |
| 1–2 mainchain | 1.033 (1.500) |
| 1–3 | 1.676 (3.000) |
| 1–2 sidechain | 2.109 (2.000) |
| 1–3 sidechain | 3.293 (4.000) |

Comparison of *S.aureus* and *E.coli* pdf Structures

The final *S.aureus* pdf and the *E.coli* pdf complex with (S)-2-O—H-phosphonoxy)-L-caproyl-L-leucyl-p-nitroanilide (PCLNA) (Hao et al., *Biochemistry*, 38: 4712–19 (1999)) were compared using SUPERPDB (Finzel, unpublished). FIGS. 6 and 11 were produced with MOLSCRIPT (Kraulis, *J. Appl. Cryst.*, 24:946–50 (1991)) and Raster 3D (Merritt et al., *Acta Cryst.*, D50:869–73 (1994)). FIGS. 8, 9, 12 and 13 were prepared with MOSAIC2. FIGS. 7 and 14 were prepared with CHAIN using PLOT.

The complete disclosure of all patents, patent applications including provisional applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described; many variations will be apparent to one skilled in the art and are intended to be included within the invention defined by the claims.

Sequence Listing Free Text

SEQ ID NO:1 *Staphylococcus aureus* peptide deformylase with C-terminal 6×His tag
SEQ ID NO:2 *Escherichia coli* peptide deformylase
SEQ ID NO:3 *Haemophilis influenzae* peptide deformylase
SEQ ID NO:4 *Bacillus subtilis* peptide deformylase
SEQ ID NO:5 *Mycoplasma pneumoniae* peptide deformylase SEQ ID NO:6 *Staphylococcus aureus* def1 gene (Pseudo pdf)
SEQ ID NO:7 *Staphylococcus aureus* peptide deformylase
SEQ ID NO:8 *Escherichia coli* peptide deformylase
SEQ ID NO:9 Amino Acid Residue
SEQ ID NO:10 Amino Acid Residue
SEQ ID NO:11 Amino Acid Residue

TABLE 1

Structure Coordinates for *S. aureus* pdf

| | | | | | | | | | |
|---|---|---|---|---|---|---|---|---|---|
| CRYST1 | 94.950 | | 122.080 | | 47.730 | 90.00 | 90.00 | 90.00 | |
| SCALE1 | 0.010532 | | 0.000000 | | 0.000000 | | | 0.00000 | |
| SCALE2 | 0.000000 | | 0.008191 | | 0.000000 | | | 0.00000 | |
| SCALE3 | 0.000000 | | 0.000000 | | 0.020951 | | | 0.00000 | |
| ATOM | 1 | N | MET | 1 | 34.916 | 34.289 | 28.962 | 1.00 | 19.94 |
| ATOM | 2 | CA | MET | 1 | 34.532 | 33.707 | 30.269 | 1.00 | 17.68 |
| ATOM | 3 | CB | MET | 1 | 34.906 | 34.864 | 31.043 | 1.00 | 22.02 |
| ATOM | 4 | CG | MET | 1 | 34.249 | 35.660 | 31.315 | 1.00 | 26.50 |
| ATOM | 5 | SD | MET | 1 | 34.946 | 36.841 | 32.629 | 1.00 | 21.74 |
| ATOM | 6 | CE | MET | 1 | 34.539 | 36.320 | 34.127 | 1.00 | 24.64 |
| ATOM | 7 | C | MET | 1 | 33.437 | 33.258 | 30.418 | 1.00 | 14.02 |
| ATOM | 8 | O | MET | 1 | 32.276 | 33.920 | 29.938 | 1.00 | 26.24 |
| ATOM | 9 | N | LEU | 2 | 32.981 | 31.938 | 30.879 | 1.00 | 7.75 |
| ATOM | 10 | CA | LEU | 2 | 31.816 | 31.467 | 31.565 | 1.00 | 8.41 |
| ATOM | 11 | CB | LEU | 2 | 32.031 | 30.005 | 32.023 | 1.00 | 8.48 |
| ATOM | 12 | CG | LEU | 2 | 32.268 | 28.961 | 30.866 | 1.00 | 7.73 |
| ATOM | 13 | CD1 | LEU | 2 | 32.614 | 27.626 | 31.509 | 1.00 | 9.08 |
| ATOM | 14 | CD2 | LEU | 2 | 30.932 | 28.747 | 30.133 | 1.00 | 8.57 |
| ATOM | 15 | C | LEU | 2 | 31.402 | 32.379 | 32.708 | 1.00 | 9.38 |
| ATOM | 16 | O | LEU | 2 | 32.278 | 32.943 | 33.415 | 1.00 | 10.57 |
| ATOM | 17 | N | THR | 3 | 30.099 | 32.656 | 32.839 | 1.00 | 9.70 |
| ATOM | 18 | CA | THR | 3 | 29.624 | 33.466 | 33.943 | 1.00 | 10.89 |
| ATOM | 19 | CB | THR | 3 | 29.238 | 34.900 | 33.661 | 1.00 | 10.34 |
| ATOM | 20 | OG1 | THR | 3 | 28.067 | 34.943 | 32.811 | 1.00 | 13.27 |
| ATOM | 21 | CG2 | THR | 3 | 30.363 | 35.684 | 33.051 | 1.00 | 9.36 |
| ATOM | 22 | C | THR | 3 | 28.428 | 32.714 | 34.511 | 1.00 | 12.61 |
| ATOM | 23 | O | THR | 3 | 28.150 | 31.586 | 34.034 | 1.00 | 12.67 |
| ATOM | 24 | N | MET | 4 | 27.740 | 33.297 | 35.478 | 1.00 | 13.52 |
| ATOM | 25 | CA | MET | 4 | 26.570 | 32.603 | 36.027 | 1.00 | 12.96 |
| ATOM | 26 | CB | MET | 4 | 26.007 | 33.362 | 37.225 | 1.00 | 12.16 |
| ATOM | 27 | CG | MET | 4 | 26.954 | 33.492 | 38.401 | 1.00 | 12.58 |
| ATOM | 28 | SD | MET | 4 | 27.512 | 31.883 | 38.995 | 1.00 | 12.58 |
| ATOM | 29 | CE | MET | 4 | 25.972 | 31.153 | 39.545 | 1.00 | 11.19 |
| ATOM | 30 | C | MET | 4 | 25.497 | 32.343 | 34.975 | 1.00 | 13.01 |
| ATOM | 31 | O | MET | 4 | 24.627 | 31.474 | 35.142 | 1.00 | 11.54 |
| ATOM | 32 | N | LYS | 5 | 25.475 | 33.147 | 33.917 | 1.00 | 13.68 |
| ATOM | 33 | CA | LYS | 5 | 24.490 | 32.976 | 32.902 | 1.00 | 14.22 |
| ATOM | 34 | CB | LYS | 5 | 24.163 | 34.124 | 31.992 | 1.00 | 16.93 |
| ATOM | 35 | CG | LYS | 5 | 25.243 | 34.788 | 31.252 | 1.00 | 18.60 |
| ATOM | 36 | CD | LYS | 5 | 24.807 | 35.647 | 30.112 | 1.00 | 19.21 |
| ATOM | 37 | CE | LYS | 5 | 23.755 | 36.633 | 30.201 | 1.00 | 17.56 |
| ATOM | 38 | NZ | LYS | 5 | 23.653 | 37.497 | 28.989 | 1.00 | 17.28 |
| ATOM | 39 | C | LYS | 5 | 24.684 | 31.690 | 32.119 | 1.00 | 13.07 |
| ATOM | 40 | O | LYS | 5 | 23.720 | 31.241 | 31.521 | 1.00 | 12.87 |
| ATOM | 41 | N | ASP | 6 | 25.880 | 31.127 | 32.131 | 1.00 | 12.68 |
| ATOM | 42 | CA | ASP | 6 | 26.110 | 29.855 | 31.443 | 1.00 | 10.98 |
| ATOM | 43 | CB | ASP | 6 | 27.608 | 29.644 | 31.134 | 1.00 | 11.64 |
| ATOM | 44 | CG | ASP | 6 | 28.053 | 30.725 | 30.147 | 1.00 | 12.48 |
| ATOM | 45 | OD1 | ASP | 6 | 27.837 | 30.487 | 28.933 | 1.00 | 13.27 |
| ATOM | 46 | OD2 | ASP | 6 | 28.505 | 31.815 | 30.591 | 1.00 | 11.62 |
| ATOM | 47 | C | ASP | 6 | 25.640 | 28.730 | 32.353 | 1.00 | 11.50 |
| ATOM | 48 | O | ASP | 6 | 25.445 | 27.605 | 31.881 | 1.00 | 11.74 |
| ATOM | 49 | N | ILE | 7 | 25.501 | 29.000 | 33.628 | 1.00 | 11.13 |
| ATOM | 50 | CA | ILE | 7 | 25.098 | 27.943 | 34.547 | 1.00 | 11.49 |
| ATOM | 51 | CB | ILE | 7 | 25.811 | 28.121 | 35.898 | 1.00 | 11.70 |
| ATOM | 52 | CG1 | ILE | 7 | 27.331 | 27.997 | 35.581 | 1.00 | 11.93 |
| ATOM | 53 | CD1 | ILE | 7 | 28.288 | 28.140 | 36.663 | 1.00 | 12.02 |
| ATOM | 54 | CG2 | ILE | 7 | 25.417 | 27.057 | 36.887 | 1.00 | 11.40 |
| ATOM | 55 | C | ILE | 7 | 23.634 | 27.664 | 34.603 | 1.00 | 11.29 |
| ATOM | 56 | O | ILE | 7 | 22.817 | 28.487 | 34.999 | 1.00 | 12.63 |
| ATOM | 57 | N | ILE | 8 | 23.245 | 26.433 | 34.193 | 1.00 | 10.48 |
| ATOM | 58 | CA | ILE | 8 | 21.856 | 26.026 | 34.213 | 1.00 | 9.51 |
| ATOM | 59 | CB | ILE | 8 | 21.513 | 24.909 | 33.253 | 1.00 | 8.83 |
| ATOM | 60 | CG1 | ILE | 8 | 22.221 | 23.575 | 33.487 | 1.00 | 7.90 |
| ATOM | 61 | CD1 | ILE | 8 | 21.762 | 22.525 | 32.454 | 1.00 | 7.81 |
| ATOM | 62 | CG2 | ILE | 8 | 21.684 | 25.377 | 31.803 | 1.00 | 9.89 |
| ATOM | 63 | C | ILE | 8 | 21.433 | 25.703 | 35.643 | 1.00 | 10.40 |
| ATOM | 64 | O | ILE | 8 | 22.205 | 25.174 | 36.456 | 1.00 | 9.94 |
| ATOM | 65 | N | ARG | 9 | 20.182 | 26.031 | 35.987 | 1.00 | 11.42 |
| ATOM | 66 | CA | ARG | 9 | 19.665 | 25.850 | 37.329 | 1.00 | 12.02 |

TABLE 1-continued

Structure Coordinates for *S. aureus* pdf

| ATOM | 67 | CB | ARG | 9 | 19.009 | 27.157 | 37.828 | 1.00 | 10.73 |
|---|---|---|---|---|---|---|---|---|---|
| ATOM | 68 | CG | ARG | 9 | 19.850 | 28.421 | 37.618 | 1.00 | 11.22 |
| ATOM | 69 | CD | ARG | 9 | 21.253 | 28.290 | 38.166 | 1.00 | 11.70 |
| ATOM | 70 | NE | ARG | 9 | 22.124 | 29.328 | 37.705 | 1.00 | 14.84 |
| ATOM | 71 | CZ | ARG | 9 | 22.235 | 30.599 | 38.010 | 1.00 | 15.66 |
| ATOM | 72 | NH1 | ARG | 9 | 21.529 | 31.122 | 38.991 | 1.00 | 18.52 |
| ATOM | 73 | NH2 | ARG | 9 | 22.902 | 31.393 | 37.188 | 1.00 | 14.81 |
| ATOM | 74 | C | ARG | 9 | 18.764 | 24.658 | 37.504 | 1.00 | 12.31 |
| ATOM | 75 | O | ARG | 9 | 18.267 | 24.036 | 36.555 | 1.00 | 14.42 |
| ATOM | 76 | N | ASP | 10 | 18.518 | 24.283 | 38.736 | 1.00 | 12.74 |
| ATOM | 77 | CA | ASP | 10 | 17.674 | 23.150 | 39.113 | 1.00 | 13.72 |
| ATOM | 78 | CB | ASP | 10 | 17.681 | 22.953 | 40.600 | 1.00 | 14.31 |
| ATOM | 79 | CG | ASP | 10 | 16.924 | 21.758 | 41.104 | 1.00 | 14.46 |
| ATOM | 80 | OD1 | ASP | 10 | 17.107 | 20.628 | 40.640 | 1.00 | 14.86 |
| ATOM | 81 | OD2 | ASP | 10 | 16.146 | 21.966 | 42.029 | 1.00 | 16.72 |
| ATOM | 82 | C | ASP | 10 | 16.285 | 23.236 | 38.506 | 1.00 | 14.81 |
| ATOM | 83 | O | ASP | 10 | 15.531 | 24.212 | 38.663 | 1.00 | 15.66 |
| ATOM | 84 | N | GLY | 11 | 15.932 | 22.174 | 37.772 | 1.00 | 14.39 |
| ATOM | 85 | CA | GLY | 11 | 14.636 | 22.169 | 37.079 | 1.00 | 15.06 |
| ATOM | 86 | C | GLY | 11 | 14.962 | 22.038 | 35.578 | 1.00 | 15.47 |
| ATOM | 87 | O | GLY | 11 | 14.116 | 21.564 | 34.841 | 1.00 | 16.98 |
| ATOM | 88 | N | HIS | 12 | 16.200 | 22.335 | 35.197 | 1.00 | 16.07 |
| ATOM | 89 | CA | HIS | 12 | 16.564 | 22.199 | 33.771 | 1.00 | 15.33 |
| ATOM | 90 | CB | HIS | 12 | 17.798 | 22.984 | 33.422 | 1.00 | 14.11 |
| ATOM | 91 | CG | HIS | 12 | 18.137 | 23.113 | 31.958 | 1.00 | 12.04 |
| ATOM | 92 | ND1 | HIS | 12 | 18.258 | 22.085 | 31.076 | 1.00 | 10.56 |
| ATOM | 93 | CE1 | HIS | 12 | 18.600 | 22.523 | 29.883 | 1.00 | 9.61 |
| ATOM | 94 | NE2 | HIS | 12 | 18.767 | 23.826 | 29.977 | 1.00 | 11.37 |
| ATOM | 95 | CD2 | HIS | 12 | 18.457 | 24.243 | 31.262 | 1.00 | 11.65 |
| ATOM | 96 | C | HIS | 12 | 16.780 | 20.692 | 33.515 | 1.00 | 15.36 |
| ATOM | 97 | O | HIS | 12 | 17.443 | 19.998 | 34.299 | 1.00 | 14.84 |
| ATOM | 98 | N | PRO | 13 | 16.209 | 20.178 | 32.431 | 1.00 | 14.53 |
| ATOM | 99 | CA | PRO | 13 | 16.296 | 18.798 | 32.066 | 1.00 | 14.20 |
| ATOM | 100 | CB | PRO | 13 | 15.436 | 18.664 | 30.843 | 1.00 | 14.95 |
| ATOM | 101 | CG | PRO | 13 | 15.070 | 20.047 | 30.408 | 1.00 | 15.00 |
| ATOM | 102 | CD | PRO | 13 | 15.333 | 20.975 | 31.520 | 1.00 | 14.75 |
| ATOM | 103 | C | PRO | 13 | 17.704 | 18.221 | 31.869 | 1.00 | 13.44 |
| ATOM | 104 | O | PRO | 13 | 17.920 | 17.049 | 32.297 | 1.00 | 13.01 |
| ATOM | 105 | N | THR | 14 | 18.641 | 18.885 | 31.313 | 1.00 | 12.25 |
| ATOM | 106 | CA | THR | 14 | 20.006 | 18.412 | 31.110 | 1.00 | 12.11 |
| ATOM | 107 | CB | THR | 14 | 20.879 | 19.447 | 30.442 | 1.00 | 12.39 |
| ATOM | 108 | OG1 | THR | 14 | 20.324 | 19.783 | 29.186 | 1.00 | 14.02 |
| ATOM | 109 | CG2 | THR | 14 | 22.327 | 19.047 | 30.251 | 1.00 | 11.43 |
| ATOM | 110 | C | THR | 14 | 20.616 | 17.961 | 32.443 | 1.00 | 11.87 |
| ATOM | 111 | O | THR | 14 | 21.340 | 16.974 | 32.439 | 1.00 | 12.53 |
| ATOM | 112 | N | LEU | 15 | 20.236 | 18.589 | 33.544 | 1.00 | 11.35 |
| ATOM | 113 | CA | LEU | 15 | 20.691 | 18.204 | 34.862 | 1.00 | 10.88 |
| ATOM | 114 | CB | LEU | 15 | 20.289 | 19.242 | 35.945 | 1.00 | 9.29 |
| ATOM | 115 | CG | LEU | 15 | 20.941 | 20.618 | 35.797 | 1.00 | 10.23 |
| ATOM | 116 | CD1 | LEU | 15 | 20.421 | 21.579 | 36.861 | 1.00 | 9.66 |
| ATOM | 117 | CD2 | LEU | 15 | 22.486 | 20.500 | 35.940 | 1.00 | 8.87 |
| ATOM | 118 | C | LEU | 15 | 20.276 | 16.823 | 35.350 | 1.00 | 10.52 |
| ATOM | 119 | O | LEU | 15 | 20.887 | 16.276 | 36.276 | 1.00 | 10.57 |
| ATOM | 120 | N | ARG | 16 | 19.281 | 16.212 | 34.728 | 1.00 | 12.62 |
| ATOM | 121 | CA | ARG | 16 | 18.760 | 14.908 | 35.102 | 1.00 | 12.70 |
| ATOM | 122 | CB | ARG | 16 | 17.252 | 15.021 | 35.435 | 1.00 | 11.19 |
| ATOM | 123 | CG | ARG | 16 | 16.965 | 15.901 | 36.689 | 1.00 | 12.05 |
| ATOM | 124 | CD | ARG | 16 | 17.589 | 15.300 | 37.922 | 1.00 | 12.29 |
| ATOM | 125 | NE | ARG | 16 | 17.174 | 15.869 | 39.202 | 1.00 | 14.07 |
| ATOM | 126 | CZ | ARG | 16 | 17.503 | 15.282 | 40.354 | 1.00 | 14.85 |
| ATOM | 127 | NH1 | ARG | 16 | 18.257 | 14.175 | 40.357 | 1.00 | 13.47 |
| ATOM | 128 | NH2 | ARG | 16 | 17.016 | 15.724 | 41.537 | 1.00 | 14.89 |
| ATOM | 129 | C | ARG | 16 | 19.050 | 13.808 | 34.098 | 1.00 | 13.29 |
| ATOM | 130 | O | ARG | 16 | 18.686 | 12.615 | 34.267 | 1.00 | 12.21 |
| ATOM | 131 | N | GLN | 17 | 19.716 | 14.156 | 33.007 | 1.00 | 14.43 |
| ATOM | 132 | CA | GLN | 17 | 20.112 | 13.203 | 31.993 | 1.00 | 14.49 |
| ATOM | 133 | CB | GLN | 17 | 20.423 | 13.917 | 30.676 | 1.00 | 15.50 |
| ATOM | 134 | CG | GLN | 17 | 19.172 | 14.623 | 30.150 | 1.00 | 19.61 |
| ATOM | 135 | CD | GLN | 17 | 19.464 | 15.367 | 28.883 | 1.00 | 22.76 |
| ATOM | 136 | OE1 | GLN | 17 | 20.585 | 15.845 | 28.654 | 1.00 | 25.94 |
| ATOM | 137 | NE2 | GLN | 17 | 18.516 | 15.484 | 27.983 | 1.00 | 25.81 |
| ATOM | 138 | C | GLN | 17 | 21.414 | 12.531 | 32.438 | 1.00 | 14.27 |
| ATOM | 139 | O | GLN | 17 | 22.117 | 12.968 | 33.350 | 1.00 | 13.89 |
| ATOM | 140 | N | LYS | 18 | 21.716 | 11.457 | 31.735 | 1.00 | 14.65 |
| ATOM | 141 | CA | LYS | 18 | 22.963 | 10.724 | 31.984 | 1.00 | 13.90 |
| ATOM | 142 | CB | LYS | 18 | 22.734 | 9.222 | 32.030 | 1.00 | 15.80 |
| ATOM | 143 | CG | LYS | 18 | 24.083 | 8.533 | 32.321 | 1.00 | 19.05 |

TABLE 1-continued

Structure Coordinates for S. aureus pdf

| ATOM | 144 | CD | LYS | 18 | 23.986 | 7.048 | 32.414 | 1.00 | 21.35 |
|---|---|---|---|---|---|---|---|---|---|
| ATOM | 145 | CE | LYS | 18 | 25.337 | 6.413 | 32.686 | 1.00 | 22.45 |
| ATOM | 146 | NZ | LYS | 18 | 25.078 | 4.922 | 32.839 | 1.00 | 26.17 |
| ATOM | 147 | C | LYS | 18 | 23.980 | 11.178 | 30.950 | 1.00 | 12.55 |
| ATOM | 148 | O | LYS | 18 | 23.801 | 10.968 | 29.753 | 1.00 | 14.36 |
| ATOM | 149 | N | ALA | 19 | 25.068 | 11.839 | 31.353 | 1.00 | 10.71 |
| ATOM | 150 | CA | ALA | 19 | 26.065 | 12.355 | 30.478 | 1.00 | 10.46 |
| ATOM | 151 | CB | ALA | 19 | 27.088 | 13.257 | 31.241 | 1.00 | 9.78 |
| ATOM | 152 | C | ALA | 19 | 26.749 | 11.295 | 29.636 | 1.00 | 11.00 |
| ATOM | 153 | O | ALA | 19 | 26.983 | 10.143 | 30.034 | 1.00 | 12.01 |
| ATOM | 154 | N | ALA | 20 | 27.080 | 11.667 | 28.404 | 1.00 | 10.99 |
| ATOM | 155 | CA | ALA | 20 | 27.720 | 10.828 | 27.437 | 1.00 | 9.79 |
| ATOM | 156 | CB | ALA | 20 | 27.497 | 11.492 | 26.021 | 1.00 | 8.56 |
| ATOM | 157 | C | ALA | 20 | 29.232 | 10.755 | 27.581 | 1.00 | 9.39 |
| ATOM | 158 | O | ALA | 20 | 29.876 | 11.797 | 27.803 | 1.00 | 8.57 |
| ATOM | 159 | N | GLU | 21 | 29.758 | 9.569 | 27.411 | 1.00 | 9.74 |
| ATOM | 160 | CA | GLU | 21 | 31.202 | 9.379 | 27.439 | 1.00 | 11.72 |
| ATOM | 161 | CB | GLU | 21 | 31.512 | 7.905 | 27.257 | 1.00 | 17.23 |
| ATOM | 162 | CG | GLU | 21 | 31.202 | 6.871 | 28.231 | 1.00 | 22.07 |
| ATOM | 163 | CD | GLU | 21 | 32.063 | 6.663 | 29.432 | 1.00 | 26.07 |
| ATOM | 164 | OE1 | GLU | 21 | 33.305 | 6.831 | 29.247 | 1.00 | 28.08 |
| ATOM | 165 | OE2 | GLU | 21 | 31.599 | 6.155 | 30.497 | 1.00 | 27.56 |
| ATOM | 166 | C | GLU | 21 | 31.861 | 10.115 | 26.238 | 1.00 | 11.80 |
| ATOM | 167 | O | GLU | 21 | 31.417 | 10.185 | 25.089 | 1.00 | 11.59 |
| ATOM | 168 | N | LEU | 22 | 33.013 | 10.661 | 26.528 | 1.00 | 11.07 |
| ATOM | 169 | CA | LEU | 22 | 33.838 | 11.349 | 25.587 | 1.00 | 11.81 |
| ATOM | 170 | CB | LEU | 22 | 34.811 | 12.325 | 26.236 | 1.00 | 9.69 |
| ATOM | 171 | CG | LEU | 22 | 34.424 | 13.644 | 26.794 | 1.00 | 8.78 |
| ATOM | 172 | CD1 | LEU | 22 | 34.103 | 14.677 | 25.719 | 1.00 | 8.17 |
| ATOM | 173 | CD2 | LEU | 22 | 33.310 | 13.559 | 27.815 | 1.00 | 8.71 |
| ATOM | 174 | C | LEU | 22 | 34.675 | 10.321 | 24.815 | 1.00 | 13.30 |
| ATOM | 175 | O | LEU | 22 | 35.079 | 9.332 | 25.372 | 1.00 | 13.83 |
| ATOM | 176 | N | GLU | 23 | 34.852 | 10.597 | 23.535 | 1.00 | 16.09 |
| ATOM | 177 | CA | GLU | 23 | 35.751 | 9.770 | 22.737 | 1.00 | 17.85 |
| ATOM | 178 | CB | GLU | 23 | 35.257 | 9.636 | 21.289 | 1.00 | 23.31 |
| ATOM | 179 | CG | GLU | 23 | 33.952 | 8.895 | 21.273 | 1.00 | 29.61 |
| ATOM | 180 | CD | GLU | 23 | 33.367 | 8.488 | 19.961 | 1.00 | 34.86 |
| ATOM | 181 | OE1 | GLU | 23 | 33.510 | 9.170 | 18.922 | 1.00 | 37.14 |
| ATOM | 182 | OE2 | GLU | 23 | 32.683 | 7.419 | 19.974 | 1.00 | 37.69 |
| ATOM | 183 | C | GLU | 23 | 37.087 | 10.532 | 22.787 | 1.00 | 16.82 |
| ATOM | 184 | O | GLU | 23 | 37.021 | 11.729 | 22.817 | 1.00 | 16.18 |
| ATOM | 185 | N | LEU | 24 | 38.209 | 9.855 | 22.917 | 1.00 | 18.03 |
| ATOM | 186 | CA | LEU | 24 | 39.524 | 10.444 | 22.930 | 1.00 | 17.31 |
| ATOM | 187 | CB | LEU | 24 | 40.436 | 9.892 | 24.031 | 1.00 | 16.16 |
| ATOM | 188 | CG | LEU | 24 | 40.230 | 10.228 | 25.490 | 1.00 | 16.48 |
| ATOM | 189 | CD1 | LEU | 24 | 40.257 | 11.765 | 25.662 | 1.00 | 17.54 |
| ATOM | 190 | CD2 | LEU | 24 | 38.965 | 9.743 | 26.117 | 1.00 | 15.61 |
| ATOM | 191 | C | LEU | 24 | 40.173 | 10.220 | 21.558 | 1.00 | 17.41 |
| ATOM | 192 | O | LEU | 24 | 39.995 | 9.166 | 20.916 | 1.00 | 19.08 |
| ATOM | 193 | N | PRO | 25 | 40.912 | 11.204 | 21.075 | 1.00 | 15.93 |
| ATOM | 194 | CA | PRO | 25 | 41.141 | 12.448 | 21.731 | 1.00 | 14.52 |
| ATOM | 195 | CB | PRO | 25 | 42.287 | 13.063 | 20.900 | 1.00 | 14.29 |
| ATOM | 196 | CG | PRO | 25 | 42.036 | 12.531 | 19.526 | 1.00 | 15.30 |
| ATOM | 197 | CD | PRO | 25 | 41.604 | 11.109 | 19.738 | 1.00 | 15.06 |
| ATOM | 198 | C | PRO | 25 | 39.995 | 13.443 | 21.653 | 1.00 | 13.35 |
| ATOM | 199 | O | PRO | 25 | 39.177 | 13.401 | 20.754 | 1.00 | 13.89 |
| ATOM | 200 | N | LEU | 26 | 39.985 | 14.367 | 22.602 | 1.00 | 13.79 |
| ATOM | 201 | CA | LEU | 26 | 38.996 | 15.418 | 22.666 | 1.00 | 12.59 |
| ATOM | 202 | CB | LEU | 26 | 39.082 | 16.256 | 23.904 | 1.00 | 12.08 |
| ATOM | 203 | CG | LEU | 26 | 38.886 | 15.669 | 25.289 | 1.00 | 12.93 |
| ATOM | 204 | CD1 | LEU | 26 | 38.866 | 16.788 | 26.340 | 1.00 | 10.60 |
| ATOM | 205 | CD2 | LEU | 26 | 37.642 | 14.803 | 25.381 | 1.00 | 12.07 |
| ATOM | 206 | C | LEU | 26 | 39.100 | 16.326 | 21.409 | 1.00 | 12.36 |
| ATOM | 207 | O | LEU | 26 | 40.197 | 16.480 | 20.886 | 1.00 | 12.03 |
| ATOM | 208 | N | THR | 27 | 37.963 | 16.834 | 20.967 | 1.00 | 12.65 |
| ATOM | 209 | CA | THR | 27 | 37.963 | 17.766 | 19.832 | 1.00 | 14.54 |
| ATOM | 210 | CB | THR | 27 | 36.532 | 18.035 | 19.308 | 1.00 | 15.30 |
| ATOM | 211 | OG1 | THR | 27 | 35.727 | 18.682 | 20.310 | 1.00 | 15.81 |
| ATOM | 212 | CG2 | THR | 27 | 35.847 | 16.719 | 18.948 | 1.00 | 14.42 |
| ATOM | 213 | C | THR | 27 | 38.493 | 19.093 | 20.391 | 1.00 | 15.69 |
| ATOM | 214 | O | THR | 27 | 38.511 | 19.249 | 21.642 | 1.00 | 15.10 |
| ATOM | 215 | N | LYS | 28 | 38.949 | 20.026 | 19.593 | 1.00 | 17.11 |
| ATOM | 216 | CA | LYS | 28 | 39.461 | 21.322 | 20.062 | 1.00 | 16.59 |
| ATOM | 217 | CB | LYS | 28 | 39.640 | 22.170 | 18.785 | 1.00 | 21.45 |
| ATOM | 218 | CG | LYS | 28 | 40.041 | 23.601 | 18.941 | 1.00 | 24.97 |
| ATOM | 219 | CD | LYS | 28 | 41.424 | 23.746 | 19.542 | 1.00 | 28.58 |
| ATOM | 220 | CE | LYS | 28 | 41.893 | 25.200 | 19.520 | 1.00 | 29.78 |

TABLE 1-continued

Structure Coordinates for S. aureus pdf

| ATOM | 221 | NZ | LYS | 28 | 43.362 | 25.231 | 19.863 | 1.00 | 30.20 |
|---|---|---|---|---|---|---|---|---|---|
| ATOM | 222 | C | LYS | 28 | 38.449 | 22.070 | 20.922 | 1.00 | 15.27 |
| ATOM | 223 | O | LYS | 28 | 38.795 | 22.754 | 21.899 | 1.00 | 14.45 |
| ATOM | 224 | N | GLU | 29 | 37.202 | 21.988 | 20.547 | 1.00 | 14.88 |
| ATOM | 225 | CA | GLU | 29 | 36.095 | 22.628 | 21.221 | 1.00 | 14.47 |
| ATOM | 226 | CB | GLU | 29 | 34.832 | 22.548 | 20.375 | 1.00 | 20.18 |
| ATOM | 227 | CG | GLU | 29 | 33.633 | 23.176 | 21.057 | 1.00 | 25.80 |
| ATOM | 228 | CD | GLU | 29 | 32.326 | 22.956 | 20.331 | 1.00 | 30.91 |
| ATOM | 229 | OE1 | GLU | 29 | 32.201 | 21.989 | 19.520 | 1.00 | 32.53 |
| ATOM | 230 | OE2 | GLU | 29 | 31.389 | 23.743 | 20.643 | 1.00 | 32.71 |
| ATOM | 231 | C | GLU | 29 | 35.873 | 22.024 | 22.595 | 1.00 | 13.31 |
| ATOM | 232 | O | GLU | 29 | 35.595 | 22.749 | 23.545 | 1.00 | 11.60 |
| ATOM | 233 | N | GLU | 30 | 35.940 | 20.686 | 22.711 | 1.00 | 12.75 |
| ATOM | 234 | CA | GLU | 30 | 35.795 | 20.032 | 24.009 | 1.00 | 10.36 |
| ATOM | 235 | CB | GLU | 30 | 35.700 | 18.517 | 23.814 | 1.00 | 10.77 |
| ATOM | 236 | CG | GLU | 30 | 34.365 | 18.110 | 23.139 | 1.00 | 12.50 |
| ATOM | 237 | CD | GLU | 30 | 34.397 | 16.669 | 22.642 | 1.00 | 11.90 |
| ATOM | 238 | OE1 | GLU | 30 | 35.467 | 16.104 | 22.370 | 1.00 | 12.79 |
| ATOM | 239 | OE2 | GLU | 30 | 33.310 | 16.151 | 22.474 | 1.00 | 14.28 |
| ATOM | 240 | C | GLU | 30 | 36.936 | 20.426 | 24.950 | 1.00 | 9.86 |
| ATOM | 241 | O | GLU | 30 | 36.678 | 20.595 | 26.156 | 1.00 | 9.16 |
| ATOM | 242 | N | LYS | 31 | 38.154 | 20.617 | 24.466 | 1.00 | 9.50 |
| ATOM | 243 | CA | LYS | 31 | 39.272 | 21.016 | 25.315 | 1.00 | 10.37 |
| ATOM | 244 | CB | LYS | 31 | 40.624 | 20.903 | 24.615 | 1.00 | 10.65 |
| ATOM | 245 | CG | LYS | 31 | 40.935 | 19.492 | 24.109 | 1.00 | 10.14 |
| ATOM | 246 | CD | LYS | 31 | 42.376 | 19.413 | 23.639 | 1.00 | 12.65 |
| ATOM | 247 | CE | LYS | 31 | 42.773 | 18.053 | 23.142 | 1.00 | 13.40 |
| ATOM | 248 | NZ | LYS | 31 | 44.122 | 17.978 | 22.539 | 1.00 | 16.75 |
| ATOM | 249 | C | LYS | 31 | 39.056 | 22.437 | 25.839 | 1.00 | 11.34 |
| ATOM | 250 | O | LYS | 31 | 39.219 | 22.729 | 27.019 | 1.00 | 10.78 |
| ATOM | 251 | N | GLU | 32 | 38.652 | 23.343 | 24.963 | 1.00 | 12.34 |
| ATOM | 252 | CA | GLU | 32 | 38.358 | 24.725 | 25.267 | 1.00 | 13.73 |
| ATOM | 253 | CB | GLU | 32 | 37.914 | 25.458 | 23.995 | 1.00 | 18.88 |
| ATOM | 254 | CG | GLU | 32 | 38.998 | 25.596 | 22.948 | 1.00 | 25.82 |
| ATOM | 255 | CD | GLU | 32 | 38.508 | 26.242 | 21.661 | 1.00 | 31.02 |
| ATOM | 256 | OE1 | GLU | 32 | 37.329 | 26.619 | 21.506 | 1.00 | 34.16 |
| ATOM | 257 | OE2 | GLU | 32 | 39.333 | 26.362 | 20.729 | 1.00 | 33.69 |
| ATOM | 258 | C | GLU | 32 | 37.266 | 24.829 | 26.333 | 1.00 | 12.41 |
| ATOM | 259 | O | GLU | 32 | 37.312 | 25.639 | 27.241 | 1.00 | 11.77 |
| ATOM | 260 | N | THR | 33 | 36.250 | 23.978 | 26.208 | 1.00 | 12.31 |
| ATOM | 261 | CA | THR | 33 | 35.163 | 23.899 | 27.157 | 1.00 | 12.37 |
| ATOM | 262 | CB | THR | 33 | 34.104 | 22.861 | 26.725 | 1.00 | 13.11 |
| ATOM | 263 | OG1 | THR | 33 | 33.517 | 23.349 | 25.513 | 1.00 | 15.23 |
| ATOM | 264 | CG2 | THR | 33 | 33.023 | 22.657 | 27.752 | 1.00 | 11.29 |
| ATOM | 265 | C | THR | 33 | 35.681 | 23.524 | 28.559 | 1.00 | 11.41 |
| ATOM | 266 | O | THR | 33 | 35.365 | 24.208 | 29.497 | 1.00 | 10.34 |
| ATOM | 267 | N | LEU | 34 | 36.486 | 22.474 | 28.658 | 1.00 | 11.17 |
| ATOM | 268 | CA | LEU | 34 | 37.030 | 22.021 | 29.928 | 1.00 | 10.16 |
| ATOM | 269 | CB | LEU | 34 | 37.678 | 20.654 | 29.693 | 1.00 | 9.41 |
| ATOM | 270 | CG | LEU | 34 | 38.102 | 19.874 | 30.942 | 1.00 | 8.70 |
| ATOM | 271 | CD1 | LEU | 34 | 36.909 | 19.607 | 31.858 | 1.00 | 5.18 |
| ATOM | 272 | CD2 | LEU | 34 | 38.697 | 18.541 | 30.452 | 1.00 | 8.15 |
| ATOM | 273 | C | LEU | 34 | 37.960 | 23.036 | 30.557 | 1.00 | 10.05 |
| ATOM | 274 | O | LEU | 34 | 37.967 | 23.258 | 31.785 | 1.00 | 10.33 |
| ATOM | 275 | N | ILE | 35 | 38.761 | 23.700 | 29.745 | 1.00 | 9.38 |
| ATOM | 276 | CA | ILE | 35 | 39.669 | 24.770 | 30.298 | 1.00 | 9.27 |
| ATOM | 277 | CB | ILE | 35 | 40.619 | 25.168 | 29.153 | 1.00 | 9.96 |
| ATOM | 278 | CG1 | ILE | 35 | 41.392 | 23.960 | 28.683 | 1.00 | 11.21 |
| ATOM | 279 | CD1 | ILE | 35 | 42.276 | 24.096 | 27.476 | 1.00 | 10.72 |
| ATOM | 280 | CG2 | ILE | 35 | 41.467 | 26.360 | 29.493 | 1.00 | 10.81 |
| ATOM | 281 | C | ILE | 35 | 38.843 | 25.908 | 30.801 | 1.00 | 8.81 |
| ATOM | 282 | O | ILE | 35 | 39.131 | 26.555 | 31.836 | 1.00 | 9.47 |
| ATOM | 283 | N | ALA | 36 | 37.769 | 26.277 | 30.047 | 1.00 | 8.60 |
| ATOM | 284 | CA | ALA | 36 | 36.878 | 27.369 | 30.469 | 1.00 | 8.07 |
| ATOM | 285 | CB | ALA | 36 | 35.833 | 27.665 | 29.390 | 1.00 | 8.37 |
| ATOM | 286 | C | ALA | 36 | 36.161 | 27.045 | 31.767 | 1.00 | 8.14 |
| ATOM | 287 | O | ALA | 36 | 35.768 | 27.917 | 32.560 | 1.00 | 8.12 |
| ATOM | 288 | N | MET | 37 | 35.881 | 25.724 | 31.941 | 1.00 | 8.77 |
| ATOM | 289 | CA | MET | 37 | 35.248 | 25.210 | 33.136 | 1.00 | 9.24 |
| ATOM | 290 | CB | MET | 37 | 34.795 | 23.764 | 33.059 | 1.00 | 8.72 |
| ATOM | 291 | CG | MET | 37 | 33.559 | 23.483 | 32.224 | 1.00 | 6.71 |
| ATOM | 292 | SD | MET | 37 | 33.335 | 21.789 | 31.709 | 1.00 | 6.53 |
| ATOM | 293 | CE | MET | 37 | 33.342 | 20.932 | 33.251 | 1.00 | 4.67 |
| ATOM | 294 | C | MET | 37 | 36.195 | 25.410 | 34.333 | 1.00 | 9.17 |
| ATOM | 295 | O | MET | 37 | 35.692 | 25.892 | 35.376 | 1.00 | 8.49 |
| ATOM | 296 | N | ARG | 38 | 37.452 | 25.050 | 34.165 | 1.00 | 8.88 |
| ATOM | 297 | CA | ARG | 38 | 38.401 | 25.295 | 35.266 | 1.00 | 8.29 |

TABLE 1-continued

Structure Coordinates for *S. aureus* pdf

| | | | | | | | | | |
|---|---|---|---|---|---|---|---|---|---|
| ATOM | 298 | CB | ARG | 38 | 39.761 | 24.673 | 34.946 | 1.00 | 6.27 |
| ATOM | 299 | CG | ARG | 38 | 40.886 | 25.129 | 35.854 | 1.00 | 6.22 |
| ATOM | 300 | CD | ARG | 38 | 42.253 | 24.472 | 35.513 | 1.00 | 6.20 |
| ATOM | 301 | NE | ARG | 38 | 43.275 | 24.989 | 36.431 | 1.00 | 8.87 |
| ATOM | 302 | CZ | ARG | 38 | 43.890 | 26.160 | 36.395 | 1.00 | 10.20 |
| ATOM | 303 | NH1 | ARG | 38 | 43.647 | 27.040 | 35.409 | 1.00 | 11.24 |
| ATOM | 304 | NH2 | ARG | 38 | 44.784 | 26.493 | 37.315 | 1.00 | 11.77 |
| ATOM | 305 | C | ARG | 38 | 38.583 | 26.825 | 35.430 | 1.00 | 9.07 |
| ATOM | 306 | O | ARG | 38 | 38.763 | 27.261 | 36.567 | 1.00 | 9.36 |
| ATOM | 307 | N | GLU | 39 | 38.575 | 27.572 | 34.337 | 1.00 | 8.69 |
| ATOM | 308 | CA | GLU | 39 | 38.771 | 29.029 | 34.403 | 1.00 | 9.54 |
| ATOM | 309 | CB | GLU | 39 | 39.029 | 29.643 | 33.049 | 1.00 | 10.78 |
| ATOM | 310 | CG | GLU | 39 | 39.650 | 31.040 | 33.051 | 1.00 | 14.31 |
| ATOM | 311 | CD | GLU | 39 | 41.070 | 30.997 | 33.632 | 1.00 | 17.29 |
| ATOM | 312 | OE1 | GLU | 39 | 41.712 | 29.936 | 33.706 | 1.00 | 17.09 |
| ATOM | 313 | OE2 | GLU | 39 | 41.577 | 32.041 | 34.079 | 1.00 | 19.58 |
| ATOM | 314 | C | GLU | 39 | 37.629 | 29.691 | 35.178 | 1.00 | 8.74 |
| ATOM | 315 | O | GLU | 39 | 37.872 | 30.680 | 35.887 | 1.00 | 8.33 |
| ATOM | 316 | N | PHE | 40 | 36.424 | 29.202 | 35.067 | 1.00 | 8.68 |
| ATOM | 317 | CA | PHE | 40 | 35.267 | 29.674 | 35.808 | 1.00 | 8.98 |
| ATOM | 318 | CB | PHE | 40 | 33.969 | 28.890 | 35.546 | 1.00 | 6.33 |
| ATOM | 319 | CG | PHE | 40 | 32.816 | 29.364 | 36.423 | 1.00 | 7.37 |
| ATOM | 320 | CD1 | PHE | 40 | 32.004 | 30.431 | 36.041 | 1.00 | 6.34 |
| ATOM | 321 | CE1 | PHE | 40 | 30.944 | 30.806 | 36.826 | 1.00 | 7.39 |
| ATOM | 322 | CZ | PHE | 40 | 30.729 | 30.221 | 38.073 | 1.00 | 8.75 |
| ATOM | 323 | CE2 | PHE | 40 | 31.553 | 29.164 | 38.474 | 1.00 | 7.42 |
| ATOM | 324 | CD2 | PHE | 40 | 32.570 | 28.749 | 37.650 | 1.00 | 5.86 |
| ATOM | 325 | C | PHE | 40 | 35.567 | 29.539 | 37.321 | 1.00 | 9.68 |
| ATOM | 326 | O | PHE | 40 | 35.299 | 30.458 | 38.106 | 1.00 | 8.96 |
| ATOM | 327 | N | LEU | 41 | 36.096 | 28.389 | 37.716 | 1.00 | 8.34 |
| ATOM | 328 | CA | LEU | 41 | 36.407 | 28.121 | 39.108 | 1.00 | 7.20 |
| ATOM | 329 | CB | LEU | 41 | 36.736 | 26.662 | 39.311 | 1.00 | 5.79 |
| ATOM | 330 | CG | LEU | 41 | 35.632 | 25.661 | 38.986 | 1.00 | 4.96 |
| ATOM | 331 | CD1 | LEU | 41 | 36.180 | 24.230 | 39.076 | 1.00 | 4.68 |
| ATOM | 332 | CD2 | LEU | 41 | 34.592 | 25.769 | 40.118 | 1.00 | 5.67 |
| ATOM | 333 | C | LEU | 41 | 37.487 | 29.057 | 39.633 | 1.00 | 6.55 |
| ATOM | 334 | O | LEU | 41 | 37.318 | 29.593 | 40.732 | 1.00 | 6.21 |
| ATOM | 335 | N | VAL | 42 | 38.543 | 29.226 | 38.866 | 1.00 | 6.90 |
| ATOM | 336 | CA | VAL | 42 | 39.620 | 30.141 | 39.229 | 1.00 | 8.11 |
| ATOM | 337 | CB | VAL | 42 | 40.640 | 30.109 | 38.086 | 1.00 | 11.15 |
| ATOM | 338 | CG1 | VAL | 42 | 41.734 | 31.155 | 38.206 | 1.00 | 13.45 |
| ATOM | 339 | CG2 | VAL | 42 | 41.304 | 28.748 | 37.976 | 1.00 | 11.23 |
| ATOM | 340 | C | VAL | 42 | 38.991 | 31.513 | 39.408 | 1.00 | 8.71 |
| ATOM | 341 | O | VAL | 42 | 39.122 | 32.126 | 40.489 | 1.00 | 10.31 |
| ATOM | 342 | N | ASN | 43 | 38.252 | 32.049 | 38.442 | 1.00 | 8.34 |
| ATOM | 343 | CA | ASN | 43 | 37.596 | 33.354 | 38.565 | 1.00 | 8.46 |
| ATOM | 344 | CB | ASN | 43 | 36.811 | 33.707 | 37.239 | 1.00 | 8.52 |
| ATOM | 345 | CG | ASN | 43 | 37.814 | 34.020 | 36.161 | 1.00 | 9.24 |
| ATOM | 346 | OD1 | ASN | 43 | 38.937 | 34.339 | 36.546 | 1.00 | 10.81 |
| ATOM | 347 | ND2 | ASN | 43 | 37.464 | 33.943 | 34.891 | 1.00 | 10.73 |
| ATOM | 348 | C | ASN | 43 | 36.632 | 33.504 | 39.695 | 1.00 | 9.08 |
| ATOM | 349 | O | ASN | 43 | 36.559 | 34.588 | 40.314 | 1.00 | 8.98 |
| ATOM | 350 | N | SER | 44 | 35.887 | 32.473 | 40.035 | 1.00 | 9.07 |
| ATOM | 351 | CA | SER | 44 | 34.906 | 32.506 | 41.091 | 1.00 | 10.54 |
| ATOM | 352 | CB | SER | 44 | 33.940 | 31.317 | 41.107 | 1.00 | 9.94 |
| ATOM | 353 | OG | SER | 44 | 34.463 | 30.152 | 41.665 | 1.00 | 10.32 |
| ATOM | 354 | C | SER | 44 | 35.612 | 32.595 | 42.463 | 1.00 | 11.84 |
| ATOM | 355 | O | SER | 44 | 35.022 | 33.048 | 43.445 | 1.00 | 13.02 |
| ATOM | 356 | N | GLN | 45 | 36.866 | 32.177 | 42.517 | 1.00 | 12.29 |
| ATOM | 357 | CA | GLN | 45 | 37.648 | 32.199 | 43.727 | 1.00 | 12.76 |
| ATOM | 358 | CB | GLN | 45 | 38.552 | 30.951 | 43.870 | 1.00 | 13.51 |
| ATOM | 359 | CG | GLN | 45 | 37.711 | 29.688 | 44.112 | 1.00 | 12.21 |
| ATOM | 360 | CD | GLN | 45 | 38.518 | 28.436 | 44.161 | 1.00 | 13.51 |
| ATOM | 361 | OE1 | GLN | 45 | 39.733 | 28.479 | 44.331 | 1.00 | 15.12 |
| ATOM | 362 | NE2 | GLN | 45 | 37.819 | 27.301 | 43.898 | 1.00 | 11.45 |
| ATOM | 363 | C | GLN | 45 | 38.451 | 33.491 | 43.882 | 1.00 | 14.04 |
| ATOM | 364 | O | GLN | 45 | 38.996 | 33.746 | 44.942 | 1.00 | 14.63 |
| ATOM | 365 | N | ASP | 46 | 38.518 | 34.305 | 42.869 | 1.00 | 14.76 |
| ATOM | 366 | CA | ASP | 46 | 39.203 | 35.595 | 42.881 | 1.00 | 17.02 |
| ATOM | 367 | CB | ASP | 46 | 39.977 | 35.835 | 41.627 | 1.00 | 20.12 |
| ATOM | 368 | CG | ASP | 46 | 40.799 | 37.118 | 41.646 | 1.00 | 23.64 |
| ATOM | 369 | OD1 | ASP | 46 | 40.229 | 38.095 | 42.163 | 1.00 | 23.90 |
| ATOM | 370 | OD2 | ASP | 46 | 41.954 | 37.141 | 41.179 | 1.00 | 26.97 |
| ATOM | 371 | C | ASP | 46 | 38.159 | 36.639 | 43.278 | 1.00 | 16.96 |
| ATOM | 372 | O | ASP | 46 | 37.141 | 36.906 | 42.690 | 1.00 | 15.76 |
| ATOM | 373 | N | GLU | 47 | 38.383 | 37.201 | 44.471 | 1.00 | 18.61 |
| ATOM | 374 | CA | GLU | 47 | 37.524 | 38.172 | 45.105 | 1.00 | 20.77 |

TABLE 1-continued

Structure Coordinates for *S. aureus* pdf

| ATOM | 375 | CB | GLU | 47 | 38.318 | 38.747 | 46.281 | 1.00 | 26.35 |
|------|-----|-----|-----|----|--------|--------|--------|------|-------|
| ATOM | 376 | CG | GLU | 47 | 37.601 | 39.794 | 47.124 | 1.00 | 31.95 |
| ATOM | 377 | CD | GLU | 47 | 38.607 | 40.361 | 48.151 | 1.00 | 35.24 |
| ATOM | 378 | OE1 | GLU | 47 | 39.590 | 41.011 | 47.707 | 1.00 | 36.36 |
| ATOM | 379 | OE2 | GLU | 47 | 38.401 | 40.085 | 49.347 | 1.00 | 37.08 |
| ATOM | 380 | C | GLU | 47 | 37.043 | 39.303 | 44.202 | 1.00 | 20.14 |
| ATOM | 381 | O | GLU | 47 | 35.844 | 39.612 | 44.172 | 1.00 | 19.26 |
| ATOM | 382 | N | GLU | 48 | 37.975 | 39.957 | 43.516 | 1.00 | 19.74 |
| ATOM | 383 | CA | GLU | 48 | 37.697 | 41.040 | 42.619 | 1.00 | 20.15 |
| ATOM | 384 | CB | GLU | 48 | 39.015 | 41.724 | 42.176 | 1.00 | 26.28 |
| ATOM | 385 | CG | GLU | 48 | 38.788 | 42.838 | 41.175 | 1.00 | 33.55 |
| ATOM | 386 | CD | GLU | 48 | 39.965 | 43.661 | 40.716 | 1.00 | 38.79 |
| ATOM | 387 | OE1 | GLU | 48 | 41.131 | 43.498 | 41.173 | 1.00 | 40.40 |
| ATOM | 388 | OE2 | GLU | 48 | 39.734 | 44.559 | 39.829 | 1.00 | 39.98 |
| ATOM | 389 | C | GLU | 48 | 36.940 | 40.613 | 41.365 | 1.00 | 17.56 |
| ATOM | 390 | O | GLU | 48 | 35.980 | 41.201 | 40.970 | 1.00 | 15.31 |
| ATOM | 391 | N | ILE | 49 | 37.483 | 39.560 | 40.714 | 1.00 | 17.33 |
| ATOM | 392 | CA | ILE | 49 | 36.899 | 39.040 | 39.494 | 1.00 | 15.12 |
| ATOM | 393 | CB | ILE | 49 | 37.765 | 38.038 | 38.757 | 1.00 | 16.13 |
| ATOM | 394 | CG1 | ILE | 49 | 39.111 | 38.674 | 38.292 | 1.00 | 16.15 |
| ATOM | 395 | CD1 | ILE | 49 | 40.129 | 37.587 | 37.857 | 1.00 | 13.47 |
| ATOM | 396 | CG2 | ILE | 49 | 36.997 | 37.575 | 37.496 | 1.00 | 16.11 |
| ATOM | 397 | C | ILE | 49 | 35.503 | 38.558 | 39.794 | 1.00 | 13.80 |
| ATOM | 398 | O | ILE | 49 | 34.619 | 38.936 | 39.034 | 1.00 | 14.67 |
| ATOM | 399 | N | ALA | 50 | 35.287 | 37.841 | 40.890 | 1.00 | 12.57 |
| ATOM | 400 | CA | ALA | 50 | 33.952 | 37.373 | 41.233 | 1.00 | 12.32 |
| ATOM | 401 | CB | ALA | 50 | 33.951 | 36.441 | 42.447 | 1.00 | 10.25 |
| ATOM | 402 | C | ALA | 50 | 33.017 | 38.526 | 41.500 | 1.00 | 12.90 |
| ATOM | 403 | O | ALA | 50 | 31.824 | 38.435 | 41.186 | 1.00 | 12.81 |
| ATOM | 404 | N | LYS | 51 | 33.530 | 39.604 | 42.123 | 1.00 | 14.84 |
| ATOM | 405 | CA | LYS | 51 | 32.621 | 40.724 | 42.364 | 1.00 | 17.61 |
| ATOM | 406 | CB | LYS | 51 | 33.059 | 41.746 | 43.393 | 1.00 | 23.09 |
| ATOM | 407 | CG | LYS | 51 | 33.488 | 41.245 | 44.742 | 1.00 | 29.47 |
| ATOM | 408 | CD | LYS | 51 | 32.742 | 40.030 | 45.276 | 1.00 | 35.11 |
| ATOM | 409 | CE | LYS | 51 | 31.236 | 40.116 | 45.393 | 1.00 | 38.34 |
| ATOM | 410 | NZ | LYS | 51 | 30.581 | 38.814 | 45.690 | 1.00 | 39.45 |
| ATOM | 411 | C | LYS | 51 | 32.262 | 41.424 | 41.035 | 1.00 | 16.20 |
| ATOM | 412 | O | LYS | 51 | 31.066 | 41.571 | 40.745 | 1.00 | 17.61 |
| ATOM | 413 | N | ARG | 52 | 33.240 | 41.788 | 40.263 | 1.00 | 15.36 |
| ATOM | 414 | CA | ARG | 52 | 33.029 | 42.487 | 38.995 | 1.00 | 15.36 |
| ATOM | 415 | CB | ARG | 52 | 34.299 | 42.597 | 38.210 | 1.00 | 15.92 |
| ATOM | 416 | CG | ARG | 52 | 34.190 | 43.493 | 36.961 | 1.00 | 20.56 |
| ATOM | 417 | CD | ARG | 52 | 35.484 | 43.366 | 36.171 | 1.00 | 25.75 |
| ATOM | 418 | NE | ARG | 52 | 36.584 | 43.664 | 37.113 | 1.00 | 30.94 |
| ATOM | 419 | CZ | ARG | 52 | 37.845 | 43.340 | 36.840 | 1.00 | 34.86 |
| ATOM | 420 | NH1 | ARG | 52 | 38.178 | 42.759 | 35.680 | 1.00 | 36.86 |
| ATOM | 421 | NH2 | ARG | 52 | 38.734 | 43.409 | 37.825 | 1.00 | 36.03 |
| ATOM | 422 | C | ARG | 52 | 32.016 | 41.733 | 38.124 | 1.00 | 15.87 |
| ATOM | 423 | O | ARG | 52 | 31.146 | 42.328 | 37.514 | 1.00 | 15.88 |
| ATOM | 424 | N | TYR | 53 | 32.184 | 40.394 | 38.051 | 1.00 | 15.45 |
| ATOM | 425 | CA | TYR | 53 | 31.314 | 39.566 | 37.273 | 1.00 | 14.70 |
| ATOM | 426 | CB | TYR | 53 | 32.073 | 38.518 | 36.434 | 1.00 | 15.59 |
| ATOM | 427 | CG | TYR | 53 | 32.954 | 39.236 | 35.446 | 1.00 | 16.81 |
| ATOM | 428 | CD1 | TYR | 53 | 32.407 | 39.794 | 34.291 | 1.00 | 17.94 |
| ATOM | 429 | CE1 | TYR | 53 | 33.218 | 40.509 | 33.416 | 1.00 | 19.07 |
| ATOM | 430 | CZ | TYR | 53 | 34.568 | 40.622 | 33.684 | 1.00 | 19.48 |
| ATOM | 431 | OH | TYR | 53 | 35.396 | 41.309 | 32.827 | 1.00 | 22.92 |
| ATOM | 432 | CE2 | TYR | 53 | 35.110 | 40.078 | 34.818 | 1.00 | 19.01 |
| ATOM | 433 | CD2 | TYR | 53 | 34.301 | 39.379 | 35.692 | 1.00 | 18.15 |
| ATOM | 434 | C | TYR | 53 | 30.181 | 38.907 | 37.974 | 1.00 | 14.36 |
| ATOM | 435 | O | TYR | 53 | 29.510 | 38.141 | 37.274 | 1.00 | 15.28 |
| ATOM | 436 | N | GLY | 54 | 29.926 | 39.126 | 39.252 | 1.00 | 14.71 |
| ATOM | 437 | CA | GLY | 54 | 28.814 | 38.492 | 39.937 | 1.00 | 15.24 |
| ATOM | 438 | C | GLY | 54 | 28.886 | 36.981 | 39.985 | 1.00 | 16.54 |
| ATOM | 439 | O | GLY | 54 | 27.879 | 36.281 | 39.822 | 1.00 | 19.66 |
| ATOM | 440 | N | LEU | 55 | 30.071 | 36.433 | 40.235 | 1.00 | 15.81 |
| ATOM | 441 | CA | LEU | 55 | 30.300 | 35.000 | 40.253 | 1.00 | 14.58 |
| ATOM | 442 | CB | LEU | 55 | 31.684 | 34.640 | 39.689 | 1.00 | 10.75 |
| ATOM | 443 | CG | LEU | 55 | 32.128 | 35.125 | 38.328 | 1.00 | 8.84 |
| ATOM | 444 | CD1 | LEU | 55 | 33.483 | 34.650 | 37.920 | 1.00 | 6.15 |
| ATOM | 445 | CD2 | LEU | 55 | 31.095 | 34.816 | 37.227 | 1.00 | 8.13 |
| ATOM | 446 | C | LEU | 55 | 30.165 | 34.407 | 41.645 | 1.00 | 14.82 |
| ATOM | 447 | O | LEU | 55 | 30.668 | 34.952 | 42.634 | 1.00 | 15.45 |
| ATOM | 448 | N | ARG | 56 | 29.397 | 33.312 | 41.702 | 1.00 | 13.86 |
| ATOM | 449 | CA | ARG | 56 | 29.268 | 32.583 | 42.994 | 1.00 | 14.05 |
| ATOM | 450 | CB | ARG | 56 | 27.988 | 31.773 | 42.901 | 1.00 | 12.84 |
| ATOM | 451 | CG | ARG | 56 | 27.702 | 30.880 | 44.040 | 1.00 | 12.65 |

TABLE 1-continued

Structure Coordinates for *S. aureus* pdf

| ATOM | 452 | CD | ARG | 56 | 26.371 | 30.171 | 43.928 | 1.00 | 13.01 |
|------|-----|-----|-----|----|--------|--------|--------|------|-------|
| ATOM | 453 | NE | ARG | 56 | 26.264 | 29.199 | 44.998 | 1.00 | 13.72 |
| ATOM | 454 | CZ | ARG | 56 | 25.247 | 28.411 | 45.241 | 1.00 | 12.53 |
| ATOM | 455 | NH1 | ARG | 56 | 24.176 | 28.440 | 44.495 | 1.00 | 10.89 |
| ATOM | 456 | NH2 | ARG | 56 | 25.422 | 27.610 | 46.289 | 1.00 | 14.43 |
| ATOM | 457 | C | ARG | 56 | 30.501 | 31.671 | 43.133 | 1.00 | 14.45 |
| ATOM | 458 | O | ARG | 56 | 30.849 | 30.913 | 42.200 | 1.00 | 14.08 |
| ATOM | 459 | N | SER | 57 | 31.222 | 31.754 | 44.225 | 1.00 | 13.89 |
| ATOM | 460 | CA | SER | 57 | 32.426 | 30.929 | 44.412 | 1.00 | 15.05 |
| ATOM | 461 | CB | SER | 57 | 33.023 | 31.247 | 45.792 | 1.00 | 15.54 |
| ATOM | 462 | OG | SER | 57 | 34.277 | 30.604 | 45.995 | 1.00 | 17.22 |
| ATOM | 463 | C | SER | 57 | 32.107 | 29.424 | 44.362 | 1.00 | 14.39 |
| ATOM | 464 | O | SER | 57 | 31.028 | 29.003 | 44.817 | 1.00 | 14.42 |
| ATOM | 465 | N | GLY | 58 | 32.997 | 28.630 | 43.816 | 1.00 | 13.20 |
| ATOM | 466 | CA | GLY | 58 | 32.724 | 27.157 | 43.793 | 1.00 | 10.96 |
| ATOM | 467 | C | GLY | 58 | 34.050 | 26.420 | 43.697 | 1.00 | 8.84 |
| ATOM | 468 | O | GLY | 58 | 35.027 | 27.045 | 43.316 | 1.00 | 9.13 |
| ATOM | 469 | N | VAL | 59 | 34.082 | 25.126 | 43.982 | 1.00 | 8.47 |
| ATOM | 470 | CA | VAL | 59 | 35.220 | 24.274 | 43.887 | 1.00 | 7.38 |
| ATOM | 471 | CB | VAL | 59 | 35.731 | 23.702 | 45.248 | 1.00 | 6.40 |
| ATOM | 472 | CG1 | VAL | 59 | 36.137 | 24.837 | 46.154 | 1.00 | 2.67 |
| ATOM | 473 | CG2 | VAL | 59 | 34.729 | 22.751 | 45.834 | 1.00 | 6.06 |
| ATOM | 474 | C | VAL | 59 | 35.111 | 23.138 | 42.895 | 1.00 | 6.56 |
| ATOM | 475 | O | VAL | 59 | 36.087 | 22.423 | 42.623 | 1.00 | 5.81 |
| ATOM | 476 | N | GLY | 60 | 33.901 | 22.917 | 42.339 | 1.00 | 5.18 |
| ATOM | 477 | CA | GLY | 60 | 33.686 | 21.922 | 41.328 | 1.00 | 3.01 |
| ATOM | 478 | C | GLY | 60 | 32.684 | 22.363 | 40.281 | 1.00 | 4.83 |
| ATOM | 479 | O | GLY | 60 | 31.831 | 23.228 | 40.563 | 1.00 | 7.05 |
| ATOM | 480 | N | LEU | 61 | 32.723 | 21.833 | 39.071 | 1.00 | 4.97 |
| ATOM | 481 | CA | LEU | 61 | 31.800 | 22.185 | 38.012 | 1.00 | 5.34 |
| ATOM | 482 | CB | LEU | 61 | 32.356 | 23.451 | 37.250 | 1.00 | 4.23 |
| ATOM | 483 | CG | LEU | 61 | 31.400 | 24.019 | 36.212 | 1.00 | 4.22 |
| ATOM | 484 | CD1 | LEU | 61 | 30.116 | 24.482 | 36.841 | 1.00 | 2.46 |
| ATOM | 485 | CD2 | LEU | 61 | 32.030 | 25.178 | 35.413 | 1.00 | 4.72 |
| ATOM | 486 | C | LEU | 61 | 31.694 | 21.018 | 37.026 | 1.00 | 5.60 |
| ATOM | 487 | O | LEU | 61 | 32.750 | 20.517 | 36.638 | 1.00 | 6.42 |
| ATOM | 488 | N | ALA | 62 | 30.504 | 20.552 | 36.686 | 1.00 | 5.63 |
| ATOM | 489 | CA | ALA | 62 | 30.418 | 19.406 | 35.741 | 1.00 | 4.65 |
| ATOM | 490 | CB | ALA | 62 | 29.619 | 18.292 | 36.364 | 1.00 | 2.45 |
| ATOM | 491 | C | ALA | 62 | 29.793 | 19.935 | 34.451 | 1.00 | 5.95 |
| ATOM | 492 | O | ALA | 62 | 28.964 | 20.817 | 34.490 | 1.00 | 6.05 |
| ATOM | 493 | N | ALA | 63 | 30.228 | 19.393 | 33.287 | 1.00 | 6.80 |
| ATOM | 494 | CA | ALA | 63 | 29.749 | 19.839 | 31.985 | 1.00 | 6.73 |
| ATOM | 495 | CB | ALA | 63 | 30.529 | 19.136 | 30.903 | 1.00 | 4.62 |
| ATOM | 496 | C | ALA | 63 | 28.270 | 19.965 | 31.891 | 1.00 | 8.06 |
| ATOM | 497 | O | ALA | 63 | 27.704 | 20.987 | 31.462 | 1.00 | 7.93 |
| ATOM | 498 | N | PRO | 64 | 27.455 | 19.043 | 32.424 | 1.00 | 9.12 |
| ATOM | 499 | CA | PRO | 64 | 25.985 | 19.168 | 32.412 | 1.00 | 8.90 |
| ATOM | 500 | CB | PRO | 64 | 25.605 | 17.981 | 33.293 | 1.00 | 8.17 |
| ATOM | 501 | CG | PRO | 64 | 26.622 | 16.974 | 32.833 | 1.00 | 7.79 |
| ATOM | 502 | CD | PRO | 64 | 27.917 | 17.751 | 32.936 | 1.00 | 8.59 |
| ATOM | 503 | C | PRO | 64 | 25.470 | 20.474 | 32.967 | 1.00 | 10.82 |
| ATOM | 504 | O | PRO | 64 | 24.417 | 21.004 | 32.529 | 1.00 | 12.14 |
| ATOM | 505 | N | GLN | 65 | 26.166 | 21.045 | 33.961 | 1.00 | 9.00 |
| ATOM | 506 | CA | GLN | 65 | 25.887 | 22.265 | 34.602 | 1.00 | 9.54 |
| ATOM | 507 | CB | GLN | 65 | 26.745 | 22.513 | 35.855 | 1.00 | 7.85 |
| ATOM | 508 | CG | GLN | 65 | 26.491 | 21.503 | 36.986 | 1.00 | 7.50 |
| ATOM | 509 | CD | GLN | 65 | 27.298 | 21.965 | 38.217 | 1.00 | 7.64 |
| ATOM | 510 | OE1 | GLN | 65 | 28.430 | 21.506 | 38.343 | 1.00 | 6.16 |
| ATOM | 511 | NE2 | GLN | 65 | 26.694 | 22.855 | 39.036 | 1.00 | 5.03 |
| ATOM | 512 | C | GLN | 65 | 25.965 | 23.523 | 33.712 | 1.00 | 9.56 |
| ATOM | 513 | O | GLN | 65 | 25.400 | 24.560 | 34.092 | 1.00 | 9.71 |
| ATOM | 514 | N | ILE | 66 | 26.607 | 23.468 | 32.580 | 1.00 | 9.17 |
| ATOM | 515 | CA | ILE | 66 | 26.768 | 24.427 | 31.569 | 1.00 | 8.61 |
| ATOM | 516 | CB | ILE | 66 | 28.175 | 24.958 | 31.202 | 1.00 | 7.57 |
| ATOM | 517 | CG1 | ILE | 66 | 29.148 | 23.899 | 30.706 | 1.00 | 7.91 |
| ATOM | 518 | CD1 | ILE | 66 | 30.433 | 24.581 | 30.125 | 1.00 | 7.44 |
| ATOM | 519 | CG2 | ILE | 66 | 28.749 | 25.769 | 32.340 | 1.00 | 7.53 |
| ATOM | 520 | C | ILE | 66 | 26.068 | 23.881 | 30.298 | 1.00 | 9.39 |
| ATOM | 521 | O | ILE | 66 | 26.309 | 24.232 | 29.163 | 1.00 | 10.40 |
| ATOM | 522 | N | ASN | 67 | 25.126 | 22.986 | 30.510 | 1.00 | 10.49 |
| ATOM | 523 | CA | ASN | 67 | 24.266 | 22.369 | 29.557 | 1.00 | 11.57 |
| ATOM | 524 | CB | ASN | 67 | 23.399 | 23.500 | 28.929 | 1.00 | 12.56 |
| ATOM | 525 | CG | ASN | 67 | 22.171 | 22.934 | 28.230 | 1.00 | 12.16 |
| ATOM | 526 | OD1 | ASN | 67 | 21.751 | 21.813 | 28.405 | 1.00 | 12.53 |
| ATOM | 527 | ND2 | ASN | 67 | 21.492 | 23.785 | 27.485 | 1.00 | 14.18 |
| ATOM | 528 | C | ASN | 67 | 24.980 | 21.596 | 28.464 | 1.00 | 11.97 |

TABLE 1-continued

Structure Coordinates for S. aureus pdf

| | | | | | | | | | |
|---|---|---|---|---|---|---|---|---|---|
| ATOM | 529 | O | ASN | 67 | 24.610 | 21.590 | 27.263 | 1.00 | 12.28 |
| ATOM | 530 | N | ILE | 68 | 26.093 | 21.000 | 28.821 | 1.00 | 10.89 |
| ATOM | 531 | CA | ILE | 68 | 26.918 | 20.161 | 27.888 | 1.00 | 10.88 |
| ATOM | 532 | CB | ILE | 68 | 28.298 | 20.745 | 27.721 | 1.00 | 10.24 |
| ATOM | 533 | CG1 | ILE | 68 | 28.286 | 22.078 | 26.953 | 1.00 | 9.48 |
| ATOM | 534 | CD1 | ILE | 68 | 29.646 | 22.766 | 26.933 | 1.00 | 7.35 |
| ATOM | 535 | CG2 | ILE | 68 | 29.224 | 19.745 | 26.992 | 1.00 | 9.60 |
| ATOM | 536 | C | ILE | 68 | 26.868 | 18.749 | 28.499 | 1.00 | 10.44 |
| ATOM | 537 | O | ILE | 68 | 27.477 | 18.497 | 29.537 | 1.00 | 9.24 |
| ATOM | 538 | N | SER | 69 | 26.091 | 17.859 | 27.888 | 1.00 | 10.07 |
| ATOM | 539 | CA | SER | 69 | 25.867 | 16.541 | 28.468 | 1.00 | 10.16 |
| ATOM | 540 | CB | SER | 69 | 24.475 | 16.071 | 28.036 | 1.00 | 8.68 |
| ATOM | 541 | OG | SER | 69 | 23.982 | 14.974 | 28.781 | 1.00 | 9.95 |
| ATOM | 542 | C | SER | 69 | 26.972 | 15.562 | 28.156 | 1.00 | 10.74 |
| ATOM | 543 | O | SER | 69 | 26.778 | 14.529 | 27.532 | 1.00 | 11.54 |
| ATOM | 544 | N | LYS | 70 | 28.184 | 15.911 | 28.570 | 1.00 | 10.10 |
| ATOM | 545 | CA | LYS | 70 | 29.409 | 15.153 | 28.370 | 1.00 | 9.96 |
| ATOM | 546 | CB | LYS | 70 | 30.368 | 15.890 | 27.428 | 1.00 | 10.10 |
| ATOM | 547 | CG | LYS | 70 | 29.624 | 16.156 | 26.075 | 1.00 | 13.10 |
| ATOM | 548 | CD | LYS | 70 | 30.666 | 16.689 | 25.078 | 1.00 | 15.02 |
| ATOM | 549 | CE | LYS | 70 | 30.002 | 16.829 | 23.705 | 1.00 | 15.43 |
| ATOM | 550 | NZ | LYS | 70 | 30.955 | 17.277 | 22.697 | 1.00 | 17.50 |
| ATOM | 551 | C | LYS | 70 | 30.082 | 14.848 | 29.722 | 1.00 | 9.28 |
| ATOM | 552 | O | LYS | 70 | 29.937 | 15.649 | 30.656 | 1.00 | 10.48 |
| ATOM | 553 | N | ARG | 71 | 30.789 | 13.750 | 29.827 | 1.00 | 7.46 |
| ATOM | 554 | CA | ARG | 71 | 31.383 | 13.295 | 31.076 | 1.00 | 7.42 |
| ATOM | 555 | CB | ARG | 71 | 31.426 | 11.762 | 31.151 | 1.00 | 5.24 |
| ATOM | 556 | CG | ARG | 71 | 30.124 | 11.043 | 30.888 | 1.00 | 4.69 |
| ATOM | 557 | CD | ARG | 71 | 30.141 | 9.561 | 31.166 | 1.00 | 3.45 |
| ATOM | 558 | NE | ARG | 71 | 30.097 | 9.086 | 32.533 | 1.00 | 5.53 |
| ATOM | 559 | CZ | ARG | 71 | 29.004 | 9.030 | 33.279 | 1.00 | 6.30 |
| ATOM | 560 | NH1 | ARG | 71 | 27.846 | 9.361 | 32.738 | 1.00 | 6.87 |
| ATOM | 561 | NH2 | ARG | 71 | 28.983 | 8.718 | 34.567 | 1.00 | 9.93 |
| ATOM | 562 | C | ARG | 71 | 32.756 | 13.852 | 31.351 | 1.00 | 7.34 |
| ATOM | 563 | O | ARG | 71 | 33.782 | 13.219 | 31.176 | 1.00 | 7.04 |
| ATOM | 564 | N | MET | 72 | 32.764 | 15.142 | 31.733 | 1.00 | 8.16 |
| ATOM | 565 | CA | MET | 72 | 33.929 | 15.899 | 32.038 | 1.00 | 7.49 |
| ATOM | 566 | CB | MET | 72 | 34.226 | 16.975 | 30.968 | 1.00 | 11.49 |
| ATOM | 567 | CG | MET | 72 | 34.482 | 16.514 | 29.597 | 1.00 | 14.92 |
| ATOM | 568 | SD | MET | 72 | 34.929 | 17.771 | 28.426 | 1.00 | 14.46 |
| ATOM | 569 | CE | MET | 72 | 33.462 | 18.708 | 28.193 | 1.00 | 15.90 |
| ATOM | 570 | C | MET | 72 | 33.639 | 16.756 | 33.276 | 1.00 | 6.05 |
| ATOM | 571 | O | MET | 72 | 32.583 | 17.367 | 33.360 | 1.00 | 5.46 |
| ATOM | 572 | N | ILE | 73 | 34.610 | 16.921 | 34.129 | 1.00 | 5.83 |
| ATOM | 573 | CA | ILE | 73 | 34.470 | 17.767 | 35.294 | 1.00 | 4.01 |
| ATOM | 574 | CB | ILE | 73 | 34.134 | 16.939 | 36.559 | 1.00 | 4.50 |
| ATOM | 575 | CG1 | ILE | 73 | 35.208 | 15.825 | 36.788 | 1.00 | 3.12 |
| ATOM | 576 | CD1 | ILE | 73 | 35.070 | 15.150 | 38.142 | 1.00 | 3.42 |
| ATOM | 577 | CG2 | ILE | 73 | 32.758 | 16.373 | 36.503 | 1.00 | 3.16 |
| ATOM | 578 | C | ILE | 73 | 35.728 | 18.596 | 35.564 | 1.00 | 4.80 |
| ATOM | 579 | O | ILE | 73 | 36.814 | 18.324 | 35.070 | 1.00 | 4.39 |
| ATOM | 580 | N | ALA | 74 | 35.570 | 19.655 | 36.382 | 1.00 | 4.79 |
| ATOM | 581 | CA | ALA | 74 | 36.744 | 20.441 | 36.785 | 1.00 | 5.15 |
| ATOM | 582 | CB | ALA | 74 | 36.868 | 21.730 | 36.054 | 1.00 | 5.71 |
| ATOM | 583 | C | ALA | 74 | 36.659 | 20.559 | 38.308 | 1.00 | 4.79 |
| ATOM | 584 | O | ALA | 74 | 35.592 | 20.723 | 38.844 | 1.00 | 4.28 |
| ATOM | 585 | N | VAL | 75 | 37.774 | 20.324 | 39.020 | 1.00 | 6.37 |
| ATOM | 586 | CA | VAL | 75 | 37.811 | 20.449 | 40.484 | 1.00 | 6.45 |
| ATOM | 587 | CB | VAL | 75 | 37.984 | 19.144 | 41.290 | 1.00 | 5.03 |
| ATOM | 588 | CG1 | VAL | 75 | 38.075 | 19.427 | 42.796 | 1.00 | 2.00 |
| ATOM | 589 | CG2 | VAL | 75 | 36.744 | 18.271 | 41.056 | 1.00 | 3.76 |
| ATOM | 590 | C | VAL | 75 | 38.918 | 21.416 | 40.854 | 1.00 | 7.44 |
| ATOM | 591 | O | VAL | 75 | 40.043 | 21.229 | 40.321 | 1.00 | 8.86 |
| ATOM | 592 | N | LEU | 76 | 38.635 | 22.413 | 41.703 | 1.00 | 6.88 |
| ATOM | 593 | CA | LEU | 76 | 39.681 | 23.368 | 42.027 | 1.00 | 7.77 |
| ATOM | 594 | CB | LEU | 76 | 39.537 | 24.660 | 41.205 | 1.00 | 7.33 |
| ATOM | 595 | CG | LEU | 76 | 40.640 | 25.705 | 41.437 | 1.00 | 4.71 |
| ATOM | 596 | CD1 | LEU | 76 | 41.961 | 25.218 | 40.861 | 1.00 | 3.93 |
| ATOM | 597 | CD2 | LEU | 76 | 40.257 | 27.038 | 40.857 | 1.00 | 7.52 |
| ATOM | 598 | C | LEU | 76 | 39.614 | 23.683 | 43.527 | 1.00 | 8.83 |
| ATOM | 599 | O | LEU | 76 | 38.896 | 24.560 | 43.956 | 1.00 | 10.55 |
| ATOM | 600 | N | ILE | 77 | 40.247 | 22.867 | 44.342 | 1.00 | 8.82 |
| ATOM | 601 | CA | ILE | 77 | 40.215 | 23.024 | 45.796 | 1.00 | 11.03 |
| ATOM | 602 | CB | ILE | 77 | 40.001 | 21.637 | 46.472 | 1.00 | 10.29 |
| ATOM | 603 | CG1 | ILE | 77 | 38.674 | 21.025 | 46.000 | 1.00 | 9.23 |
| ATOM | 604 | CD1 | ILE | 77 | 38.561 | 19.534 | 46.388 | 1.00 | 7.45 |
| ATOM | 605 | CG2 | ILE | 77 | 39.946 | 21.906 | 48.012 | 1.00 | 11.93 |

TABLE 1-continued

Structure Coordinates for *S. aureus* pdf

| ATOM | 606 | C | ILE | 77 | 41.570 | 23.599 | 46.247 | 1.00 | 11.22 |
|---|---|---|---|---|---|---|---|---|---|
| ATOM | 607 | O | ILE | 77 | 42.605 | 22.996 | 46.058 | 1.00 | 11.78 |
| ATOM | 608 | N | PRO | 78 | 41.549 | 24.801 | 46.769 | 1.00 | 12.81 |
| ATOM | 609 | CA | PRO | 78 | 42.755 | 25.478 | 47.215 | 1.00 | 13.82 |
| ATOM | 610 | CB | PRO | 78 | 42.281 | 26.881 | 47.476 | 1.00 | 13.82 |
| ATOM | 611 | CG | PRO | 78 | 40.832 | 26.828 | 47.688 | 1.00 | 13.52 |
| ATOM | 612 | CD | PRO | 78 | 40.323 | 25.600 | 47.015 | 1.00 | 13.68 |
| ATOM | 613 | C | PRO | 78 | 43.384 | 24.865 | 48.463 | 1.00 | 14.04 |
| ATOM | 614 | O | PRO | 78 | 42.729 | 24.162 | 49.225 | 1.00 | 13.74 |
| ATOM | 615 | N | ASP | 79 | 44.663 | 25.190 | 48.665 | 1.00 | 15.66 |
| ATOM | 616 | CA | ASP | 79 | 45.421 | 24.733 | 49.796 | 1.00 | 16.97 |
| ATOM | 617 | CB | ASP | 79 | 46.815 | 25.342 | 49.773 | 1.00 | 17.17 |
| ATOM | 618 | CG | ASP | 79 | 47.725 | 24.835 | 50.845 | 1.00 | 19.81 |
| ATOM | 619 | OD1 | ASP | 79 | 47.281 | 24.237 | 51.833 | 1.00 | 21.59 |
| ATOM | 620 | OD2 | ASP | 79 | 48.968 | 24.997 | 50.743 | 1.00 | 23.71 |
| ATOM | 621 | C | ASP | 79 | 44.730 | 25.095 | 51.103 | 1.00 | 19.47 |
| ATOM | 622 | O | ASP | 79 | 44.386 | 26.257 | 51.328 | 1.00 | 19.81 |
| ATOM | 623 | N | ASP | 80 | 44.523 | 24.114 | 51.958 | 1.00 | 21.56 |
| ATOM | 624 | CA | ASP | 80 | 43.899 | 24.283 | 53.240 | 1.00 | 24.85 |
| ATOM | 625 | CB | ASP | 80 | 43.294 | 22.944 | 53.706 | 1.00 | 27.72 |
| ATOM | 626 | CG | ASP | 80 | 44.345 | 21.869 | 53.833 | 1.00 | 30.53 |
| ATOM | 627 | OD1 | ASP | 80 | 44.094 | 20.790 | 54.401 | 1.00 | 32.70 |
| ATOM | 628 | OD2 | ASP | 80 | 45.490 | 22.015 | 53.347 | 1.00 | 30.54 |
| ATOM | 629 | C | ASP | 80 | 44.898 | 24.740 | 54.318 | 1.00 | 26.28 |
| ATOM | 630 | O | ASP | 80 | 44.491 | 25.228 | 55.374 | 1.00 | 27.81 |
| ATOM | 631 | N | GLY | 81 | 46.168 | 24.602 | 54.112 | 1.00 | 26.90 |
| ATOM | 632 | CA | GLY | 81 | 47.214 | 24.943 | 55.079 | 1.00 | 27.17 |
| ATOM | 633 | C | GLY | 81 | 48.062 | 23.658 | 55.240 | 1.00 | 27.82 |
| ATOM | 634 | O | GLY | 81 | 49.259 | 23.728 | 55.546 | 1.00 | 28.21 |
| ATOM | 635 | N | SER | 82 | 47.391 | 22.520 | 54.989 | 1.00 | 27.02 |
| ATOM | 636 | CA | SER | 82 | 48.108 | 21.246 | 55.049 | 1.00 | 26.04 |
| ATOM | 637 | CB | SER | 82 | 47.248 | 20.019 | 54.796 | 1.00 | 25.15 |
| ATOM | 638 | OG | SER | 82 | 46.765 | 20.059 | 53.446 | 1.00 | 26.13 |
| ATOM | 639 | C | SER | 82 | 49.127 | 21.195 | 53.882 | 1.00 | 24.89 |
| ATOM | 640 | O | SER | 82 | 50.066 | 20.426 | 53.980 | 1.00 | 25.62 |
| ATOM | 641 | N | GLY | 83 | 48.917 | 22.012 | 52.872 | 1.00 | 23.48 |
| ATOM | 642 | CA | GLY | 83 | 49.841 | 21.974 | 51.719 | 1.00 | 21.77 |
| ATOM | 643 | C | GLY | 83 | 49.163 | 21.092 | 50.638 | 1.00 | 19.26 |
| ATOM | 644 | O | GLY | 83 | 49.801 | 20.902 | 49.631 | 1.00 | 20.21 |
| ATOM | 645 | N | LYS | 84 | 47.972 | 20.576 | 50.867 | 1.00 | 16.73 |
| ATOM | 646 | CA | LYS | 84 | 47.296 | 19.797 | 49.836 | 1.00 | 14.79 |
| ATOM | 647 | CB | LYS | 84 | 46.528 | 18.644 | 50.415 | 1.00 | 16.65 |
| ATOM | 648 | CG | LYS | 84 | 47.294 | 17.703 | 51.325 | 1.00 | 20.53 |
| ATOM | 649 | CD | LYS | 84 | 46.320 | 16.536 | 51.571 | 1.00 | 26.25 |
| ATOM | 650 | CE | LYS | 84 | 46.765 | 15.630 | 52.681 | 1.00 | 29.35 |
| ATOM | 651 | NZ | LYS | 84 | 46.698 | 16.382 | 53.997 | 1.00 | 31.51 |
| ATOM | 652 | C | LYS | 84 | 46.305 | 20.645 | 49.058 | 1.00 | 13.36 |
| ATOM | 653 | O | LYS | 84 | 45.482 | 21.354 | 49.657 | 1.00 | 13.57 |
| ATOM | 654 | N | SER | 85 | 46.334 | 20.575 | 47.727 | 1.00 | 12.20 |
| ATOM | 655 | CA | SER | 85 | 45.399 | 21.352 | 46.904 | 1.00 | 10.79 |
| ATOM | 656 | CB | SER | 85 | 45.910 | 22.713 | 46.473 | 1.00 | 10.03 |
| ATOM | 657 | OG | SER | 85 | 46.979 | 22.545 | 45.587 | 1.00 | 12.27 |
| ATOM | 658 | C | SER | 85 | 45.052 | 20.517 | 45.660 | 1.00 | 9.97 |
| ATOM | 659 | O | SER | 85 | 45.892 | 19.710 | 45.314 | 1.00 | 9.45 |
| ATOM | 660 | N | TYR | 86 | 43.855 | 20.667 | 45.136 | 1.00 | 8.93 |
| ATOM | 661 | CA | TYR | 86 | 43.370 | 19.823 | 44.040 | 1.00 | 8.91 |
| ATOM | 662 | CB | TYR | 86 | 42.190 | 18.985 | 44.568 | 1.00 | 9.61 |
| ATOM | 663 | CG | TYR | 86 | 42.612 | 18.127 | 45.766 | 1.00 | 11.87 |
| ATOM | 664 | CD1 | TYR | 86 | 42.525 | 18.675 | 47.031 | 1.00 | 12.22 |
| ATOM | 665 | CE1 | TYR | 86 | 42.968 | 17.980 | 48.146 | 1.00 | 14.09 |
| ATOM | 666 | CZ | TYR | 86 | 43.464 | 16.693 | 47.998 | 1.00 | 13.74 |
| ATOM | 667 | OH | TYR | 86 | 43.877 | 16.050 | 49.147 | 1.00 | 14.04 |
| ATOM | 668 | CE2 | TYR | 86 | 43.587 | 16.139 | 46.747 | 1.00 | 13.17 |
| ATOM | 669 | CD2 | TYR | 86 | 43.136 | 16.849 | 45.631 | 1.00 | 12.81 |
| ATOM | 670 | C | TYR | 86 | 42.937 | 20.636 | 42.843 | 1.00 | 8.39 |
| ATOM | 671 | O | TYR | 86 | 42.041 | 21.470 | 42.905 | 1.00 | 11.10 |
| ATOM | 672 | N | ASP | 87 | 43.597 | 20.487 | 41.740 | 1.00 | 7.58 |
| ATOM | 673 | CA | ASP | 87 | 43.388 | 21.198 | 40.491 | 1.00 | 7.93 |
| ATOM | 674 | CB | ASP | 87 | 44.561 | 22.172 | 40.249 | 1.00 | 7.54 |
| ATOM | 675 | CG | ASP | 87 | 44.336 | 23.088 | 39.060 | 1.00 | 9.36 |
| ATOM | 676 | OD1 | ASP | 87 | 43.367 | 22.912 | 38.300 | 1.00 | 9.22 |
| ATOM | 677 | OD2 | ASP | 87 | 45.098 | 24.043 | 38.908 | 1.00 | 12.88 |
| ATOM | 678 | C | ASP | 87 | 43.369 | 20.124 | 39.392 | 1.00 | 6.63 |
| ATOM | 679 | O | ASP | 87 | 44.445 | 19.695 | 38.965 | 1.00 | 7.41 |
| ATOM | 680 | N | TYR | 88 | 42.204 | 19.657 | 39.046 | 1.00 | 7.18 |
| ATOM | 681 | CA | TYR | 88 | 42.058 | 18.612 | 38.048 | 1.00 | 7.88 |
| ATOM | 682 | CB | TYR | 88 | 41.775 | 17.252 | 38.727 | 1.00 | 8.03 |

TABLE 1-continued

Structure Coordinates for S. aureus pdf

| ATOM | 683 | CG  | TYR | 88 | 42.918 | 16.706 | 39.528 | 1.00 | 7.31  |
|------|-----|-----|-----|----|--------|--------|--------|------|-------|
| ATOM | 684 | CD1 | TYR | 88 | 43.051 | 16.986 | 40.887 | 1.00 | 7.10  |
| ATOM | 685 | CE1 | TYR | 88 | 44.093 | 16.455 | 41.622 | 1.00 | 5.16  |
| ATOM | 686 | CZ  | TYR | 88 | 45.017 | 15.649 | 40.992 | 1.00 | 5.90  |
| ATOM | 687 | OH  | TYR | 88 | 46.088 | 15.153 | 41.721 | 1.00 | 7.39  |
| ATOM | 688 | CE2 | TYR | 88 | 44.955 | 15.404 | 39.643 | 1.00 | 6.03  |
| ATOM | 689 | CD2 | TYR | 88 | 43.866 | 15.894 | 38.917 | 1.00 | 6.97  |
| ATOM | 690 | C   | TYR | 88 | 40.939 | 18.810 | 37.051 | 1.00 | 8.22  |
| ATOM | 691 | O   | TYR | 88 | 39.816 | 19.193 | 37.355 | 1.00 | 9.63  |
| ATOM | 692 | N   | MET | 89 | 41.231 | 18.498 | 35.814 | 1.00 | 8.89  |
| ATOM | 693 | CA  | MET | 89 | 40.233 | 18.533 | 34.736 | 1.00 | 8.17  |
| ATOM | 694 | CB  | MET | 89 | 40.600 | 19.441 | 33.591 | 1.00 | 7.98  |
| ATOM | 695 | CG  | MET | 89 | 40.522 | 20.918 | 33.852 | 1.00 | 8.05  |
| ATOM | 696 | SD  | MET | 89 | 41.005 | 21.973 | 32.496 | 1.00 | 8.41  |
| ATOM | 697 | CE  | MET | 89 | 42.746 | 21.671 | 32.340 | 1.00 | 7.64  |
| ATOM | 698 | C   | MET | 89 | 40.203 | 17.038 | 34.319 | 1.00 | 5.98  |
| ATOM | 699 | O   | MET | 89 | 41.212 | 16.525 | 33.797 | 1.00 | 6.63  |
| ATOM | 700 | N   | LEU | 90 | 39.123 | 16.386 | 34.611 | 1.00 | 4.43  |
| ATOM | 701 | CA  | LEU | 90 | 39.050 | 14.952 | 34.284 | 1.00 | 5.33  |
| ATOM | 702 | CB  | LEU | 90 | 38.707 | 14.179 | 35.541 | 1.00 | 6.25  |
| ATOM | 703 | CG  | LEU | 90 | 39.564 | 14.222 | 36.755 | 1.00 | 6.92  |
| ATOM | 704 | CD1 | LEU | 90 | 39.034 | 13.233 | 37.827 | 1.00 | 4.71  |
| ATOM | 705 | CD2 | LEU | 90 | 41.018 | 13.889 | 36.453 | 1.00 | 6.93  |
| ATOM | 706 | C   | LEU | 90 | 38.027 | 14.648 | 33.196 | 1.00 | 4.75  |
| ATOM | 707 | O   | LEU | 90 | 36.963 | 15.237 | 33.151 | 1.00 | 5.61  |
| ATOM | 708 | N   | VAL | 91 | 38.354 | 13.719 | 32.348 | 1.00 | 4.98  |
| ATOM | 709 | CA  | VAL | 91 | 37.487 | 13.246 | 31.253 | 1.00 | 4.58  |
| ATOM | 710 | CB  | VAL | 91 | 38.323 | 13.299 | 29.938 | 1.00 | 4.51  |
| ATOM | 711 | CG1 | VAL | 91 | 37.590 | 12.571 | 28.815 | 1.00 | 6.97  |
| ATOM | 712 | CG2 | VAL | 91 | 38.589 | 14.718 | 29.522 | 1.00 | 2.32  |
| ATOM | 713 | C   | VAL | 91 | 37.137 | 11.805 | 31.576 | 1.00 | 5.04  |
| ATOM | 714 | O   | VAL | 91 | 38.003 | 11.030 | 31.991 | 1.00 | 5.81  |
| ATOM | 715 | N   | ASN | 92 | 35.842 | 11.420 | 31.481 | 1.00 | 5.85  |
| ATOM | 716 | CA  | ASN | 92 | 35.357 | 10.088 | 31.747 | 1.00 | 6.19  |
| ATOM | 717 | CB  | ASN | 92 | 35.743 | 9.111  | 30.644 | 1.00 | 7.29  |
| ATOM | 718 | CG  | ASN | 92 | 35.308 | 9.457  | 29.252 | 1.00 | 7.92  |
| ATOM | 719 | OD1 | ASN | 92 | 34.247 | 10.045 | 29.090 | 1.00 | 7.73  |
| ATOM | 720 | ND2 | ASN | 92 | 36.092 | 9.017  | 28.271 | 1.00 | 10.17 |
| ATOM | 721 | C   | ASN | 92 | 35.756 | 9.501  | 33.083 | 1.00 | 8.19  |
| ATOM | 722 | O   | ASN | 92 | 36.265 | 8.363  | 33.177 | 1.00 | 9.98  |
| ATOM | 723 | N   | PRO | 93 | 35.644 | 10.283 | 34.153 | 1.00 | 8.97  |
| ATOM | 724 | CD  | PRO | 93 | 35.059 | 11.684 | 34.132 | 1.00 | 7.81  |
| ATOM | 725 | CA  | PRO | 93 | 35.996 | 9.859  | 35.482 | 1.00 | 8.04  |
| ATOM | 726 | CB  | PRO | 93 | 35.928 | 11.155 | 36.272 | 1.00 | 7.31  |
| ATOM | 727 | CG  | PRO | 93 | 34.802 | 11.890 | 35.596 | 1.00 | 7.53  |
| ATOM | 728 | C   | PRO | 93 | 35.074 | 8.770  | 35.997 | 1.00 | 9.49  |
| ATOM | 729 | O   | PRO | 93 | 33.852 | 8.750  | 35.756 | 1.00 | 9.28  |
| ATOM | 730 | N   | LYS | 94 | 35.690 | 7.828  | 36.740 | 1.00 | 9.93  |
| ATOM | 731 | CA  | LYS | 94 | 34.921 | 6.724  | 37.302 | 1.00 | 9.81  |
| ATOM | 732 | CB  | LYS | 94 | 34.975 | 5.537  | 36.280 | 1.00 | 13.20 |
| ATOM | 733 | CG  | LYS | 94 | 33.920 | 4.483  | 36.579 | 1.00 | 18.63 |
| ATOM | 734 | CD  | LYS | 94 | 34.020 | 3.251  | 35.668 | 1.00 | 23.45 |
| ATOM | 735 | CE  | LYS | 94 | 32.846 | 2.297  | 35.911 | 1.00 | 25.89 |
| ATOM | 736 | NZ  | LYS | 94 | 32.998 | 1.075  | 35.012 | 1.00 | 28.49 |
| ATOM | 737 | C   | LYS | 94 | 35.539 | 6.242  | 38.610 | 1.00 | 8.51  |
| ATOM | 738 | O   | LYS | 94 | 36.749 | 6.036  | 38.748 | 1.00 | 6.81  |
| ATOM | 739 | N   | ILE | 95 | 34.686 | 6.078  | 39.604 | 1.00 | 7.95  |
| ATOM | 740 | CA  | ILE | 95 | 35.040 | 5.534  | 40.910 | 1.00 | 6.10  |
| ATOM | 741 | CB  | ILE | 95 | 34.014 | 5.898  | 41.954 | 1.00 | 5.18  |
| ATOM | 742 | CG1 | ILE | 95 | 34.046 | 7.444  | 42.211 | 1.00 | 6.06  |
| ATOM | 743 | CD1 | ILE | 95 | 32.837 | 7.904  | 43.045 | 1.00 | 5.94  |
| ATOM | 744 | CG2 | ILE | 95 | 34.329 | 5.157  | 43.281 | 1.00 | 5.58  |
| ATOM | 745 | C   | ILE | 95 | 35.166 | 3.997  | 40.716 | 1.00 | 6.29  |
| ATOM | 746 | O   | ILE | 95 | 34.198 | 3.309  | 40.347 | 1.00 | 5.34  |
| ATOM | 747 | N   | VAL | 96 | 36.391 | 3.492  | 40.859 | 1.00 | 4.94  |
| ATOM | 748 | CA  | VAL | 96 | 36.632 | 2.073  | 40.636 | 1.00 | 5.84  |
| ATOM | 749 | CB  | VAL | 96 | 37.831 | 1.745  | 39.776 | 1.00 | 5.80  |
| ATOM | 750 | CG1 | VAL | 96 | 37.679 | 2.310  | 38.351 | 1.00 | 6.24  |
| ATOM | 751 | CG2 | VAL | 96 | 39.165 | 2.258  | 40.318 | 1.00 | 5.22  |
| ATOM | 752 | C   | VAL | 96 | 36.608 | 1.295  | 41.950 | 1.00 | 5.83  |
| ATOM | 753 | O   | VAL | 96 | 36.279 | 0.126  | 41.914 | 1.00 | 5.47  |
| ATOM | 754 | N   | SER | 97 | 36.847 | 1.959  | 43.077 | 1.00 | 5.14  |
| ATOM | 755 | CA  | SER | 97 | 36.830 | 1.376  | 44.383 | 1.00 | 5.56  |
| ATOM | 756 | CB  | SER | 97 | 38.128 | 0.683  | 44.766 | 1.00 | 3.06  |
| ATOM | 757 | OG  | SER | 97 | 39.236 | 1.451  | 44.594 | 1.00 | 6.94  |
| ATOM | 758 | C   | SER | 97 | 36.592 | 2.485  | 45.447 | 1.00 | 6.21  |
| ATOM | 759 | O   | SER | 97 | 36.842 | 3.650  | 45.154 | 1.00 | 5.16  |

TABLE 1-continued

Structure Coordinates for S. aureus pdf

| ATOM | 760 | N | HIS | 98 | 36.080 | 2.045 | 46.577 | 1.00 | 5.51 |
|------|-----|-----|-----|-----|--------|--------|--------|------|-------|
| ATOM | 761 | CA | HIS | 98 | 35.807 | 2.912 | 47.695 | 1.00 | 6.19 |
| ATOM | 762 | CB | HIS | 98 | 34.521 | 3.705 | 47.410 | 1.00 | 5.68 |
| ATOM | 763 | CG | HIS | 98 | 33.314 | 2.839 | 47.189 | 1.00 | 3.10 |
| ATOM | 764 | ND1 | HIS | 98 | 32.540 | 2.415 | 48.249 | 1.00 | 5.80 |
| ATOM | 765 | CE1 | HIS | 98 | 31.533 | 1.690 | 47.820 | 1.00 | 3.91 |
| ATOM | 766 | NE2 | HIS | 98 | 31.630 | 1.631 | 46.504 | 1.00 | 4.11 |
| ATOM | 767 | CD2 | HIS | 98 | 32.731 | 2.333 | 46.100 | 1.00 | 2.55 |
| ATOM | 768 | C | HIS | 98 | 35.718 | 2.187 | 49.043 | 1.00 | 6.46 |
| ATOM | 769 | O | HIS | 98 | 35.484 | 0.998 | 49.174 | 1.00 | 5.57 |
| ATOM | 770 | N | SER | 99 | 35.882 | 2.968 | 50.123 | 1.00 | 6.76 |
| ATOM | 771 | CA | SER | 99 | 35.744 | 2.476 | 51.476 | 1.00 | 6.43 |
| ATOM | 772 | CB | SER | 99 | 36.188 | 3.588 | 52.459 | 1.00 | 7.38 |
| ATOM | 773 | OG | SER | 99 | 35.341 | 4.757 | 52.354 | 1.00 | 7.60 |
| ATOM | 774 | C | SER | 99 | 34.290 | 2.177 | 51.765 | 1.00 | 6.67 |
| ATOM | 775 | O | SER | 99 | 33.365 | 2.734 | 51.153 | 1.00 | 7.55 |
| ATOM | 776 | N | VAL | 100 | 34.005 | 1.310 | 52.714 | 1.00 | 6.58 |
| ATOM | 777 | CA | VAL | 100 | 32.615 | 1.043 | 53.160 | 1.00 | 6.28 |
| ATOM | 778 | CB | VAL | 100 | 32.598 | −0.278 | 53.971 | 1.00 | 6.35 |
| ATOM | 779 | CG1 | VAL | 100 | 31.215 | −0.420 | 54.605 | 1.00 | 6.97 |
| ATOM | 780 | CG2 | VAL | 100 | 32.745 | −1.461 | 52.932 | 1.00 | 6.04 |
| ATOM | 781 | C | VAL | 100 | 32.175 | 2.219 | 54.062 | 1.00 | 6.51 |
| ATOM | 782 | O | VAL | 100 | 31.049 | 2.745 | 54.044 | 1.00 | 6.77 |
| ATOM | 783 | N | GLN | 101 | 33.124 | 2.741 | 54.816 | 1.00 | 7.40 |
| ATOM | 784 | CA | GLN | 101 | 32.865 | 3.871 | 55.734 | 1.00 | 9.68 |
| ATOM | 785 | CB | GLN | 101 | 34.012 | 4.032 | 56.704 | 1.00 | 9.29 |
| ATOM | 786 | CG | GLN | 101 | 33.909 | 5.192 | 57.649 | 1.00 | 9.97 |
| ATOM | 787 | CD | GLN | 101 | 35.017 | 5.329 | 58.642 | 1.00 | 10.63 |
| ATOM | 788 | OE1 | GLN | 101 | 36.190 | 5.548 | 58.257 | 1.00 | 13.55 |
| ATOM | 789 | NE2 | GLN | 101 | 34.656 | 5.267 | 59.887 | 1.00 | 11.28 |
| ATOM | 790 | C | GLN | 101 | 32.569 | 5.189 | 54.993 | 1.00 | 9.37 |
| ATOM | 791 | O | GLN | 101 | 33.236 | 5.551 | 54.068 | 1.00 | 7.54 |
| ATOM | 792 | N | GLU | 102 | 31.480 | 5.845 | 55.472 | 1.00 | 9.24 |
| ATOM | 793 | CA | GLU | 102 | 31.008 | 7.074 | 54.921 | 1.00 | 9.90 |
| ATOM | 794 | CB | GLU | 102 | 29.464 | 7.141 | 55.018 | 1.00 | 11.63 |
| ATOM | 795 | CG | GLU | 102 | 28.763 | 6.013 | 54.261 | 1.00 | 12.22 |
| ATOM | 796 | CD | GLU | 102 | 27.278 | 6.126 | 54.402 | 1.00 | 14.95 |
| ATOM | 797 | OE1 | GLU | 102 | 26.805 | 6.596 | 55.462 | 1.00 | 18.92 |
| ATOM | 798 | OE2 | GLU | 102 | 26.511 | 5.770 | 53.500 | 1.00 | 16.02 |
| ATOM | 799 | C | GLU | 102 | 31.533 | 8.340 | 55.593 | 1.00 | 10.50 |
| ATOM | 800 | O | GLU | 102 | 32.169 | 8.275 | 56.630 | 1.00 | 11.22 |
| ATOM | 801 | N | ALA | 103 | 31.273 | 9.485 | 54.974 | 1.00 | 9.97 |
| ATOM | 802 | CA | ALA | 103 | 31.699 | 10.772 | 55.541 | 1.00 | 9.74 |
| ATOM | 803 | CB | ALA | 103 | 33.049 | 11.245 | 55.034 | 1.00 | 8.10 |
| ATOM | 804 | C | ALA | 103 | 30.644 | 11.816 | 55.123 | 1.00 | 9.71 |
| ATOM | 805 | O | ALA | 103 | 30.011 | 11.529 | 54.129 | 1.00 | 9.34 |
| ATOM | 806 | N | TYR | 104 | 30.556 | 12.936 | 55.808 | 1.00 | 9.87 |
| ATOM | 807 | CA | TYR | 104 | 29.585 | 13.984 | 55.438 | 1.00 | 11.04 |
| ATOM | 808 | CB | TYR | 104 | 28.192 | 13.707 | 56.083 | 1.00 | 11.01 |
| ATOM | 809 | CG | TYR | 104 | 28.273 | 13.737 | 57.596 | 1.00 | 12.87 |
| ATOM | 810 | CD1 | TYR | 104 | 27.958 | 14.884 | 58.330 | 1.00 | 14.01 |
| ATOM | 811 | CE1 | TYR | 104 | 28.088 | 14.909 | 59.727 | 1.00 | 13.96 |
| ATOM | 812 | CZ | TYR | 104 | 28.519 | 13.774 | 60.389 | 1.00 | 14.95 |
| ATOM | 813 | OH | TYR | 104 | 28.676 | 13.775 | 61.757 | 1.00 | 15.04 |
| ATOM | 814 | CE2 | TYR | 104 | 28.796 | 12.619 | 59.685 | 1.00 | 13.61 |
| ATOM | 815 | CD2 | TYR | 104 | 28.665 | 12.589 | 58.310 | 1.00 | 13.25 |
| ATOM | 816 | C | TYR | 104 | 30.135 | 15.342 | 55.885 | 1.00 | 10.66 |
| ATOM | 817 | O | TYR | 104 | 30.942 | 15.394 | 56.853 | 1.00 | 11.97 |
| ATOM | 818 | N | LEU | 105 | 29.819 | 16.416 | 55.227 | 1.00 | 10.31 |
| ATOM | 819 | CA | LEU | 105 | 30.271 | 17.775 | 55.675 | 1.00 | 10.31 |
| ATOM | 820 | CB | LEU | 105 | 30.363 | 18.745 | 54.499 | 1.00 | 8.28 |
| ATOM | 821 | CG | LEU | 105 | 31.202 | 18.355 | 53.295 | 1.00 | 7.12 |
| ATOM | 822 | CD1 | LEU | 105 | 31.189 | 19.393 | 52.190 | 1.00 | 5.52 |
| ATOM | 823 | CD2 | LEU | 105 | 32.669 | 18.076 | 53.663 | 1.00 | 5.12 |
| ATOM | 824 | C | LEU | 105 | 29.156 | 18.174 | 56.667 | 1.00 | 10.48 |
| ATOM | 825 | O | LEU | 105 | 27.977 | 17.998 | 56.358 | 1.00 | 10.24 |
| ATOM | 826 | N | PRO | 106 | 29.469 | 18.627 | 57.865 | 1.00 | 11.95 |
| ATOM | 827 | CA | PRO | 106 | 28.454 | 18.963 | 58.863 | 1.00 | 12.84 |
| ATOM | 828 | CB | PRO | 106 | 29.276 | 19.275 | 60.093 | 1.00 | 13.00 |
| ATOM | 829 | CG | PRO | 106 | 30.549 | 19.799 | 59.534 | 1.00 | 14.02 |
| ATOM | 830 | CD | PRO | 106 | 30.826 | 18.911 | 58.327 | 1.00 | 13.21 |
| ATOM | 831 | C | PRO | 106 | 27.479 | 20.038 | 58.465 | 1.00 | 13.69 |
| ATOM | 832 | O | PRO | 106 | 26.376 | 20.106 | 59.000 | 1.00 | 14.91 |
| ATOM | 833 | N | THR | 107 | 27.838 | 20.930 | 57.523 | 1.00 | 14.66 |
| ATOM | 834 | CA | THR | 107 | 26.983 | 21.976 | 57.008 | 1.00 | 16.19 |
| ATOM | 835 | CB | THR | 107 | 27.799 | 23.235 | 56.607 | 1.00 | 21.67 |
| ATOM | 836 | OG1 | THR | 107 | 28.885 | 22.852 | 55.716 | 1.00 | 25.40 |

TABLE 1-continued

Structure Coordinates for *S. aureus* pdf

| ATOM | 837 | CG2 | THR | 107 | 28.349 | 23.915 | 57.844 | 1.00 | 24.07 |
|------|-----|-----|-----|-----|--------|--------|--------|------|-------|
| ATOM | 838 | C | THR | 107 | 26.199 | 21.591 | 55.752 | 1.00 | 13.84 |
| ATOM | 839 | O | THR | 107 | 25.549 | 22.430 | 55.155 | 1.00 | 14.95 |
| ATOM | 840 | N | GLY | 108 | 26.232 | 20.326 | 55.368 | 1.00 | 11.38 |
| ATOM | 841 | CA | GLY | 108 | 25.547 | 19.869 | 54.176 | 1.00 | 8.51 |
| ATOM | 842 | C | GLY | 108 | 26.402 | 20.337 | 53.000 | 1.00 | 7.43 |
| ATOM | 843 | O | GLY | 108 | 27.611 | 20.629 | 53.127 | 1.00 | 7.41 |
| ATOM | 844 | N | GLU | 109 | 25.808 | 20.388 | 51.837 | 1.00 | 6.61 |
| ATOM | 845 | CA | GLU | 109 | 26.466 | 20.806 | 50.634 | 1.00 | 7.52 |
| ATOM | 846 | CB | GLU | 109 | 26.686 | 19.615 | 49.685 | 1.00 | 7.66 |
| ATOM | 847 | CG | GLU | 109 | 27.582 | 18.521 | 50.288 | 1.00 | 5.52 |
| ATOM | 848 | CD | GLU | 109 | 27.731 | 17.381 | 49.320 | 1.00 | 7.26 |
| ATOM | 849 | OE1 | GLU | 109 | 27.368 | 17.478 | 48.139 | 1.00 | 7.28 |
| ATOM | 850 | OE2 | GLU | 109 | 28.195 | 16.298 | 49.739 | 1.00 | 8.58 |
| ATOM | 851 | C | GLU | 109 | 25.653 | 21.884 | 49.896 | 1.00 | 8.48 |
| ATOM | 852 | O | GLU | 109 | 24.554 | 22.191 | 50.241 | 1.00 | 10.22 |
| ATOM | 853 | N | GLY | 110 | 26.303 | 22.414 | 48.883 | 1.00 | 10.01 |
| ATOM | 854 | CA | GLY | 110 | 25.702 | 23.424 | 47.989 | 1.00 | 10.84 |
| ATOM | 855 | C | GLY | 110 | 26.178 | 23.098 | 46.548 | 1.00 | 11.21 |
| ATOM | 856 | O | GLY | 110 | 27.056 | 22.281 | 46.342 | 1.00 | 11.00 |
| ATOM | 857 | N | CYS | 111 | 25.608 | 23.776 | 45.582 | 1.00 | 11.21 |
| ATOM | 858 | CA | CYS | 111 | 25.870 | 23.582 | 44.163 | 1.00 | 10.09 |
| ATOM | 859 | C | CYS | 111 | 25.533 | 24.848 | 43.352 | 1.00 | 10.36 |
| ATOM | 860 | O | CYS | 111 | 24.562 | 25.536 | 43.627 | 1.00 | 10.29 |
| ATOM | 861 | CB | CYS | 111 | 24.923 | 22.434 | 43.721 | 1.00 | 9.84 |
| ATOM | 862 | SG | CYS | 111 | 25.048 | 21.924 | 42.045 | 1.00 | 8.95 |
| ATOM | 863 | N | LEU | 112 | 26.398 | 25.177 | 42.403 | 1.00 | 11.20 |
| ATOM | 864 | CA | LEU | 112 | 26.170 | 26.384 | 41.550 | 1.00 | 11.83 |
| ATOM | 865 | CB | LEU | 112 | 27.411 | 26.486 | 40.666 | 1.00 | 12.57 |
| ATOM | 866 | CG | LEU | 112 | 28.708 | 26.878 | 41.352 | 1.00 | 15.06 |
| ATOM | 867 | CD1 | LEU | 112 | 29.871 | 26.352 | 40.469 | 1.00 | 15.77 |
| ATOM | 868 | CD2 | LEU | 112 | 28.926 | 28.394 | 41.340 | 1.00 | 15.61 |
| ATOM | 869 | C | LEU | 112 | 24.851 | 26.350 | 40.836 | 1.00 | 11.60 |
| ATOM | 870 | O | LEU | 112 | 24.228 | 27.383 | 40.488 | 1.00 | 11.36 |
| ATOM | 871 | N | SER | 113 | 24.310 | 25.146 | 40.587 | 1.00 | 11.85 |
| ATOM | 872 | CA | SER | 113 | 23.048 | 24.950 | 39.917 | 1.00 | 11.15 |
| ATOM | 873 | CB | SER | 113 | 23.025 | 23.699 | 39.049 | 1.00 | 10.66 |
| ATOM | 874 | OG | SER | 113 | 23.968 | 23.793 | 37.992 | 1.00 | 7.38 |
| ATOM | 875 | C | SER | 113 | 21.886 | 24.945 | 40.885 | 1.00 | 12.54 |
| ATOM | 876 | O | SER | 113 | 20.731 | 24.917 | 40.427 | 1.00 | 14.05 |
| ATOM | 877 | N | VAL | 114 | 22.143 | 24.975 | 42.198 | 1.00 | 11.90 |
| ATOM | 878 | CA | VAL | 114 | 21.022 | 25.016 | 43.143 | 1.00 | 11.54 |
| ATOM | 879 | CB | VAL | 114 | 21.067 | 23.872 | 44.160 | 1.00 | 9.05 |
| ATOM | 880 | CG1 | VAL | 114 | 19.777 | 23.919 | 45.007 | 1.00 | 10.95 |
| ATOM | 881 | CG2 | VAL | 114 | 21.080 | 22.538 | 43.409 | 1.00 | 9.28 |
| ATOM | 882 | C | VAL | 114 | 21.005 | 26.402 | 43.818 | 1.00 | 11.42 |
| ATOM | 883 | O | VAL | 114 | 21.854 | 26.663 | 44.630 | 1.00 | 11.25 |
| ATOM | 884 | N | ASP | 115 | 20.077 | 27.277 | 43.466 | 1.00 | 12.74 |
| ATOM | 885 | CA | ASP | 115 | 20.012 | 28.618 | 43.985 | 1.00 | 15.39 |
| ATOM | 886 | CB | ASP | 115 | 19.029 | 29.540 | 43.310 | 1.00 | 17.73 |
| ATOM | 887 | CG | ASP | 115 | 19.300 | 29.933 | 41.893 | 1.00 | 20.05 |
| ATOM | 888 | OD1 | ASP | 115 | 20.331 | 29.598 | 41.312 | 1.00 | 18.80 |
| ATOM | 889 | OD2 | ASP | 115 | 18.380 | 30.637 | 41.372 | 1.00 | 22.85 |
| ATOM | 890 | C | ASP | 115 | 19.789 | 28.760 | 45.492 | 1.00 | 16.27 |
| ATOM | 891 | O | ASP | 115 | 20.405 | 29.626 | 46.099 | 1.00 | 17.11 |
| ATOM | 892 | N | ASP | 116 | 18.857 | 28.001 | 46.028 | 1.00 | 17.25 |
| ATOM | 893 | CA | ASP | 116 | 18.590 | 28.081 | 47.461 | 1.00 | 18.90 |
| ATOM | 894 | CB | ASP | 116 | 17.117 | 27.717 | 47.739 | 1.00 | 21.30 |
| ATOM | 895 | CG | ASP | 116 | 16.153 | 28.650 | 47.041 | 1.00 | 24.14 |
| ATOM | 896 | OD1 | ASP | 116 | 16.391 | 29.883 | 47.008 | 1.00 | 23.07 |
| ATOM | 897 | OD2 | ASP | 116 | 15.132 | 28.134 | 46.495 | 1.00 | 26.77 |
| ATOM | 898 | C | ASP | 116 | 19.444 | 27.106 | 48.249 | 1.00 | 19.20 |
| ATOM | 899 | O | ASP | 116 | 19.738 | 26.025 | 47.744 | 1.00 | 19.78 |
| ATOM | 900 | N | ASN | 117 | 19.869 | 27.534 | 49.428 | 1.00 | 18.50 |
| ATOM | 901 | CA | ASN | 117 | 20.571 | 26.691 | 50.352 | 1.00 | 18.69 |
| ATOM | 902 | CB | ASN | 117 | 21.143 | 27.363 | 51.585 | 1.00 | 19.43 |
| ATOM | 903 | CG | ASN | 117 | 22.487 | 28.000 | 51.304 | 1.00 | 22.50 |
| ATOM | 904 | OD1 | ASN | 117 | 23.330 | 27.263 | 50.736 | 1.00 | 23.16 |
| ATOM | 905 | ND2 | ASN | 117 | 22.749 | 29.225 | 51.663 | 1.00 | 22.67 |
| ATOM | 906 | C | ASN | 117 | 19.655 | 25.543 | 50.781 | 1.00 | 19.22 |
| ATOM | 907 | O | ASN | 117 | 18.465 | 25.737 | 51.042 | 1.00 | 20.65 |
| ATOM | 908 | N | VAL | 118 | 20.216 | 24.324 | 50.775 | 1.00 | 18.92 |
| ATOM | 909 | CA | VAL | 118 | 19.445 | 23.151 | 51.178 | 1.00 | 18.04 |
| ATOM | 910 | CB | VAL | 118 | 19.364 | 22.090 | 50.077 | 1.00 | 18.23 |
| ATOM | 911 | CG1 | VAL | 118 | 18.474 | 20.906 | 50.480 | 1.00 | 15.62 |
| ATOM | 912 | CG2 | VAL | 118 | 18.797 | 22.712 | 48.813 | 1.00 | 18.51 |
| ATOM | 913 | C | VAL | 118 | 20.133 | 22.575 | 52.422 | 1.00 | 17.95 |

TABLE 1-continued

Structure Coordinates for *S. aureus* pdf

| ATOM | 914 | O | VAL | 118 | 21.338 | 22.351 | 52.430 | 1.00 | 17.23 |
|---|---|---|---|---|---|---|---|---|---|
| ATOM | 915 | N | ALA | 119 | 19.326 | 22.435 | 53.478 | 1.00 | 17.06 |
| ATOM | 916 | CA | ALA | 119 | 19.833 | 21.907 | 54.727 | 1.00 | 17.10 |
| ATOM | 917 | CB | ALA | 119 | 18.932 | 22.450 | 55.851 | 1.00 | 17.38 |
| ATOM | 918 | C | ALA | 119 | 19.739 | 20.368 | 54.722 | 1.00 | 16.72 |
| ATOM | 919 | O | ALA | 119 | 18.760 | 19.858 | 54.161 | 1.00 | 16.13 |
| ATOM | 920 | N | GLY | 120 | 20.718 | 19.683 | 55.320 | 1.00 | 15.41 |
| ATOM | 921 | CA | GLY | 120 | 20.621 | 18.216 | 55.347 | 1.00 | 14.28 |
| ATOM | 922 | C | GLY | 120 | 21.960 | 17.576 | 55.058 | 1.00 | 13.76 |
| ATOM | 923 | O | GLY | 120 | 22.737 | 18.067 | 54.234 | 1.00 | 14.66 |
| ATOM | 924 | N | LEU | 121 | 22.244 | 16.452 | 55.717 | 1.00 | 12.70 |
| ATOM | 925 | CA | LEU | 121 | 23.529 | 15.767 | 55.522 | 1.00 | 11.00 |
| ATOM | 926 | CB | LEU | 121 | 23.882 | 15.004 | 56.781 | 1.00 | 10.76 |
| ATOM | 927 | CG | LEU | 121 | 23.943 | 15.759 | 58.103 | 1.00 | 9.49 |
| ATOM | 928 | CD1 | LEU | 121 | 24.449 | 14.822 | 59.193 | 1.00 | 7.07 |
| ATOM | 929 | CD2 | LEU | 121 | 24.866 | 16.971 | 57.969 | 1.00 | 8.49 |
| ATOM | 930 | C | LEU | 121 | 23.528 | 14.851 | 54.310 | 1.00 | 9.73 |
| ATOM | 931 | O | LEU | 121 | 22.575 | 14.134 | 53.975 | 1.00 | 10.55 |
| ATOM | 932 | N | VAL | 122 | 24.614 | 14.916 | 53.575 | 1.00 | 9.32 |
| ATOM | 933 | CA | VAL | 122 | 24.834 | 14.130 | 52.353 | 1.00 | 8.52 |
| ATOM | 934 | CB | VAL | 122 | 25.063 | 15.033 | 51.127 | 1.00 | 6.54 |
| ATOM | 935 | CG1 | VAL | 122 | 25.255 | 14.183 | 49.858 | 1.00 | 6.34 |
| ATOM | 936 | CG2 | VAL | 122 | 23.909 | 15.992 | 50.882 | 1.00 | 7.19 |
| ATOM | 937 | C | VAL | 122 | 26.025 | 13.196 | 52.613 | 1.00 | 8.38 |
| ATOM | 938 | O | VAL | 122 | 27.194 | 13.572 | 52.554 | 1.00 | 7.49 |
| ATOM | 939 | N | HIS | 123 | 25.693 | 11.961 | 52.933 | 1.00 | 8.70 |
| ATOM | 940 | CA | HIS | 123 | 26.619 | 10.910 | 53.254 | 1.00 | 9.15 |
| ATOM | 941 | CB | HIS | 123 | 25.995 | 9.863 | 54.141 | 1.00 | 8.55 |
| ATOM | 942 | CG | HIS | 123 | 25.490 | 10.280 | 55.476 | 1.00 | 8.68 |
| ATOM | 943 | ND1 | HIS | 123 | 24.164 | 10.635 | 55.678 | 1.00 | 8.01 |
| ATOM | 944 | CE1 | HIS | 123 | 23.986 | 10.913 | 56.974 | 1.00 | 7.33 |
| ATOM | 945 | NE2 | HIS | 123 | 25.156 | 10.789 | 57.597 | 1.00 | 9.84 |
| ATOM | 946 | CD2 | HIS | 123 | 26.079 | 10.374 | 56.687 | 1.00 | 8.51 |
| ATOM | 947 | C | HIS | 123 | 27.238 | 10.273 | 51.992 | 1.00 | 8.74 |
| ATOM | 948 | O | HIS | 123 | 26.548 | 9.818 | 51.133 | 1.00 | 9.79 |
| ATOM | 949 | N | ARG | 124 | 28.544 | 10.295 | 51.908 | 1.00 | 8.30 |
| ATOM | 950 | CA | ARG | 124 | 29.327 | 9.808 | 50.787 | 1.00 | 7.51 |
| ATOM | 951 | CB | ARG | 124 | 29.950 | 11.016 | 50.038 | 1.00 | 6.35 |
| ATOM | 952 | CG | ARG | 124 | 28.857 | 11.950 | 49.441 | 1.00 | 6.41 |
| ATOM | 953 | CD | ARG | 124 | 29.525 | 12.993 | 48.565 | 1.00 | 6.17 |
| ATOM | 954 | NE | ARG | 124 | 28.611 | 13.914 | 47.957 | 1.00 | 6.87 |
| ATOM | 955 | CZ | ARG | 124 | 27.747 | 13.824 | 46.996 | 1.00 | 8.12 |
| ATOM | 956 | NH1 | ARG | 124 | 27.516 | 12.728 | 46.252 | 1.00 | 6.27 |
| ATOM | 957 | NH2 | ARG | 124 | 27.033 | 14.909 | 46.631 | 1.00 | 7.84 |
| ATOM | 958 | C | ARG | 124 | 30.408 | 8.871 | 51.264 | 1.00 | 7.13 |
| ATOM | 959 | O | ARG | 124 | 30.496 | 8.686 | 52.482 | 1.00 | 7.16 |
| ATOM | 960 | N | HIS | 125 | 31.238 | 8.287 | 50.388 | 1.00 | 8.38 |
| ATOM | 961 | CA | HIS | 125 | 32.302 | 7.401 | 50.830 | 1.00 | 9.33 |
| ATOM | 962 | CB | HIS | 125 | 32.816 | 6.389 | 49.794 | 1.00 | 9.69 |
| ATOM | 963 | CG | HIS | 125 | 31.660 | 5.665 | 49.141 | 1.00 | 7.74 |
| ATOM | 964 | ND1 | HIS | 125 | 30.806 | 4.831 | 49.778 | 1.00 | 8.49 |
| ATOM | 965 | CE1 | HIS | 125 | 29.907 | 4.383 | 48.933 | 1.00 | 7.96 |
| ATOM | 966 | NE2 | HIS | 125 | 30.208 | 4.908 | 47.725 | 1.00 | 9.47 |
| ATOM | 967 | CD2 | HIS | 125 | 31.289 | 5.714 | 47.836 | 1.00 | 8.48 |
| ATOM | 968 | C | HIS | 125 | 33.495 | 8.241 | 51.292 | 1.00 | 9.98 |
| ATOM | 969 | O | HIS | 125 | 33.868 | 9.228 | 50.668 | 1.00 | 11.12 |
| ATOM | 970 | N | ASN | 126 | 34.083 | 7.837 | 52.420 | 1.00 | 8.74 |
| ATOM | 971 | CA | ASN | 126 | 35.193 | 8.623 | 52.953 | 1.00 | 8.54 |
| ATOM | 972 | CB | ASN | 126 | 35.428 | 8.115 | 54.411 | 1.00 | 8.14 |
| ATOM | 973 | CG | ASN | 126 | 36.416 | 9.019 | 55.101 | 1.00 | 8.88 |
| ATOM | 974 | OD1 | ASN | 126 | 36.270 | 10.238 | 54.953 | 1.00 | 10.54 |
| ATOM | 975 | ND2 | ASN | 126 | 37.448 | 8.494 | 55.731 | 1.00 | 9.56 |
| ATOM | 976 | C | ASN | 126 | 36.402 | 8.566 | 52.090 | 1.00 | 8.32 |
| ATOM | 977 | O | ASN | 126 | 37.199 | 9.515 | 51.941 | 1.00 | 9.13 |
| ATOM | 978 | N | LYS | 127 | 36.595 | 7.416 | 51.408 | 1.00 | 8.46 |
| ATOM | 979 | CA | LYS | 127 | 37.733 | 7.182 | 50.536 | 1.00 | 6.93 |
| ATOM | 980 | CB | LYS | 127 | 38.785 | 6.232 | 51.138 | 1.00 | 8.23 |
| ATOM | 981 | CG | LYS | 127 | 39.335 | 6.671 | 52.443 | 1.00 | 13.12 |
| ATOM | 982 | CD | LYS | 127 | 40.489 | 5.811 | 52.965 | 1.00 | 16.68 |
| ATOM | 983 | CE | LYS | 127 | 40.871 | 6.388 | 54.335 | 1.00 | 21.82 |
| ATOM | 984 | NZ | LYS | 127 | 41.984 | 5.677 | 54.991 | 1.00 | 26.43 |
| ATOM | 985 | C | LYS | 127 | 37.279 | 6.566 | 49.206 | 1.00 | 5.67 |
| ATOM | 986 | O | LYS | 127 | 36.408 | 5.710 | 49.137 | 1.00 | 5.09 |
| ATOM | 987 | N | ILE | 128 | 37.890 | 7.084 | 48.137 | 1.00 | 6.06 |
| ATOM | 988 | CA | ILE | 128 | 37.584 | 6.599 | 46.802 | 1.00 | 5.35 |
| ATOM | 989 | CB | ILE | 128 | 36.554 | 7.482 | 46.060 | 1.00 | 3.79 |
| ATOM | 990 | CG1 | ILE | 128 | 37.101 | 8.916 | 45.871 | 1.00 | 2.49 |

TABLE 1-continued

Structure Coordinates for S. aureus pdf

| | | | | | | | | |
|---|---|---|---|---|---|---|---|---|
| ATOM | 991 | CD1 | ILE | 128 | 36.165 | 9.779 | 45.033 | 1.00 | 4.28 |
| ATOM | 992 | CG2 | ILE | 128 | 35.180 | 7.503 | 46.769 | 1.00 | 2.00 |
| ATOM | 993 | C | ILE | 128 | 38.855 | 6.553 | 45.951 | 1.00 | 4.84 |
| ATOM | 994 | O | ILE | 128 | 39.849 | 7.235 | 46.194 | 1.00 | 3.72 |
| ATOM | 995 | N | THR | 129 | 38.812 | 5.755 | 44.906 | 1.00 | 4.26 |
| ATOM | 996 | CA | THR | 129 | 39.886 | 5.639 | 43.932 | 1.00 | 5.44 |
| ATOM | 997 | CB | THR | 129 | 40.600 | 4.262 | 43.874 | 1.00 | 5.74 |
| ATOM | 998 | OG1 | THR | 129 | 41.384 | 4.124 | 45.083 | 1.00 | 6.67 |
| ATOM | 999 | CG2 | THR | 129 | 41.546 | 4.171 | 42.697 | 1.00 | 3.87 |
| ATOM | 1000 | C | THR | 129 | 39.130 | 5.882 | 42.610 | 1.00 | 5.76 |
| ATOM | 1001 | O | THR | 129 | 38.104 | 5.237 | 42.387 | 1.00 | 4.96 |
| ATOM | 1002 | N | ILE | 130 | 39.584 | 6.856 | 41.882 | 1.00 | 6.40 |
| ATOM | 1003 | CA | ILE | 130 | 39.076 | 7.252 | 40.599 | 1.00 | 7.37 |
| ATOM | 1004 | CB | ILE | 130 | 38.692 | 8.769 | 40.544 | 1.00 | 7.11 |
| ATOM | 1005 | CG1 | ILE | 130 | 37.391 | 8.969 | 41.370 | 1.00 | 7.19 |
| ATOM | 1006 | CD1 | ILE | 130 | 36.998 | 10.444 | 41.506 | 1.00 | 10.30 |
| ATOM | 1007 | CG2 | ILE | 130 | 38.474 | 9.320 | 39.150 | 1.00 | 7.49 |
| ATOM | 1008 | C | ILE | 130 | 40.132 | 7.022 | 39.492 | 1.00 | 7.21 |
| ATOM | 1009 | O | ILE | 130 | 41.291 | 7.322 | 39.617 | 1.00 | 6.63 |
| ATOM | 1010 | N | LYS | 131 | 39.603 | 6.521 | 38.372 | 1.00 | 7.02 |
| ATOM | 1011 | CA | LYS | 131 | 40.359 | 6.352 | 37.170 | 1.00 | 8.19 |
| ATOM | 1012 | CB | LYS | 131 | 40.513 | 4.982 | 36.602 | 1.00 | 11.33 |
| ATOM | 1013 | CG | LYS | 131 | 41.314 | 3.971 | 37.416 | 1.00 | 13.57 |
| ATOM | 1014 | CD | LYS | 131 | 41.458 | 2.749 | 36.505 | 1.00 | 17.15 |
| ATOM | 1015 | CE | LYS | 131 | 42.455 | 1.746 | 37.039 | 1.00 | 20.87 |
| ATOM | 1016 | NZ | LYS | 131 | 42.779 | 0.788 | 35.929 | 1.00 | 25.22 |
| ATOM | 1017 | C | LYS | 131 | 39.709 | 7.288 | 36.109 | 1.00 | 6.91 |
| ATOM | 1018 | O | LYS | 131 | 38.489 | 7.342 | 36.009 | 1.00 | 5.90 |
| ATOM | 1019 | N | ALA | 132 | 40.583 | 8.053 | 35.447 | 1.00 | 6.42 |
| ATOM | 1020 | CA | ALA | 132 | 40.013 | 8.945 | 34.400 | 1.00 | 5.33 |
| ATOM | 1021 | CB | ALA | 132 | 39.562 | 10.235 | 35.083 | 1.00 | 2.00 |
| ATOM | 1022 | C | ALA | 132 | 41.063 | 9.240 | 33.354 | 1.00 | 5.57 |
| ATOM | 1023 | O | ALA | 132 | 42.191 | 8.728 | 33.449 | 1.00 | 6.67 |
| ATOM | 1024 | N | LYS | 133 | 40.734 | 10.026 | 32.341 | 1.00 | 6.83 |
| ATOM | 1025 | CA | LYS | 133 | 41.758 | 10.489 | 31.375 | 1.00 | 7.84 |
| ATOM | 1026 | CB | LYS | 133 | 41.311 | 10.463 | 29.904 | 1.00 | 9.83 |
| ATOM | 1027 | CG | LYS | 133 | 40.878 | 9.164 | 29.336 | 1.00 | 11.29 |
| ATOM | 1028 | CD | LYS | 133 | 41.983 | 8.133 | 29.442 | 1.00 | 14.36 |
| ATOM | 1029 | CE | LYS | 133 | 41.577 | 6.842 | 28.727 | 1.00 | 16.88 |
| ATOM | 1030 | NZ | LYS | 133 | 42.601 | 5.811 | 29.133 | 1.00 | 17.94 |
| ATOM | 1031 | C | LYS | 133 | 41.887 | 12.006 | 31.643 | 1.00 | 6.97 |
| ATOM | 1032 | O | LYS | 133 | 40.940 | 12.600 | 32.143 | 1.00 | 7.81 |
| ATOM | 1033 | N | ASP | 134 | 42.949 | 12.623 | 31.268 | 1.00 | 8.29 |
| ATOM | 1034 | CA | ASP | 134 | 43.141 | 14.055 | 31.363 | 1.00 | 7.39 |
| ATOM | 1035 | CB | ASP | 134 | 44.519 | 14.454 | 31.823 | 1.00 | 8.51 |
| ATOM | 1036 | CG | ASP | 134 | 45.717 | 14.189 | 30.975 | 1.00 | 8.37 |
| ATOM | 1037 | OD1 | ASP | 134 | 46.894 | 14.220 | 31.413 | 1.00 | 8.77 |
| ATOM | 1038 | OD2 | ASP | 134 | 45.585 | 13.946 | 29.746 | 1.00 | 9.62 |
| ATOM | 1039 | C | ASP | 134 | 42.752 | 14.675 | 30.015 | 1.00 | 9.13 |
| ATOM | 1040 | O | ASP | 134 | 42.283 | 13.980 | 29.053 | 1.00 | 10.00 |
| ATOM | 1041 | N | ILE | 135 | 42.905 | 15.962 | 29.856 | 1.00 | 8.82 |
| ATOM | 1042 | CA | ILE | 135 | 42.538 | 16.710 | 28.635 | 1.00 | 9.79 |
| ATOM | 1043 | CB | ILE | 135 | 42.652 | 18.224 | 28.949 | 1.00 | 10.08 |
| ATOM | 1044 | CG1 | ILE | 135 | 41.900 | 19.058 | 27.938 | 1.00 | 9.25 |
| ATOM | 1045 | CD1 | ILE | 135 | 41.972 | 20.551 | 28.227 | 1.00 | 9.86 |
| ATOM | 1046 | CG2 | ILE | 135 | 44.134 | 18.642 | 28.921 | 1.00 | 10.69 |
| ATOM | 1047 | C | ILE | 135 | 43.229 | 16.263 | 27.395 | 1.00 | 9.88 |
| ATOM | 1048 | O | ILE | 135 | 42.729 | 16.310 | 26.254 | 1.00 | 10.08 |
| ATOM | 1049 | N | GLU | 136 | 44.447 | 15.717 | 27.490 | 1.00 | 9.82 |
| ATOM | 1050 | CA | GLU | 136 | 45.211 | 15.168 | 26.423 | 1.00 | 9.97 |
| ATOM | 1051 | CB | GLU | 136 | 46.721 | 15.501 | 26.503 | 1.00 | 9.18 |
| ATOM | 1052 | CG | GLU | 136 | 47.025 | 16.963 | 26.269 | 1.00 | 11.11 |
| ATOM | 1053 | CD | GLU | 136 | 46.573 | 17.426 | 24.871 | 1.00 | 11.43 |
| ATOM | 1054 | OE1 | GLU | 136 | 46.759 | 16.636 | 23.938 | 1.00 | 12.83 |
| ATOM | 1055 | OE2 | GLU | 136 | 46.039 | 18.527 | 24.823 | 1.00 | 12.16 |
| ATOM | 1056 | C | GLU | 136 | 45.033 | 13.647 | 26.240 | 1.00 | 9.67 |
| ATOM | 1057 | O | GLU | 136 | 45.793 | 13.083 | 25.431 | 1.00 | 10.16 |
| ATOM | 1058 | N | GLY | 137 | 44.149 | 12.996 | 26.990 | 1.00 | 8.60 |
| ATOM | 1059 | CA | GLY | 137 | 43.916 | 11.554 | 26.862 | 1.00 | 7.80 |
| ATOM | 1060 | C | GLY | 137 | 44.812 | 10.661 | 27.640 | 1.00 | 6.10 |
| ATOM | 1061 | O | GLY | 137 | 44.951 | 9.443 | 27.445 | 1.00 | 6.27 |
| ATOM | 1062 | N | ASN | 138 | 45.611 | 11.224 | 28.533 | 1.00 | 6.53 |
| ATOM | 1063 | CA | ASN | 138 | 46.540 | 10.485 | 29.348 | 1.00 | 7.17 |
| ATOM | 1064 | CB | ASN | 138 | 47.859 | 11.112 | 29.564 | 1.00 | 6.62 |
| ATOM | 1065 | CG | ASN | 138 | 48.666 | 11.343 | 28.324 | 1.00 | 6.41 |
| ATOM | 1066 | OD1 | ASN | 138 | 48.891 | 10.474 | 27.473 | 1.00 | 7.83 |
| ATOM | 1067 | ND2 | ASN | 138 | 49.080 | 12.589 | 28.118 | 1.00 | 5.84 |

TABLE 1-continued

Structure Coordinates for *S. aureus* pdf

| ATOM | 1068 | C | ASN | 138 | 45.782 | 9.938 | 30.557 | 1.00 | 8.75 |
|------|------|------|-----|-----|--------|--------|--------|------|------|
| ATOM | 1069 | O | ASN | 138 | 44.731 | 10.431 | 30.900 | 1.00 | 9.34 |
| ATOM | 1070 | N | ASP | 139 | 46.289 | 8.893 | 31.200 | 1.00 | 9.51 |
| ATOM | 1071 | CA | ASP | 139 | 45.642 | 8.232 | 32.304 | 1.00 | 9.46 |
| ATOM | 1072 | CB | ASP | 139 | 46.137 | 6.738 | 32.368 | 1.00 | 9.74 |
| ATOM | 1073 | CG | ASP | 139 | 45.953 | 6.042 | 31.034 | 1.00 | 10.25 |
| ATOM | 1074 | OD1 | ASP | 139 | 45.029 | 6.416 | 30.295 | 1.00 | 10.01 |
| ATOM | 1075 | OD2 | ASP | 139 | 46.802 | 5.192 | 30.714 | 1.00 | 10.42 |
| ATOM | 1076 | C | ASP | 139 | 45.931 | 8.866 | 33.648 | 1.00 | 8.48 |
| ATOM | 1077 | O | ASP | 139 | 47.094 | 9.212 | 33.934 | 1.00 | 8.89 |
| ATOM | 1078 | N | ILE | 140 | 44.896 | 9.015 | 34.458 | 1.00 | 8.07 |
| ATOM | 1079 | CA | ILE | 140 | 45.072 | 9.590 | 35.799 | 1.00 | 9.43 |
| ATOM | 1080 | CB | ILE | 140 | 44.435 | 10.979 | 35.964 | 1.00 | 12.18 |
| ATOM | 1081 | CG1 | ILE | 140 | 44.723 | 11.979 | 34.883 | 1.00 | 15.73 |
| ATOM | 1082 | CD1 | ILE | 140 | 46.188 | 12.373 | 34.669 | 1.00 | 17.79 |
| ATOM | 1083 | CG2 | ILE | 140 | 44.881 | 11.612 | 37.311 | 1.00 | 13.76 |
| ATOM | 1084 | C | ILE | 140 | 44.358 | 8.632 | 36.775 | 1.00 | 8.12 |
| ATOM | 1085 | O | ILE | 140 | 43.265 | 8.238 | 36.565 | 1.00 | 7.55 |
| ATOM | 1086 | N | GLN | 141 | 44.992 | 8.330 | 37.908 | 1.00 | 8.68 |
| ATOM | 1087 | CA | GLN | 141 | 44.370 | 7.492 | 38.929 | 1.00 | 8.09 |
| ATOM | 1088 | CB | GLN | 141 | 44.930 | 6.081 | 39.016 | 1.00 | 10.14 |
| ATOM | 1089 | CG | GLN | 141 | 44.139 | 5.210 | 39.984 | 1.00 | 13.25 |
| ATOM | 1090 | CD | GLN | 141 | 44.556 | 3.767 | 40.096 | 1.00 | 14.70 |
| ATOM | 1091 | OE1 | GLN | 141 | 45.723 | 3.425 | 40.103 | 1.00 | 16.12 |
| ATOM | 1092 | NE2 | GLN | 141 | 43.607 | 2.851 | 40.176 | 1.00 | 14.82 |
| ATOM | 1093 | C | GLN | 141 | 44.575 | 8.281 | 40.247 | 1.00 | 6.14 |
| ATOM | 1094 | O | GLN | 141 | 45.713 | 8.595 | 40.573 | 1.00 | 7.17 |
| ATOM | 1095 | N | LEU | 142 | 43.498 | 8.589 | 40.928 | 1.00 | 4.24 |
| ATOM | 1096 | CA | LEU | 142 | 43.540 | 9.376 | 42.127 | 1.00 | 4.16 |
| ATOM | 1097 | CB | LEU | 142 | 42.641 | 10.638 | 42.092 | 1.00 | 3.14 |
| ATOM | 1098 | CG | LEU | 142 | 42.865 | 11.671 | 40.964 | 1.00 | 4.72 |
| ATOM | 1099 | CD1 | LEU | 142 | 42.418 | 11.139 | 39.628 | 1.00 | 7.12 |
| ATOM | 1100 | CD2 | LEU | 142 | 42.191 | 12.984 | 41.303 | 1.00 | 5.38 |
| ATOM | 1101 | C | LEU | 142 | 43.024 | 8.590 | 43.362 | 1.00 | 4.55 |
| ATOM | 1102 | O | LEU | 142 | 42.026 | 7.918 | 43.302 | 1.00 | 3.43 |
| ATOM | 1103 | N | ARG | 143 | 43.706 | 8.838 | 44.442 | 1.00 | 5.60 |
| ATOM | 1104 | CA | ARG | 143 | 43.254 | 8.230 | 45.735 | 1.00 | 6.45 |
| ATOM | 1105 | CB | ARG | 143 | 44.406 | 7.410 | 46.295 | 1.00 | 6.30 |
| ATOM | 1106 | CG | ARG | 143 | 44.572 | 6.089 | 45.510 | 1.00 | 6.38 |
| ATOM | 1107 | CD | ARG | 143 | 45.870 | 5.421 | 45.955 | 1.00 | 7.24 |
| ATOM | 1108 | NE | ARG | 143 | 46.994 | 6.164 | 45.399 | 1.00 | 8.41 |
| ATOM | 1109 | CZ | ARG | 143 | 47.487 | 6.175 | 44.186 | 1.00 | 7.10 |
| ATOM | 1110 | NH1 | ARG | 143 | 47.010 | 5.371 | 43.229 | 1.00 | 10.56 |
| ATOM | 1111 | NH2 | ARG | 143 | 48.441 | 6.994 | 43.872 | 1.00 | 6.66 |
| ATOM | 1112 | C | ARG | 143 | 42.862 | 9.416 | 46.587 | 1.00 | 6.59 |
| ATOM | 1113 | O | ARG | 143 | 43.759 | 10.213 | 46.872 | 1.00 | 8.32 |
| ATOM | 1114 | N | LEU | 144 | 41.608 | 9.616 | 46.887 | 1.00 | 6.29 |
| ATOM | 1115 | CA | LEU | 144 | 41.146 | 10.800 | 47.621 | 1.00 | 7.40 |
| ATOM | 1116 | CB | LEU | 144 | 40.077 | 11.501 | 46.737 | 1.00 | 8.55 |
| ATOM | 1117 | CG | LEU | 144 | 40.603 | 12.027 | 45.375 | 1.00 | 8.47 |
| ATOM | 1118 | CD1 | LEU | 144 | 39.402 | 12.282 | 44.481 | 1.00 | 6.95 |
| ATOM | 1119 | CD2 | LEU | 144 | 41.379 | 13.312 | 45.591 | 1.00 | 5.70 |
| ATOM | 1120 | C | LEU | 144 | 40.470 | 10.405 | 48.909 | 1.00 | 9.13 |
| ATOM | 1121 | O | LEU | 144 | 39.953 | 9.293 | 49.040 | 1.00 | 8.94 |
| ATOM | 1122 | N | LYS | 145 | 40.423 | 11.365 | 49.832 | 1.00 | 10.82 |
| ATOM | 1123 | CA | LYS | 145 | 39.801 | 11.116 | 51.142 | 1.00 | 11.39 |
| ATOM | 1124 | CB | LYS | 145 | 40.924 | 10.619 | 52.041 | 1.00 | 13.95 |
| ATOM | 1125 | CG | LYS | 145 | 40.646 | 10.374 | 53.458 | 1.00 | 18.80 |
| ATOM | 1126 | CD | LYS | 145 | 41.861 | 9.909 | 54.232 | 1.00 | 25.06 |
| ATOM | 1127 | CE | LYS | 145 | 42.963 | 10.908 | 54.354 | 1.00 | 31.66 |
| ATOM | 1128 | NZ | LYS | 145 | 43.539 | 11.396 | 53.059 | 1.00 | 37.64 |
| ATOM | 1129 | C | LYS | 145 | 39.188 | 12.388 | 51.720 | 1.00 | 9.96 |
| ATOM | 1130 | O | LYS | 145 | 39.596 | 13.478 | 51.389 | 1.00 | 9.17 |
| ATOM | 1131 | N | GLY | 146 | 38.108 | 12.225 | 52.519 | 1.00 | 8.79 |
| ATOM | 1132 | CA | GLY | 146 | 37.456 | 13.328 | 53.137 | 1.00 | 8.43 |
| ATOM | 1133 | C | GLY | 146 | 36.897 | 14.360 | 52.201 | 1.00 | 8.40 |
| ATOM | 1134 | O | GLY | 146 | 36.151 | 14.060 | 51.254 | 1.00 | 8.45 |
| ATOM | 1135 | N | TYR | 147 | 37.263 | 15.616 | 52.405 | 1.00 | 8.09 |
| ATOM | 1136 | CA | TYR | 147 | 36.779 | 16.715 | 51.642 | 1.00 | 7.87 |
| ATOM | 1137 | CB | TYR | 147 | 37.196 | 18.074 | 52.234 | 1.00 | 9.36 |
| ATOM | 1138 | CG | TYR | 147 | 36.595 | 19.261 | 51.474 | 1.00 | 11.07 |
| ATOM | 1139 | CD1 | TYR | 147 | 35.277 | 19.634 | 51.672 | 1.00 | 11.07 |
| ATOM | 1140 | CE1 | TYR | 147 | 34.748 | 20.679 | 50.935 | 1.00 | 13.45 |
| ATOM | 1141 | CZ | TYR | 147 | 35.529 | 21.400 | 50.057 | 1.00 | 13.62 |
| ATOM | 1142 | OH | TYR | 147 | 35.036 | 22.483 | 49.389 | 1.00 | 13.97 |
| ATOM | 1143 | CE2 | TYR | 147 | 36.866 | 21.045 | 49.873 | 1.00 | 13.40 |
| ATOM | 1144 | CD2 | TYR | 147 | 37.362 | 19.974 | 50.592 | 1.00 | 12.10 |

TABLE 1-continued

Structure Coordinates for *S. aureus* pdf

| | | | | | | | | |
|---|---|---|---|---|---|---|---|---|
| ATOM | 1145 | C | TYR | 147 | 36.885 | 16.626 | 50.152 | 1.00 | 5.90 |
| ATOM | 1146 | O | TYR | 147 | 35.845 | 16.786 | 49.504 | 1.00 | 4.84 |
| ATOM | 1147 | N | PRO | 148 | 38.043 | 16.403 | 49.590 | 1.00 | 7.00 |
| ATOM | 1148 | CA | PRO | 148 | 38.156 | 16.303 | 48.132 | 1.00 | 7.78 |
| ATOM | 1149 | CB | PRO | 148 | 39.605 | 16.180 | 47.837 | 1.00 | 7.31 |
| ATOM | 1150 | CG | PRO | 148 | 40.271 | 15.930 | 49.125 | 1.00 | 8.35 |
| ATOM | 1151 | CD | PRO | 148 | 39.340 | 16.286 | 50.255 | 1.00 | 7.21 |
| ATOM | 1152 | C | PRO | 148 | 37.394 | 15.074 | 47.639 | 1.00 | 7.01 |
| ATOM | 1153 | O | PRO | 148 | 36.995 | 15.119 | 46.479 | 1.00 | 8.08 |
| ATOM | 1154 | N | ALA | 149 | 37.271 | 14.025 | 48.435 | 1.00 | 5.19 |
| ATOM | 1155 | CA | ALA | 149 | 36.571 | 12.828 | 48.000 | 1.00 | 4.31 |
| ATOM | 1156 | CB | ALA | 149 | 36.715 | 11.666 | 48.983 | 1.00 | 2.00 |
| ATOM | 1157 | C | ALA | 149 | 35.079 | 13.175 | 47.824 | 1.00 | 3.82 |
| ATOM | 1158 | O | ALA | 149 | 34.463 | 12.772 | 46.850 | 1.00 | 3.79 |
| ATOM | 1159 | N | ILE | 150 | 34.535 | 13.957 | 48.742 | 1.00 | 4.49 |
| ATOM | 1160 | CA | ILE | 150 | 33.146 | 14.400 | 48.705 | 1.00 | 5.37 |
| ATOM | 1161 | CB | ILE | 150 | 32.790 | 15.107 | 50.026 | 1.00 | 7.40 |
| ATOM | 1162 | CG2 | ILE | 150 | 31.624 | 16.049 | 49.837 | 1.00 | 7.23 |
| ATOM | 1163 | CG1 | ILE | 150 | 32.660 | 14.085 | 51.137 | 1.00 | 8.06 |
| ATOM | 1164 | CD1 | ILE | 150 | 32.623 | 14.512 | 52.578 | 1.00 | 7.31 |
| ATOM | 1165 | C | ILE | 150 | 32.925 | 15.337 | 47.504 | 1.00 | 4.53 |
| ATOM | 1166 | O | ILE | 150 | 31.943 | 15.147 | 46.813 | 1.00 | 3.53 |
| ATOM | 1167 | N | VAL | 151 | 33.896 | 16.213 | 47.249 | 1.00 | 4.55 |
| ATOM | 1168 | CA | VAL | 151 | 33.781 | 17.130 | 46.083 | 1.00 | 4.71 |
| ATOM | 1169 | CB | VAL | 151 | 34.800 | 18.238 | 46.088 | 1.00 | 4.83 |
| ATOM | 1170 | CG1 | VAL | 151 | 34.777 | 19.142 | 44.820 | 1.00 | 4.32 |
| ATOM | 1171 | CG2 | VAL | 151 | 34.475 | 19.164 | 47.311 | 1.00 | 5.52 |
| ATOM | 1172 | C | VAL | 151 | 33.820 | 16.304 | 44.795 | 1.00 | 5.66 |
| ATOM | 1173 | O | VAL | 151 | 32.961 | 16.581 | 43.957 | 1.00 | 6.35 |
| ATOM | 1174 | N | PHE | 152 | 34.749 | 15.379 | 44.629 | 1.00 | 4.24 |
| ATOM | 1175 | CA | PHE | 152 | 34.658 | 14.562 | 43.361 | 1.00 | 4.96 |
| ATOM | 1176 | CB | PHE | 152 | 35.902 | 13.806 | 43.085 | 1.00 | 4.05 |
| ATOM | 1177 | CG | PHE | 152 | 37.140 | 14.561 | 42.669 | 1.00 | 6.55 |
| ATOM | 1178 | CD1 | PHE | 152 | 37.911 | 15.246 | 43.583 | 1.00 | 7.52 |
| ATOM | 1179 | CE1 | PHE | 152 | 39.104 | 15.892 | 43.234 | 1.00 | 6.30 |
| ATOM | 1180 | CZ | PHE | 152 | 39.474 | 15.858 | 41.904 | 1.00 | 4.29 |
| ATOM | 1181 | CE2 | PHE | 152 | 38.732 | 15.203 | 40.973 | 1.00 | 3.38 |
| ATOM | 1182 | CD2 | PHE | 152 | 37.586 | 14.528 | 41.355 | 1.00 | 4.89 |
| ATOM | 1183 | C | PHE | 152 | 33.386 | 13.735 | 43.308 | 1.00 | 4.69 |
| ATOM | 1184 | O | PHE | 152 | 32.812 | 13.579 | 42.203 | 1.00 | 5.23 |
| ATOM | 1185 | N | GLN | 153 | 32.847 | 13.159 | 44.374 | 1.00 | 4.19 |
| ATOM | 1186 | CA | GLN | 153 | 31.588 | 12.395 | 44.269 | 1.00 | 5.10 |
| ATOM | 1187 | CB | GLN | 153 | 31.284 | 11.638 | 45.555 | 1.00 | 4.46 |
| ATOM | 1188 | CG | GLN | 153 | 32.324 | 10.564 | 45.854 | 1.00 | 5.68 |
| ATOM | 1189 | CD | GLN | 153 | 32.214 | 9.837 | 47.177 | 1.00 | 7.54 |
| ATOM | 1190 | OE1 | GLN | 153 | 31.475 | 8.874 | 47.401 | 1.00 | 9.94 |
| ATOM | 1191 | NE2 | GLN | 153 | 33.031 | 10.289 | 48.117 | 1.00 | 5.48 |
| ATOM | 1192 | C | GLN | 153 | 30.446 | 13.259 | 43.812 | 1.00 | 5.17 |
| ATOM | 1193 | O | GLN | 153 | 29.581 | 12.883 | 42.981 | 1.00 | 6.71 |
| ATOM | 1194 | N | HIS | 154 | 30.385 | 14.471 | 44.338 | 1.00 | 4.09 |
| ATOM | 1195 | CA | HIS | 154 | 29.340 | 15.431 | 43.990 | 1.00 | 4.25 |
| ATOM | 1196 | CB | HIS | 154 | 29.636 | 16.731 | 44.863 | 1.00 | 3.87 |
| ATOM | 1197 | CG | HIS | 154 | 28.693 | 17.851 | 44.588 | 1.00 | 3.28 |
| ATOM | 1198 | ND1 | HIS | 154 | 27.711 | 18.274 | 45.436 | 1.00 | 5.34 |
| ATOM | 1199 | CE1 | HIS | 154 | 27.004 | 19.245 | 44.925 | 1.00 | 4.80 |
| ATOM | 1200 | NE2 | HIS | 154 | 27.491 | 19.463 | 43.683 | 1.00 | 6.11 |
| ATOM | 1201 | CD2 | HIS | 154 | 28.529 | 18.603 | 43.465 | 1.00 | 5.20 |
| ATOM | 1202 | C | HIS | 154 | 29.391 | 15.728 | 42.477 | 1.00 | 3.83 |
| ATOM | 1203 | O | HIS | 154 | 28.401 | 15.710 | 41.793 | 1.00 | 3.56 |
| ATOM | 1204 | N | GLU | 155 | 30.571 | 16.019 | 41.951 | 1.00 | 4.91 |
| ATOM | 1205 | CA | GLU | 155 | 30.779 | 16.302 | 40.553 | 1.00 | 7.09 |
| ATOM | 1206 | CB | GLU | 155 | 32.150 | 16.925 | 40.264 | 1.00 | 7.65 |
| ATOM | 1207 | CG | GLU | 155 | 32.331 | 18.281 | 41.029 | 1.00 | 6.88 |
| ATOM | 1208 | CD | GLU | 155 | 31.161 | 19.223 | 40.725 | 1.00 | 8.48 |
| ATOM | 1209 | OE1 | GLU | 155 | 30.644 | 19.235 | 39.570 | 1.00 | 6.97 |
| ATOM | 1210 | OE2 | GLU | 155 | 30.704 | 19.907 | 41.673 | 1.00 | 9.81 |
| ATOM | 1211 | C | GLU | 155 | 30.481 | 15.079 | 39.675 | 1.00 | 6.80 |
| ATOM | 1212 | O | GLU | 155 | 29.815 | 15.254 | 38.625 | 1.00 | 7.83 |
| ATOM | 1213 | N | ILE | 156 | 30.914 | 13.904 | 40.026 | 1.00 | 6.49 |
| ATOM | 1214 | CA | ILE | 156 | 30.573 | 12.698 | 39.226 | 1.00 | 6.27 |
| ATOM | 1215 | CB | ILE | 156 | 31.359 | 11.470 | 39.668 | 1.00 | 5.97 |
| ATOM | 1216 | CG1 | ILE | 156 | 32.848 | 11.653 | 39.436 | 1.00 | 4.24 |
| ATOM | 1217 | CD1 | ILE | 156 | 33.760 | 10.571 | 39.861 | 1.00 | 3.82 |
| ATOM | 1218 | CG2 | ILE | 156 | 30.804 | 10.186 | 39.036 | 1.00 | 7.37 |
| ATOM | 1219 | C | ILE | 156 | 29.066 | 12.513 | 39.298 | 1.00 | 5.98 |
| ATOM | 1220 | O | ILE | 156 | 28.467 | 12.196 | 38.252 | 1.00 | 5.77 |
| ATOM | 1221 | N | ASP | 157 | 28.408 | 12.644 | 40.429 | 1.00 | 5.23 |

TABLE 1-continued

Structure Coordinates for S. aureus pdf

| | | | | | | | | |
|---|---|---|---|---|---|---|---|---|
| ATOM | 1222 | CA | ASP | 157 | 26.978 | 12.553 | 40.507 | 1.00 | 5.85 |
| ATOM | 1223 | CB | ASP | 157 | 26.371 | 12.978 | 41.821 | 1.00 | 7.42 |
| ATOM | 1224 | CG | ASP | 157 | 26.314 | 11.911 | 42.878 | 1.00 | 10.11 |
| ATOM | 1225 | OD1 | ASP | 157 | 26.594 | 10.731 | 42.577 | 1.00 | 9.03 |
| ATOM | 1226 | OD2 | ASP | 157 | 25.822 | 12.253 | 43.982 | 1.00 | 10.69 |
| ATOM | 1227 | C | ASP | 157 | 26.248 | 13.307 | 39.386 | 1.00 | 7.07 |
| ATOM | 1228 | O | ASP | 157 | 25.287 | 12.755 | 38.834 | 1.00 | 8.10 |
| ATOM | 1229 | N | HIS | 158 | 26.661 | 14.502 | 39.062 | 1.00 | 6.19 |
| ATOM | 1230 | CA | HIS | 158 | 26.112 | 15.287 | 38.029 | 1.00 | 7.49 |
| ATOM | 1231 | CB | HIS | 158 | 26.810 | 16.641 | 37.753 | 1.00 | 5.85 |
| ATOM | 1232 | CG | HIS | 158 | 26.559 | 17.707 | 38.769 | 1.00 | 5.01 |
| ATOM | 1233 | ND1 | HIS | 158 | 25.266 | 18.168 | 38.959 | 1.00 | 5.03 |
| ATOM | 1234 | CE1 | HIS | 158 | 25.282 | 19.121 | 39.895 | 1.00 | 4.19 |
| ATOM | 1235 | NE2 | HIS | 158 | 26.557 | 19.288 | 40.292 | 1.00 | 4.26 |
| ATOM | 1236 | CD2 | HIS | 158 | 27.363 | 18.439 | 39.584 | 1.00 | 2.60 |
| ATOM | 1237 | C | HIS | 158 | 26.090 | 14.599 | 36.656 | 1.00 | 8.47 |
| ATOM | 1238 | O | HIS | 158 | 25.171 | 14.898 | 35.913 | 1.00 | 9.43 |
| ATOM | 1239 | N | LEU | 159 | 27.078 | 13.780 | 36.392 | 1.00 | 8.63 |
| ATOM | 1240 | CA | LEU | 159 | 27.220 | 13.074 | 35.122 | 1.00 | 9.33 |
| ATOM | 1241 | CB | LEU | 159 | 28.636 | 12.532 | 34.967 | 1.00 | 7.47 |
| ATOM | 1242 | CG | LEU | 159 | 29.853 | 13.426 | 35.128 | 1.00 | 7.64 |
| ATOM | 1243 | CD1 | LEU | 159 | 31.101 | 12.606 | 34.923 | 1.00 | 6.21 |
| ATOM | 1244 | CD2 | LEU | 159 | 29.832 | 14.677 | 34.295 | 1.00 | 6.97 |
| ATOM | 1245 | C | LEU | 159 | 26.192 | 11.937 | 35.024 | 1.00 | 8.64 |
| ATOM | 1246 | O | LEU | 159 | 25.885 | 11.426 | 33.947 | 1.00 | 7.94 |
| ATOM | 1247 | N | ASN | 160 | 25.605 | 11.583 | 36.164 | 1.00 | 9.77 |
| ATOM | 1248 | CA | ASN | 160 | 24.580 | 10.573 | 36.277 | 1.00 | 9.90 |
| ATOM | 1249 | CB | ASN | 160 | 24.944 | 9.490 | 37.318 | 1.00 | 10.05 |
| ATOM | 1250 | CG | ASN | 160 | 26.211 | 8.761 | 36.969 | 1.00 | 8.81 |
| ATOM | 1251 | OD1 | ASN | 160 | 26.495 | 8.464 | 35.805 | 1.00 | 8.76 |
| ATOM | 1252 | ND2 | ASN | 160 | 27.049 | 8.507 | 37.960 | 1.00 | 11.57 |
| ATOM | 1253 | C | ASN | 160 | 23.207 | 11.100 | 36.542 | 1.00 | 10.13 |
| ATOM | 1254 | O | ASN | 160 | 22.238 | 10.334 | 36.824 | 1.00 | 9.97 |
| ATOM | 1255 | N | GLY | 161 | 22.996 | 12.404 | 36.413 | 1.00 | 10.67 |
| ATOM | 1256 | CA | GLY | 161 | 21.695 | 13.015 | 36.647 | 1.00 | 9.90 |
| ATOM | 1257 | C | GLY | 161 | 21.275 | 13.057 | 38.096 | 1.00 | 10.81 |
| ATOM | 1258 | O | GLY | 161 | 20.049 | 13.064 | 38.394 | 1.00 | 11.80 |
| ATOM | 1259 | N | VAL | 162 | 22.196 | 13.066 | 39.037 | 1.00 | 10.62 |
| ATOM | 1260 | CA | VAL | 162 | 21.975 | 13.082 | 40.469 | 1.00 | 10.24 |
| ATOM | 1261 | CB | VAL | 162 | 22.883 | 11.980 | 41.119 | 1.00 | 12.28 |
| ATOM | 1262 | CG1 | VAL | 162 | 22.819 | 12.009 | 42.654 | 1.00 | 11.36 |
| ATOM | 1263 | CG2 | VAL | 162 | 22.436 | 10.623 | 40.619 | 1.00 | 10.82 |
| ATOM | 1264 | C | VAL | 162 | 22.378 | 14.419 | 41.070 | 1.00 | 9.72 |
| ATOM | 1265 | O | VAL | 162 | 23.480 | 14.919 | 40.817 | 1.00 | 9.92 |
| ATOM | 1266 | N | MET | 163 | 21.507 | 14.997 | 41.900 | 1.00 | 8.97 |
| ATOM | 1267 | CA | MET | 163 | 21.754 | 16.260 | 42.575 | 1.00 | 9.40 |
| ATOM | 1268 | CB | MET | 163 | 20.557 | 17.207 | 42.379 | 1.00 | 9.97 |
| ATOM | 1269 | CG | MET | 163 | 20.282 | 17.521 | 40.923 | 1.00 | 11.50 |
| ATOM | 1270 | SD | MET | 163 | 21.495 | 18.562 | 40.125 | 1.00 | 12.73 |
| ATOM | 1271 | CE | MET | 163 | 21.165 | 20.109 | 40.910 | 1.00 | 11.88 |
| ATOM | 1272 | C | MET | 163 | 22.009 | 15.970 | 44.058 | 1.00 | 10.17 |
| ATOM | 1273 | O | MET | 163 | 21.477 | 14.989 | 44.595 | 1.00 | 10.49 |
| ATOM | 1274 | N | PHE | 164 | 22.853 | 16.760 | 44.715 | 1.00 | 9.65 |
| ATOM | 1275 | CA | PHE | 164 | 23.213 | 16.489 | 46.086 | 1.00 | 8.95 |
| ATOM | 1276 | CB | PHE | 164 | 24.153 | 17.529 | 46.683 | 1.00 | 8.12 |
| ATOM | 1277 | CG | PHE | 164 | 23.519 | 18.850 | 47.009 | 1.00 | 7.63 |
| ATOM | 1278 | CD1 | PHE | 164 | 22.981 | 19.041 | 48.271 | 1.00 | 7.03 |
| ATOM | 1279 | CD2 | PHE | 164 | 23.442 | 19.870 | 46.055 | 1.00 | 6.36 |
| ATOM | 1280 | CE1 | PHE | 164 | 22.357 | 20.248 | 48.597 | 1.00 | 9.27 |
| ATOM | 1281 | CE2 | PHE | 164 | 22.792 | 21.030 | 46.358 | 1.00 | 7.45 |
| ATOM | 1282 | CZ | PHE | 164 | 22.288 | 21.248 | 47.613 | 1.00 | 7.70 |
| ATOM | 1283 | C | PHE | 164 | 22.073 | 16.212 | 47.048 | 1.00 | 8.66 |
| ATOM | 1284 | O | PHE | 164 | 22.221 | 15.427 | 47.999 | 1.00 | 8.17 |
| ATOM | 1285 | N | TYR | 165 | 20.984 | 16.929 | 46.869 | 1.00 | 9.74 |
| ATOM | 1286 | CA | TYR | 165 | 19.833 | 16.874 | 47.754 | 1.00 | 9.53 |
| ATOM | 1287 | CB | TYR | 165 | 18.975 | 18.140 | 47.553 | 1.00 | 10.74 |
| ATOM | 1288 | CG | TYR | 165 | 18.393 | 18.301 | 46.175 | 1.00 | 9.43 |
| ATOM | 1289 | CD1 | TYR | 165 | 17.319 | 17.501 | 45.785 | 1.00 | 9.93 |
| ATOM | 1290 | CE1 | TYR | 165 | 16.744 | 17.616 | 44.529 | 1.00 | 9.33 |
| ATOM | 1291 | CZ | TYR | 165 | 17.210 | 18.604 | 43.679 | 1.00 | 8.93 |
| ATOM | 1292 | OH | TYR | 165 | 16.640 | 18.714 | 42.431 | 1.00 | 11.39 |
| ATOM | 1293 | CE2 | TYR | 165 | 18.278 | 19.393 | 44.033 | 1.00 | 7.81 |
| ATOM | 1294 | CD2 | TYR | 165 | 18.833 | 19.277 | 45.291 | 1.00 | 8.68 |
| ATOM | 1295 | C | TYR | 165 | 19.036 | 15.621 | 47.637 | 1.00 | 11.52 |
| ATOM | 1296 | O | TYR | 165 | 18.088 | 15.381 | 48.431 | 1.00 | 12.08 |
| ATOM | 1297 | N | ASP | 166 | 19.358 | 14.814 | 46.616 | 1.00 | 10.44 |
| ATOM | 1298 | CA | ASP | 166 | 18.686 | 13.533 | 46.441 | 1.00 | 10.72 |

TABLE 1-continued

Structure Coordinates for *S. aureus* pdf

| ATOM | 1299 | CB  | ASP | 166 | 19.095 | 12.916 | 45.117 | 1.00 | 11.36 |
|------|------|-----|-----|-----|--------|--------|--------|------|-------|
| ATOM | 1300 | CG  | ASP | 166 | 18.738 | 13.691 | 43.871 | 1.00 | 12.08 |
| ATOM | 1301 | OD1 | ASP | 166 | 17.862 | 14.574 | 43.837 | 1.00 | 13.05 |
| ATOM | 1302 | OD2 | ASP | 166 | 19.284 | 13.344 | 42.800 | 1.00 | 12.90 |
| ATOM | 1303 | C   | ASP | 166 | 19.152 | 12.599 | 47.567 | 1.00 | 10.61 |
| ATOM | 1304 | O   | ASP | 166 | 18.499 | 11.577 | 47.834 | 1.00 | 9.33  |
| ATOM | 1305 | N   | HIS | 167 | 20.291 | 12.921 | 48.205 | 1.00 | 10.36 |
| ATOM | 1306 | CA  | HIS | 167 | 20.793 | 12.039 | 49.255 | 1.00 | 11.38 |
| ATOM | 1307 | CB  | HIS | 167 | 22.358 | 12.033 | 49.264 | 1.00 | 10.95 |
| ATOM | 1308 | CG  | HIS | 167 | 22.964 | 11.631 | 47.957 | 1.00 | 13.93 |
| ATOM | 1309 | ND1 | HIS | 167 | 22.923 | 10.334 | 47.453 | 1.00 | 13.92 |
| ATOM | 1310 | CE1 | HIS | 167 | 23.546 | 10.300 | 46.291 | 1.00 | 13.33 |
| ATOM | 1311 | NE2 | HIS | 167 | 24.004 | 11.501 | 46.018 | 1.00 | 12.92 |
| ATOM | 1312 | CD2 | HIS | 167 | 23.645 | 12.366 | 47.027 | 1.00 | 13.06 |
| ATOM | 1313 | C   | HIS | 167 | 20.362 | 12.372 | 50.662 | 1.00 | 12.37 |
| ATOM | 1314 | O   | HIS | 167 | 20.858 | 11.734 | 51.630 | 1.00 | 13.63 |
| ATOM | 1315 | N   | ILE | 168 | 19.525 | 13.362 | 50.860 | 1.00 | 12.97 |
| ATOM | 1316 | CA  | ILE | 168 | 19.109 | 13.854 | 52.159 | 1.00 | 12.73 |
| ATOM | 1317 | CB  | ILE | 168 | 18.951 | 15.425 | 52.054 | 1.00 | 13.57 |
| ATOM | 1318 | CG1 | ILE | 168 | 20.228 | 16.110 | 51.593 | 1.00 | 11.58 |
| ATOM | 1319 | CD1 | ILE | 168 | 20.226 | 17.595 | 51.292 | 1.00 | 10.84 |
| ATOM | 1320 | CG2 | ILE | 168 | 18.502 | 15.964 | 53.420 | 1.00 | 12.92 |
| ATOM | 1321 | C   | ILE | 168 | 17.838 | 13.216 | 52.672 | 1.00 | 14.26 |
| ATOM | 1322 | O   | ILE | 168 | 16.805 | 13.155 | 52.017 | 1.00 | 15.10 |
| ATOM | 1323 | N   | ASP | 169 | 17.823 | 12.772 | 53.913 | 1.00 | 15.41 |
| ATOM | 1324 | CA  | ASP | 169 | 16.631 | 12.138 | 54.507 | 1.00 | 16.46 |
| ATOM | 1325 | CB  | ASP | 169 | 17.078 | 11.500 | 55.840 | 1.00 | 16.03 |
| ATOM | 1326 | CG  | ASP | 169 | 15.931 | 10.619 | 56.316 | 1.00 | 17.04 |
| ATOM | 1327 | OD1 | ASP | 169 | 14.943 | 11.119 | 56.861 | 1.00 | 18.29 |
| ATOM | 1328 | OD2 | ASP | 169 | 16.030 | 9.434  | 55.962 | 1.00 | 17.14 |
| ATOM | 1329 | C   | ASP | 169 | 15.552 | 13.189 | 54.714 | 1.00 | 17.91 |
| ATOM | 1330 | O   | ASP | 169 | 15.803 | 14.268 | 55.270 | 1.00 | 16.68 |
| ATOM | 1331 | N   | LYS | 170 | 14.353 | 12.945 | 54.189 | 1.00 | 20.44 |
| ATOM | 1332 | CA  | LYS | 170 | 13.289 | 13.920 | 54.322 | 1.00 | 24.90 |
| ATOM | 1333 | CB  | LYS | 170 | 11.953 | 13.478 | 53.630 | 1.00 | 28.24 |
| ATOM | 1334 | CG  | LYS | 170 | 10.958 | 14.663 | 53.604 | 1.00 | 31.46 |
| ATOM | 1335 | CD  | LYS | 170 | 9.539  | 14.285 | 53.173 | 1.00 | 32.94 |
| ATOM | 1336 | CE  | LYS | 170 | 8.812  | 13.500 | 54.256 | 1.00 | 33.30 |
| ATOM | 1337 | NZ  | LYS | 170 | 7.402  | 13.165 | 53.899 | 1.00 | 34.02 |
| ATOM | 1338 | C   | LYS | 170 | 12.943 | 14.155 | 55.804 | 1.00 | 25.11 |
| ATOM | 1339 | O   | LYS | 170 | 12.858 | 15.277 | 56.264 | 1.00 | 26.53 |
| ATOM | 1340 | N   | ASP | 171 | 12.768 | 13.048 | 56.520 | 1.00 | 24.81 |
| ATOM | 1341 | CA  | ASP | 171 | 12.371 | 13.086 | 57.912 | 1.00 | 25.10 |
| ATOM | 1342 | CB  | ASP | 171 | 11.725 | 11.776 | 58.342 | 1.00 | 29.27 |
| ATOM | 1343 | CG  | ASP | 171 | 10.592 | 11.235 | 57.534 | 1.00 | 31.17 |
| ATOM | 1344 | OD1 | ASP | 171 | 9.713  | 11.934 | 57.004 | 1.00 | 31.40 |
| ATOM | 1345 | OD2 | ASP | 171 | 10.606 | 9.961  | 57.381 | 1.00 | 34.11 |
| ATOM | 1346 | C   | ASP | 171 | 13.414 | 13.491 | 58.919 | 1.00 | 23.57 |
| ATOM | 1347 | O   | ASP | 171 | 13.096 | 14.249 | 59.861 | 1.00 | 23.55 |
| ATOM | 1348 | N   | HIS | 172 | 14.650 | 13.038 | 58.756 | 1.00 | 21.67 |
| ATOM | 1349 | CA  | HIS | 172 | 15.718 | 13.379 | 59.697 | 1.00 | 19.37 |
| ATOM | 1350 | CB  | HIS | 172 | 16.113 | 12.098 | 60.464 | 1.00 | 21.26 |
| ATOM | 1351 | CG  | HIS | 172 | 14.941 | 11.559 | 61.215 | 1.00 | 23.69 |
| ATOM | 1352 | ND1 | HIS | 172 | 14.618 | 12.008 | 62.472 | 1.00 | 24.87 |
| ATOM | 1353 | CE1 | HIS | 172 | 13.515 | 11.392 | 62.882 | 1.00 | 26.42 |
| ATOM | 1354 | NE2 | HIS | 172 | 13.139 | 10.532 | 61.925 | 1.00 | 26.64 |
| ATOM | 1355 | CD2 | HIS | 172 | 14.026 | 10.625 | 60.873 | 1.00 | 25.35 |
| ATOM | 1356 | C   | HIS | 172 | 16.950 | 13.850 | 58.932 | 1.00 | 16.97 |
| ATOM | 1357 | O   | HIS | 172 | 17.981 | 13.177 | 58.955 | 1.00 | 16.83 |
| ATOM | 1358 | N   | PRO | 173 | 16.836 | 14.984 | 58.274 | 1.00 | 14.57 |
| ATOM | 1359 | CA  | PRO | 173 | 17.899 | 15.518 | 57.452 | 1.00 | 13.11 |
| ATOM | 1360 | CB  | PRO | 173 | 17.279 | 16.758 | 56.843 | 1.00 | 12.46 |
| ATOM | 1361 | CG  | PRO | 173 | 16.198 | 17.136 | 57.826 | 1.00 | 12.80 |
| ATOM | 1362 | CD  | PRO | 173 | 15.585 | 15.805 | 58.221 | 1.00 | 13.20 |
| ATOM | 1363 | C   | PRO | 173 | 19.199 | 15.766 | 58.159 | 1.00 | 13.01 |
| ATOM | 1364 | O   | PRO | 173 | 20.244 | 15.711 | 57.538 | 1.00 | 12.71 |
| ATOM | 1365 | N   | LEU | 174 | 19.213 | 16.071 | 59.457 | 1.00 | 13.35 |
| ATOM | 1366 | CA  | LEU | 174 | 20.415 | 16.341 | 60.183 | 1.00 | 13.25 |
| ATOM | 1367 | CB  | LEU | 174 | 20.352 | 17.642 | 60.973 | 1.00 | 14.23 |
| ATOM | 1368 | CG  | LEU | 174 | 20.025 | 18.898 | 60.156 | 1.00 | 13.91 |
| ATOM | 1369 | CD1 | LEU | 174 | 20.038 | 20.108 | 61.077 | 1.00 | 16.72 |
| ATOM | 1370 | CD2 | LEU | 174 | 20.967 | 19.113 | 58.996 | 1.00 | 15.55 |
| ATOM | 1371 | C   | LEU | 174 | 20.917 | 15.204 | 61.019 | 1.00 | 14.24 |
| ATOM | 1372 | O   | LEU | 174 | 21.890 | 15.390 | 61.748 | 1.00 | 14.10 |
| ATOM | 1373 | N   | GLN | 175 | 20.363 | 14.016 | 60.855 | 1.00 | 15.52 |
| ATOM | 1374 | CA  | GLN | 175 | 20.798 | 12.832 | 61.630 | 1.00 | 17.11 |
| ATOM | 1375 | CB  | GLN | 175 | 19.623 | 11.857 | 61.795 | 1.00 | 20.95 |

TABLE 1-continued

Structure Coordinates for S. aureus pdf

| ATOM | 1376 | CG | GLN | 175 | 19.941 | 10.655 | 62.677 | 1.00 | 27.18 |
|------|------|-----|-----|-----|--------|--------|--------|------|-------|
| ATOM | 1377 | CD | GLN | 175 | 18.877 | 9.585 | 62.700 | 1.00 | 31.22 |
| ATOM | 1378 | OE1 | GLN | 175 | 18.540 | 8.994 | 63.751 | 1.00 | 33.20 |
| ATOM | 1379 | NE2 | GLN | 175 | 18.330 | 9.235 | 61.533 | 1.00 | 33.65 |
| ATOM | 1380 | C | GLN | 175 | 21.922 | 12.122 | 60.898 | 1.00 | 16.99 |
| ATOM | 1381 | O | GLN | 175 | 21.713 | 11.588 | 59.798 | 1.00 | 16.15 |
| ATOM | 1382 | N | PRO | 176 | 23.104 | 12.137 | 61.448 | 1.00 | 17.92 |
| ATOM | 1383 | CA | PRO | 176 | 24.264 | 11.514 | 60.860 | 1.00 | 19.07 |
| ATOM | 1384 | CB | PRO | 176 | 25.425 | 11.958 | 61.729 | 1.00 | 18.77 |
| ATOM | 1385 | CG | PRO | 176 | 24.866 | 13.138 | 62.518 | 1.00 | 18.47 |
| ATOM | 1386 | CD | PRO | 176 | 23.452 | 12.771 | 62.748 | 1.00 | 17.86 |
| ATOM | 1387 | C | PRO | 176 | 24.188 | 9.990 | 60.900 | 1.00 | 20.17 |
| ATOM | 1388 | O | PRO | 176 | 23.732 | 9.400 | 61.895 | 1.00 | 20.92 |
| ATOM | 1389 | N | HIS | 177 | 24.619 | 9.352 | 59.807 | 1.00 | 19.53 |
| ATOM | 1390 | CA | HIS | 177 | 24.656 | 7.914 | 59.784 | 1.00 | 20.36 |
| ATOM | 1391 | CB | HIS | 177 | 24.919 | 7.206 | 58.469 | 1.00 | 18.20 |
| ATOM | 1392 | CG | HIS | 177 | 23.802 | 7.337 | 57.474 | 1.00 | 14.95 |
| ATOM | 1393 | ND1 | HIS | 177 | 24.005 | 7.159 | 56.138 | 1.00 | 16.40 |
| ATOM | 1394 | CE1 | HIS | 177 | 22.864 | 7.356 | 55.480 | 1.00 | 16.26 |
| ATOM | 1395 | NE2 | HIS | 177 | 21.958 | 7.707 | 56.368 | 1.00 | 16.00 |
| ATOM | 1396 | CD2 | HIS | 177 | 22.523 | 7.700 | 57.617 | 1.00 | 14.21 |
| ATOM | 1397 | C | HIS | 177 | 25.658 | 7.423 | 60.841 | 1.00 | 21.02 |
| ATOM | 1398 | O | HIS | 177 | 26.693 | 8.019 | 61.082 | 1.00 | 22.02 |
| ATOM | 1399 | N | THR | 178 | 25.255 | 6.325 | 61.480 | 1.00 | 22.22 |
| ATOM | 1400 | CA | THR | 178 | 26.106 | 5.744 | 62.510 | 1.00 | 23.81 |
| ATOM | 1401 | CB | THR | 178 | 25.412 | 4.447 | 63.017 | 1.00 | 26.92 |
| ATOM | 1402 | OG1 | THR | 178 | 24.070 | 4.779 | 63.455 | 1.00 | 28.11 |
| ATOM | 1403 | CG2 | THR | 178 | 26.218 | 3.926 | 64.192 | 1.00 | 27.70 |
| ATOM | 1404 | C | THR | 178 | 27.479 | 5.379 | 61.959 | 1.00 | 23.54 |
| ATOM | 1405 | O | THR | 178 | 27.595 | 4.594 | 61.005 | 1.00 | 25.27 |
| ATOM | 1406 | N | ASP | 179 | 28.540 | 5.880 | 62.536 | 1.00 | 22.85 |
| ATOM | 1407 | CA | ASP | 179 | 29.901 | 5.593 | 62.172 | 1.00 | 22.95 |
| ATOM | 1408 | CB | ASP | 179 | 30.170 | 4.097 | 62.080 | 1.00 | 28.84 |
| ATOM | 1409 | CG | ASP | 179 | 29.950 | 3.241 | 63.312 | 1.00 | 33.14 |
| ATOM | 1410 | OD1 | ASP | 179 | 29.420 | 2.094 | 63.173 | 1.00 | 34.35 |
| ATOM | 1411 | OD2 | ASP | 179 | 30.323 | 3.605 | 64.467 | 1.00 | 34.72 |
| ATOM | 1412 | C | ASP | 179 | 30.399 | 6.357 | 60.953 | 1.00 | 20.84 |
| ATOM | 1413 | O | ASP | 179 | 31.509 | 6.146 | 60.505 | 1.00 | 19.20 |
| ATOM | 1414 | N | ALA | 180 | 29.601 | 7.293 | 60.426 | 1.00 | 19.98 |
| ATOM | 1415 | CA | ALA | 180 | 30.052 | 8.106 | 59.279 | 1.00 | 18.45 |
| ATOM | 1416 | CB | ALA | 180 | 28.857 | 8.752 | 58.604 | 1.00 | 17.76 |
| ATOM | 1417 | C | ALA | 180 | 31.020 | 9.145 | 59.822 | 1.00 | 18.09 |
| ATOM | 1418 | O | ALA | 180 | 30.881 | 9.578 | 60.960 | 1.00 | 18.46 |
| ATOM | 1419 | N | VAL | 181 | 32.063 | 9.501 | 59.124 | 1.00 | 17.49 |
| ATOM | 1420 | CA | VAL | 181 | 33.062 | 10.462 | 59.459 | 1.00 | 17.25 |
| ATOM | 1421 | CB | VAL | 181 | 34.320 | 10.313 | 58.578 | 1.00 | 17.21 |
| ATOM | 1422 | CG1 | VAL | 181 | 35.301 | 11.466 | 58.792 | 1.00 | 17.56 |
| ATOM | 1423 | CG2 | VAL | 181 | 35.050 | 9.012 | 58.805 | 1.00 | 17.06 |
| ATOM | 1424 | C | VAL | 181 | 32.558 | 11.911 | 59.223 | 1.00 | 18.05 |
| ATOM | 1425 | O | VAL | 181 | 32.154 | 12.253 | 58.113 | 1.00 | 16.95 |
| ATOM | 1426 | N | GLU | 182 | 32.586 | 12.714 | 60.268 | 1.00 | 17.72 |
| ATOM | 1427 | CA | GLU | 182 | 32.200 | 14.126 | 60.126 | 1.00 | 18.58 |
| ATOM | 1428 | CB | GLU | 182 | 31.974 | 14.715 | 61.518 | 1.00 | 22.08 |
| ATOM | 1429 | CG | GLU | 182 | 31.570 | 16.170 | 61.478 | 1.00 | 26.15 |
| ATOM | 1430 | CD | GLU | 182 | 31.741 | 16.841 | 62.827 | 1.00 | 31.27 |
| ATOM | 1431 | OE1 | GLU | 182 | 32.208 | 16.207 | 63.810 | 1.00 | 32.77 |
| ATOM | 1432 | OE2 | GLU | 182 | 31.553 | 18.068 | 62.895 | 1.00 | 34.76 |
| ATOM | 1433 | C | GLU | 182 | 33.434 | 14.816 | 59.533 | 1.00 | 18.49 |
| ATOM | 1434 | O | GLU | 182 | 34.509 | 14.839 | 60.154 | 1.00 | 17.55 |
| ATOM | 1435 | N | VAL | 183 | 33.323 | 15.377 | 58.351 | 1.00 | 19.14 |
| ATOM | 1436 | CA | VAL | 183 | 34.454 | 16.036 | 57.698 | 1.00 | 20.41 |
| ATOM | 1437 | CB | VAL | 183 | 34.382 | 15.826 | 56.174 | 1.00 | 18.55 |
| ATOM | 1438 | CG1 | VAL | 183 | 35.474 | 16.547 | 55.414 | 1.00 | 17.81 |
| ATOM | 1439 | CG2 | VAL | 183 | 34.544 | 14.317 | 55.887 | 1.00 | 16.84 |
| ATOM | 1440 | C | VAL | 183 | 34.624 | 17.504 | 58.084 | 1.00 | 23.97 |
| ATOM | 1441 | O | VAL | 183 | 33.925 | 18.419 | 57.618 | 1.00 | 23.28 |
| ATOM | 1442 | N | HIS | 184 | 35.657 | 17.750 | 58.915 | 1.00 | 27.34 |
| ATOM | 1443 | CA | HIS | 184 | 36.010 | 19.078 | 59.381 | 1.00 | 30.88 |
| ATOM | 1444 | CB | HIS | 184 | 36.761 | 19.018 | 60.736 | 1.00 | 31.42 |
| ATOM | 1445 | CG | HIS | 184 | 35.950 | 18.462 | 61.852 | 1.00 | 33.04 |
| ATOM | 1446 | ND1 | HIS | 184 | 36.127 | 17.192 | 62.386 | 1.00 | 33.48 |
| ATOM | 1447 | CE1 | HIS | 184 | 35.239 | 16.983 | 63.324 | 1.00 | 33.63 |
| ATOM | 1448 | NE2 | HIS | 184 | 34.472 | 18.078 | 63.427 | 1.00 | 34.18 |
| ATOM | 1449 | CD2 | HIS | 184 | 34.885 | 19.009 | 62.505 | 1.00 | 33.72 |
| ATOM | 1450 | C | HIS | 184 | 36.944 | 19.774 | 58.398 | 1.00 | 33.03 |
| ATOM | 1451 | OXT | HIS | 184 | 38.145 | 19.370 | 58.369 | 1.00 | 34.40 |
| ATOM | 1452 | O | HIS | 184 | 36.482 | 20.674 | 57.663 | 1.00 | 34.98 |

TABLE 1-continued

Structure Coordinates for *S. aureus* pdf

| ATOM | 1453 | O | WAT | 185 | 28.850 | 21.236 | 41.157 | 1.00 | 7.77 |
|---|---|---|---|---|---|---|---|---|---|
| ATOM | 1454 | O | WAT | 186 | 31.430 | 6.491 | 39.145 | 1.00 | 5.36 |
| ATOM | 1455 | O | WAT | 187 | 31.972 | 20.433 | 24.682 | 1.00 | 19.06 |
| ATOM | 1456 | O | WAT | 188 | 43.418 | 17.395 | 32.297 | 1.00 | 7.22 |
| ATOM | 1457 | O | WAT | 189 | 29.795 | 9.718 | 43.035 | 1.00 | 13.01 |
| ATOM | 1458 | O | WAT | 190 | 25.169 | 14.868 | 44.564 | 1.00 | 7.63 |
| ATOM | 1459 | O | WAT | 191 | 42.565 | 13.342 | 49.566 | 1.00 | 12.53 |
| ATOM | 1460 | O | WAT | 192 | 23.545 | 16.936 | 36.967 | 1.00 | 11.47 |
| ATOM | 1461 | O | WAT | 193 | 38.976 | 27.793 | 26.907 | 1.00 | 19.75 |
| ATOM | 1462 | O | WAT | 194 | 35.953 | 1.677 | 55.506 | 1.00 | 8.03 |
| ATOM | 1463 | O | WAT | 195 | 45.203 | 4.786 | 35.591 | 1.00 | 19.10 |
| ATOM | 1464 | O | WAT | 196 | 40.702 | 22.372 | 37.469 | 1.00 | 5.65 |
| ATOM | 1465 | O | WAT | 197 | 18.244 | 27.128 | 33.934 | 1.00 | 9.55 |
| ATOM | 1466 | O | WAT | 198 | 43.230 | 2.407 | 45.385 | 1.00 | 14.44 |
| ATOM | 1467 | O | WAT | 199 | 28.760 | 15.753 | 52.327 | 1.00 | 6.36 |
| ATOM | 1468 | O | WAT | 200 | 39.314 | 16.273 | 54.340 | 1.00 | 10.38 |
| ATOM | 1469 | O | WAT | 201 | 41.628 | 6.864 | 49.085 | 1.00 | 13.25 |
| ATOM | 1470 | O | WAT | 202 | 32.628 | 8.643 | 33.259 | 1.00 | 14.96 |
| ATOM | 1471 | O | WAT | 203 | 23.608 | 15.684 | 31.276 | 1.00 | 11.92 |
| ATOM | 1472 | O | WAT | 204 | 41.619 | 27.241 | 32.862 | 1.00 | 12.62 |
| ATOM | 1473 | O | WAT | 205 | 25.455 | 16.379 | 42.062 | 1.00 | 9.79 |
| ATOM | 1474 | O | WAT | 206 | 23.458 | 25.587 | 46.689 | 1.00 | 9.28 |
| ATOM | 1475 | O | WAT | 207 | 40.092 | 2.673 | 49.703 | 1.00 | 21.98 |
| ATOM | 1476 | O | WAT | 208 | 35.495 | 30.435 | 31.702 | 1.00 | 9.21 |
| ATOM | 1477 | O | WAT | 209 | 40.520 | 4.464 | 47.917 | 1.00 | 17.40 |
| ATOM | 1478 | O | WAT | 210 | 28.201 | 9.930 | 46.793 | 1.00 | 14.09 |
| ATOM | 1479 | O | WAT | 211 | 23.089 | 19.943 | 52.306 | 1.00 | 14.82 |
| ATOM | 1480 | O | WAT | 212 | 44.399 | 21.289 | 35.915 | 1.00 | 13.38 |
| ATOM | 1481 | O | WAT | 213 | 38.302 | 11.682 | 56.310 | 1.00 | 13.86 |
| ATOM | 1482 | O | WAT | 214 | 29.194 | 31.320 | 26.877 | 1.00 | 14.92 |
| ATOM | 1483 | O | WAT | 215 | 41.034 | 0.350 | 43.151 | 1.00 | 8.79 |
| ATOM | 1484 | O | WAT | 216 | 37.315 | 5.552 | 55.980 | 1.00 | 15.69 |
| ATOM | 1485 | O | WAT | 217 | 28.681 | 5.735 | 37.072 | 1.00 | 27.33 |
| ATOM | 1486 | O | WAT | 218 | 27.519 | 26.142 | 27.532 | 1.00 | 20.83 |
| ATOM | 1487 | O | WAT | 220 | 26.523 | 16.871 | 54.153 | 1.00 | 7.21 |
| ATOM | 1488 | O | WAT | 221 | 26.631 | 8.829 | 40.556 | 1.00 | 13.85 |
| ATOM | 1489 | O | WAT | 222 | 42.195 | 14.491 | 24.181 | 1.00 | 18.25 |
| ATOM | 1490 | O | WAT | 223 | 39.484 | 2.299 | 47.684 | 1.00 | 17.37 |
| ATOM | 1491 | O | WAT | 224 | 42.696 | 5.852 | 33.808 | 1.00 | 21.32 |
| ATOM | 1492 | O | WAT | 225 | 21.738 | 21.298 | 24.368 | 1.00 | 34.50 |
| ATOM | 1493 | O | WAT | 226 | 22.987 | 10.820 | 52.989 | 1.00 | 14.83 |
| ATOM | 1494 | O | WAT | 227 | 46.793 | 19.037 | 41.919 | 1.00 | 17.41 |
| ATOM | 1495 | O | WAT | 228 | 50.134 | 12.914 | 25.200 | 1.00 | 13.49 |
| ATOM | 1496 | O | WAT | 229 | 34.941 | 32.358 | 33.918 | 1.00 | 10.04 |
| ATOM | 1497 | O | WAT | 230 | 29.840 | 4.973 | 57.907 | 1.00 | 13.19 |
| ATOM | 1498 | O | WAT | 231 | 41.476 | 32.535 | 41.932 | 1.00 | 16.82 |
| ATOM | 1499 | O | WAT | 233 | 47.577 | 10.560 | 24.957 | 1.00 | 14.85 |
| ATOM | 1500 | O | WAT | 234 | 31.423 | 7.923 | 35.851 | 1.00 | 18.25 |
| ATOM | 1501 | O | WAT | 235 | 24.429 | 27.131 | 29.298 | 1.00 | 20.86 |
| ATOM | 1502 | O | WAT | 236 | 45.316 | 2.958 | 43.842 | 1.00 | 16.57 |
| ATOM | 1503 | O | WAT | 237 | 46.300 | 14.369 | 48.285 | 1.00 | 15.62 |
| ATOM | 1504 | O | WAT | 238 | 22.551 | 21.212 | 56.437 | 1.00 | 20.75 |
| ATOM | 1505 | O | WAT | 240 | 42.496 | 7.817 | 57.030 | 1.00 | 36.21 |
| ATOM | 1506 | O | WAT | 241 | 29.753 | 7.840 | 45.086 | 1.00 | 20.48 |
| ATOM | 1507 | O | WAT | 242 | 44.157 | 18.020 | 35.284 | 1.00 | 15.10 |
| ATOM | 1508 | O | WAT | 243 | 32.571 | 28.209 | 41.063 | 1.00 | 26.82 |
| ATOM | 1509 | O | WAT | 244 | 29.928 | 3.636 | 51.745 | 1.00 | 17.99 |
| ATOM | 1510 | O | WAT | 245 | 17.606 | 26.422 | 41.913 | 1.00 | 14.25 |
| ATOM | 1511 | O | WAT | 246 | 20.589 | 12.991 | 55.488 | 1.00 | 19.81 |
| ATOM | 1512 | O | WAT | 247 | 39.341 | 29.548 | 29.158 | 1.00 | 18.35 |
| ATOM | 1513 | O | WAT | 248 | 17.156 | 16.295 | 61.445 | 1.00 | 12.69 |
| ATOM | 1514 | O | WAT | 249 | 24.354 | 14.243 | 33.242 | 1.00 | 12.22 |
| ATOM | 1515 | O | WAT | 250 | 32.830 | 14.766 | 20.087 | 1.00 | 25.25 |
| ATOM | 1516 | O | WAT | 251 | 16.815 | 19.536 | 36.675 | 1.00 | 15.62 |
| ATOM | 1517 | O | WAT | 252 | 28.441 | 34.415 | 30.350 | 1.00 | 14.51 |
| ATOM | 1518 | O | WAT | 253 | 26.031 | 8.747 | 44.300 | 1.00 | 20.25 |
| ATOM | 1519 | O | WAT | 254 | 43.077 | 16.183 | 18.629 | 1.00 | 31.67 |
| ATOM | 1520 | O | WAT | 256 | 33.197 | 19.064 | 19.853 | 1.00 | 24.22 |
| ATOM | 1521 | O | WAT | 257 | 30.278 | 20.250 | 16.867 | 1.00 | 42.28 |
| ATOM | 1522 | O | WAT | 258 | 20.798 | 17.479 | 26.186 | 1.00 | 29.53 |
| ATOM | 1523 | O | WAT | 259 | 35.416 | 13.350 | 21.607 | 1.00 | 22.56 |
| ATOM | 1524 | O | WAT | 260 | 35.637 | 44.109 | 41.691 | 1.00 | 21.90 |
| ATOM | 1525 | O | WAT | 261 | 24.100 | 18.625 | 43.187 | 1.00 | 8.00 |
| ATOM | 1526 | O | WAT | 263 | 22.843 | 12.530 | 27.491 | 1.00 | 22.94 |
| ATOM | 1527 | O | WAT | 264 | 44.179 | 24.395 | 43.693 | 1.00 | 23.48 |
| ATOM | 1528 | O | WAT | 265 | 18.860 | 10.472 | 42.233 | 1.00 | 22.82 |
| ATOM | 1529 | O | WAT | 266 | 16.026 | 26.688 | 39.851 | 1.00 | 14.46 |

TABLE 1-continued

Structure Coordinates for S. aureus pdf

| | | | | | | | | | |
|---|---|---|---|---|---|---|---|---|---|
| ATOM | 1530 | O | WAT | 267 | 26.345 | 14.750 | 24.426 | 1.00 | 23.54 |
| ATOM | 1531 | O | WAT | 268 | 37.901 | 14.303 | 60.873 | 1.00 | 57.94 |
| ATOM | 1532 | O | WAT | 269 | 23.911 | 8.885 | 51.213 | 1.00 | 19.17 |
| ATOM | 1533 | O | WAT | 270 | 25.088 | 18.293 | 25.334 | 1.00 | 21.16 |
| ATOM | 1534 | O | WAT | 271 | 32.345 | 12.423 | 22.061 | 1.00 | 26.85 |
| ATOM | 1535 | O | WAT | 272 | 29.849 | 8.405 | 23.646 | 1.00 | 22.55 |
| ATOM | 1536 | O | WAT | 273 | 38.933 | 19.380 | 16.508 | 1.00 | 29.99 |
| ATOM | 1537 | O | WAT | 274 | 28.930 | 6.191 | 30.272 | 1.00 | 30.24 |
| ATOM | 1538 | O | WAT | 277 | 51.699 | 18.896 | 51.858 | 1.00 | 26.44 |
| ATOM | 1539 | O | WAT | 278 | 26.732 | 24.016 | 51.882 | 1.00 | 20.15 |
| ATOM | 1540 | O | WAT | 280 | 35.901 | 30.991 | 27.045 | 1.00 | 31.15 |
| ATOM | 1541 | O | WAT | 281 | 34.878 | 34.657 | 45.573 | 1.00 | 23.59 |
| ATOM | 1542 | O | WAT | 282 | 22.582 | 24.196 | 49.931 | 1.00 | 17.52 |
| ATOM | 1543 | O | WAT | 283 | 25.665 | 18.480 | 61.477 | 1.00 | 22.72 |
| ATOM | 1544 | O | WAT | 285 | 16.617 | 23.741 | 53.679 | 1.00 | 22.92 |
| ATOM | 1545 | O | WAT | 286 | 27.425 | 5.238 | 57.616 | 1.00 | 28.57 |
| ATOM | 1546 | O | WAT | 287 | 24.194 | 17.156 | 62.543 | 1.00 | 22.92 |
| ATOM | 1547 | O | WAT | 288 | 43.605 | 13.871 | 55.205 | 1.00 | 47.34 |
| ATOM | 1548 | O | WAT | 289 | 14.252 | 10.820 | 52.850 | 1.00 | 28.43 |
| ATOM | 1549 | O | WAT | 291 | 29.445 | 0.878 | 44.981 | 1.00 | 19.69 |
| ATOM | 1550 | O | WAT | 292 | 33.986 | 13.974 | 64.333 | 1.00 | 37.04 |
| ATOM | 1551 | O | WAT | 293 | 41.717 | 34.544 | 35.754 | 1.00 | 26.74 |
| ATOM | 1552 | O | WAT | 294 | 44.822 | 15.305 | 22.321 | 1.00 | 16.03 |
| ATOM | 1553 | O | WAT | 295 | 36.295 | 31.861 | 47.655 | 1.00 | 26.65 |
| ATOM | 1554 | O | WAT | 296 | 42.599 | 28.766 | 43.606 | 1.00 | 26.10 |
| ATOM | 1555 | O | WAT | 297 | 39.805 | 5.761 | 18.396 | 1.00 | 41.39 |
| ATOM | 1556 | O | WAT | 298 | 13.973 | 17.827 | 35.310 | 1.00 | 54.73 |
| ATOM | 1557 | O | WAT | 299 | 27.996 | 7.316 | 26.790 | 1.00 | 18.08 |
| ATOM | 1558 | O | WAT | 300 | 42.886 | 21.511 | 50.516 | 1.00 | 18.76 |
| ATOM | 1559 | O | WAT | 303 | 49.197 | 25.130 | 46.385 | 1.00 | 34.63 |
| ATOM | 1560 | O | WAT | 304 | 30.514 | 20.096 | 22.934 | 1.00 | 26.25 |
| ATOM | 1561 | O | WAT | 305 | 16.070 | 11.629 | 32.114 | 1.00 | 33.09 |
| ATOM | 1562 | O | WAT | 307 | 45.009 | 9.505 | 49.911 | 1.00 | 38.13 |
| ATOM | 1563 | O | WAT | 308 | 19.596 | 10.468 | 29.457 | 1.00 | 17.29 |
| ATOM | 1564 | O | WAT | 309 | 15.205 | 14.450 | 44.995 | 1.00 | 14.06 |
| ATOM | 1565 | O | WAT | 310 | 29.356 | 16.954 | 20.232 | 1.00 | 31.55 |
| ATOM | 1566 | O | WAT | 311 | 24.108 | 38.264 | 35.844 | 1.00 | 39.11 |
| ATOM | 1567 | O | WAT | 312 | 35.407 | 6.361 | 25.290 | 1.00 | 30.83 |
| ATOM | 1568 | O | WAT | 313 | 39.712 | 31.481 | 26.164 | 1.00 | 59.55 |
| ATOM | 1569 | O | WAT | 314 | 46.008 | 26.765 | 46.643 | 1.00 | 24.46 |
| ATOM | 1570 | O | WAT | 315 | 31.206 | 32.756 | 27.472 | 1.00 | 25.26 |
| ATOM | 1571 | O | WAT | 316 | 50.563 | 22.574 | 47.365 | 1.00 | 33.15 |
| ATOM | 1572 | O | WAT | 317 | 44.191 | 6.963 | 54.611 | 1.00 | 37.60 |
| ATOM | 1573 | O | WAT | 318 | 25.966 | 3.136 | 59.271 | 1.00 | 35.51 |
| ATOM | 1574 | O | WAT | 319 | 37.521 | 28.687 | 19.179 | 1.00 | 42.82 |
| ATOM | 1575 | O | WAT | 320 | 37.860 | 6.732 | 23.019 | 1.00 | 29.39 |
| ATOM | 1576 | O | WAT | 321 | 16.404 | 30.148 | 38.616 | 1.00 | 44.90 |
| ATOM | 1577 | O | WAT | 322 | 20.948 | 10.666 | 55.483 | 1.00 | 20.70 |
| ATOM | 1578 | O | WAT | 323 | 42.010 | 40.095 | 40.065 | 1.00 | 30.74 |
| ATOM | 1579 | O | WAT | 324 | 34.974 | 43.535 | 31.498 | 1.00 | 33.73 |
| ATOM | 1580 | O | WAT | 325 | 36.339 | 21.393 | 17.438 | 1.00 | 22.90 |
| ATOM | 1581 | O | WAT | 326 | 22.573 | 26.604 | 27.035 | 1.00 | 25.45 |
| ATOM | 1582 | O | WAT | 327 | 43.925 | 1.275 | 33.700 | 1.00 | 31.52 |
| ATOM | 1583 | O | WAT | 328 | 44.055 | 25.497 | 31.799 | 1.00 | 25.75 |
| ATOM | 1584 | O | WAT | 329 | 21.385 | 6.303 | 61.996 | 1.00 | 33.54 |
| ATOM | 1585 | O | WAT | 330 | 29.459 | 11.771 | 63.481 | 1.00 | 30.61 |
| ATOM | 1586 | O | WAT | 331 | 44.458 | 29.701 | 35.168 | 1.00 | 21.73 |
| ATOM | 1587 | O | WAT | 332 | 44.874 | 3.401 | 28.884 | 1.00 | 21.60 |
| ATOM | 1588 | O | WAT | 333 | 35.791 | 46.126 | 38.798 | 1.00 | 31.81 |
| ATOM | 1589 | O | WAT | 335 | 42.315 | 35.196 | 45.915 | 1.00 | 81.46 |
| ATOM | 1590 | O | WAT | 336 | 31.457 | 36.447 | 45.501 | 1.00 | 48.90 |
| ATOM | 1591 | O | WAT | 337 | 21.963 | 8.289 | 49.003 | 1.00 | 25.78 |
| ATOM | 1592 | O | WAT | 338 | 46.389 | 28.795 | 37.209 | 1.00 | 25.28 |
| ATOM | 1593 | O | WAT | 339 | 24.612 | 30.116 | 24.354 | 1.00 | 52.56 |
| ATOM | 1594 | O | WAT | 340 | 32.083 | 2.650 | 30.885 | 1.00 | 67.46 |
| ATOM | 1595 | O | WAT | 341 | 44.830 | 28.999 | 40.931 | 1.00 | 47.88 |
| ATOM | 1596 | O | WAT | 342 | 30.337 | 12.782 | 23.955 | 1.00 | 18.21 |
| ATOM | 1597 | O | WAT | 343 | 28.938 | 3.896 | 35.075 | 1.00 | 33.18 |
| ATOM | 1598 | O | WAT | 344 | 14.617 | 18.243 | 39.459 | 1.00 | 29.61 |
| ATOM | 1599 | O | WAT | 345 | 24.634 | 22.916 | 24.622 | 1.00 | 27.73 |
| ATOM | 1600 | O | WAT | 346 | 39.434 | 34.582 | 32.483 | 1.00 | 20.28 |
| ATOM | 1601 | O | WAT | 347 | 12.161 | 23.144 | 40.518 | 1.00 | 61.26 |
| ATOM | 1602 | O | WAT | 348 | 27.481 | 2.007 | 50.279 | 1.00 | 79.56 |
| ATOM | 1603 | O | WAT | 349 | 42.979 | 34.755 | 39.897 | 1.00 | 44.74 |
| ATOM | 1604 | O | WAT | 350 | 28.778 | 41.078 | 42.112 | 1.00 | 28.20 |
| ATOM | 1605 | O | WAT | 351 | 17.300 | 10.548 | 37.874 | 1.00 | 43.80 |
| ATOM | 1606 | O | WAT | 352 | 19.099 | 8.296 | 59.238 | 1.00 | 40.38 |

TABLE 1-continued

Structure Coordinates for S. aureus pdf

| ATOM | 1607 | O | WAT | 353 | 27.220 | 31.276 | 48.083 | 1.00 | 40.23 |
|---|---|---|---|---|---|---|---|---|---|
| ATOM | 1608 | O | WAT | 354 | 25.981 | 34.775 | 41.644 | 1.00 | 40.74 |
| ATOM | 1609 | O | WAT | 355 | 27.143 | 6.951 | 48.473 | 1.00 | 25.01 |
| ATOM | 1610 | O | WAT | 356 | 38.151 | 11.528 | 18.954 | 1.00 | 25.07 |
| ATOM | 1611 | O | WAT | 357 | 19.762 | 7.319 | 56.021 | 1.00 | 25.55 |
| ATOM | 1612 | O | WAT | 358 | 28.144 | 1.582 | 55.375 | 1.00 | 89.67 |
| ATOM | 1613 | O | WAT | 360 | 27.638 | 16.644 | 62.799 | 1.00 | 23.18 |
| ATOM | 1614 | O | WAT | 361 | 14.684 | 31.678 | 44.174 | 1.00 | 71.66 |
| ATOM | 1615 | O | WAT | 362 | 15.650 | 11.558 | 66.663 | 1.00 | 64.23 |
| ATOM | 1616 | O | WAT | 363 | 15.237 | 18.359 | 54.178 | 1.00 | 39.41 |
| ATOM | 1617 | O | WAT | 364 | 43.172 | 16.847 | 51.474 | 1.00 | 22.97 |
| ATOM | 1618 | O | WAT | 365 | 18.986 | 26.729 | 27.844 | 1.00 | 48.99 |
| ATOM | 1619 | O | WAT | 366 | 27.139 | 19.402 | 23.399 | 1.00 | 29.96 |
| ATOM | 1620 | O | WAT | 367 | 45.600 | 0.114 | 38.791 | 1.00 | 74.35 |
| ATOM | 1621 | O | WAT | 369 | 19.987 | 11.960 | 57.958 | 1.00 | 16.62 |
| ATOM | 1622 | O | WAT | 372 | 27.335 | 27.231 | 54.352 | 1.00 | 40.25 |
| ATOM | 1623 | O | WAT | 373 | 15.884 | 15.171 | 31.990 | 1.00 | 16.33 |
| ATOM | 1624 | O | WAT | 374 | 15.330 | 24.772 | 50.039 | 1.00 | 32.03 |
| ATOM | 1625 | O | WAT | 377 | 43.724 | 3.843 | 52.380 | 1.00 | 65.10 |
| ATOM | 1626 | O | WAT | 378 | 38.825 | 38.327 | 52.464 | 1.00 | 49.54 |
| ATOM | 1627 | O | WAT | 379 | 46.669 | 23.629 | 33.133 | 1.00 | 28.01 |
| ATOM | 1628 | O | WAT | 380 | 25.700 | 12.197 | 66.584 | 1.00 | 89.69 |
| ATOM | 1629 | O | WAT | 381 | 16.946 | 9.817 | 50.702 | 1.00 | 39.01 |
| ATOM | 1630 | O | WAT | 382 | 28.300 | 9.517 | 63.491 | 1.00 | 33.60 |
| ATOM | 1631 | O | WAT | 384 | 46.564 | 10.837 | 53.832 | 1.00 | 46.92 |
| ATOM | 1632 | O | WAT | 385 | 19.884 | 8.624 | 51.494 | 1.00 | 27.80 |
| ATOM | 1633 | O | WAT | 387 | 40.902 | 2.984 | 29.363 | 1.00 | 31.27 |
| ATOM | 1634 | O | WAT | 391 | 34.316 | 2.463 | 62.378 | 1.00 | 58.47 |
| ATOM | 1635 | O | WAT | 392 | 33.435 | 11.543 | 52.204 | 1.00 | 30.98 |
| ATOM | 1636 | O | WAT | 393 | 31.770 | 25.813 | 26.248 | 1.00 | 27.06 |
| ATOM | 1637 | O | WAT | 400 | 29.567 | 21.566 | 48.768 | 1.00 | 15.75 |
| ATOM | 1638 | O | WAT | 402 | 48.664 | 8.376 | 47.162 | 1.00 | 18.07 |
| ATOM | 1639 | O | WAT | 403 | 27.502 | 36.401 | 36.418 | 1.00 | 21.54 |
| ATOM | 1640 | O | WAT | 404 | 38.545 | 3.037 | 55.400 | 1.00 | 13.22 |
| ATOM | 1641 | O | WAT | 405 | 31.109 | 23.890 | 44.564 | 1.00 | 12.95 |
| ATOM | 1642 | O | WAT | 406 | 37.990 | 6.814 | 28.956 | 1.00 | 20.51 |
| ATOM | 1643 | O | WAT | 407 | 23.258 | 29.488 | 41.877 | 1.00 | 11.41 |
| ATOM | 1644 | O | WAT | 409 | 38.433 | 6.626 | 31.944 | 1.00 | 19.15 |
| ATOM | 1645 | O | WAT | 410 | 31.295 | 21.118 | 43.998 | 1.00 | 14.11 |
| ATOM | 1646 | O | WAT | 411 | 29.526 | 7.658 | 41.193 | 1.00 | 14.42 |
| ATOM | 1647 | O | WAT | 412 | 47.253 | 15.532 | 34.182 | 1.00 | 15.59 |
| ATOM | 1648 | O | WAT | 413 | 32.025 | 22.355 | 49.225 | 1.00 | 22.54 |
| ATOM | 1649 | O | WAT | 414 | 35.003 | 0.189 | 57.857 | 1.00 | 17.18 |
| ATOM | 1650 | O | WAT | 415 | 38.803 | 38.578 | 33.800 | 1.00 | 50.11 |
| ATOM | 1651 | O | WAT | 416 | 31.617 | 3.615 | 39.556 | 1.00 | 15.08 |
| ATOM | 1652 | O | WAT | 417 | 41.233 | 19.520 | 51.473 | 1.00 | 26.94 |
| ATOM | 1653 | O | WAT | 418 | 34.336 | 27.496 | 25.242 | 1.00 | 32.64 |
| ATOM | 1654 | O | WAT | 419 | 31.486 | 2.145 | 58.952 | 1.00 | 26.96 |
| ATOM | 1655 | O | WAT | 420 | 20.483 | 8.464 | 45.003 | 1.00 | 39.84 |
| ATOM | 1656 | O | WAT | 421 | 38.402 | 6.719 | 60.710 | 1.00 | 53.78 |
| ATOM | 1657 | O | WAT | 422 | 17.225 | 14.988 | 64.662 | 1.00 | 27.63 |
| ATOM | 1658 | O | WAT | 423 | 29.858 | 4.786 | 43.647 | 1.00 | 25.15 |
| ATOM | 1659 | O | WAT | 424 | 30.773 | 22.384 | 54.282 | 1.00 | 36.55 |
| ATOM | 1660 | O | WAT | 425 | 38.526 | 14.414 | 56.721 | 1.00 | 20.85 |
| ATOM | 1661 | O | WAT | 426 | 30.456 | 20.512 | 46.952 | 1.00 | 19.94 |
| ATOM | 1662 | O | WAT | 427 | 22.093 | 34.199 | 38.603 | 1.00 | 30.42 |
| ATOM | 1663 | O | WAT | 428 | 29.003 | 23.510 | 42.193 | 1.00 | 14.64 |
| ATOM | 1664 | O | WAT | 430 | 24.931 | 30.471 | 52.337 | 1.00 | 30.16 |
| ATOM | 1665 | O | WAT | 431 | 48.705 | 28.493 | 42.035 | 1.00 | 55.68 |
| ATOM | 1666 | O | WAT | 432 | 39.117 | 4.219 | 32.847 | 1.00 | 25.71 |
| ATOM | 1667 | O | WAT | 433 | 26.609 | 27.683 | 58.327 | 1.00 | 27.50 |
| ATOM | 1668 | O | WAT | 434 | 39.186 | −0.478 | 36.174 | 1.00 | 49.55 |
| ATOM | 1669 | O | WAT | 435 | 41.271 | 4.828 | 21.864 | 1.00 | 39.72 |
| ATOM | 1670 | O | WAT | 436 | 41.092 | 33.182 | 29.047 | 1.00 | 32.94 |
| ATOM | 1671 | O | WAT | 437 | 15.296 | 21.832 | 45.786 | 1.00 | 40.79 |
| ATOM | 1672 | O | WAT | 438 | 28.338 | 42.926 | 45.181 | 1.00 | 54.46 |
| ATOM | 1673 | O | WAT | 439 | 18.910 | 32.039 | 47.096 | 1.00 | 34.92 |
| ATOM | 1674 | O | WAT | 440 | 20.737 | 30.240 | 33.890 | 1.00 | 27.30 |
| ATOM | 1675 | O | WAT | 441 | 39.566 | 2.311 | 52.603 | 1.00 | 9.84 |
| ATOM | 1676 | O | WAT | 442 | 26.307 | 7.449 | 29.241 | 1.00 | 24.87 |
| ATOM | 1677 | O | WAT | 443 | 33.345 | 6.388 | 32.193 | 1.00 | 25.75 |
| ATOM | 1678 | O | WAT | 444 | 31.294 | 5.444 | 34.030 | 1.00 | 30.09 |
| ATOM | 1679 | O | WAT | 445 | 28.477 | 5.556 | 33.091 | 1.00 | 33.90 |
| ATOM | 1680 | O | WAT | 446 | 35.818 | 5.354 | 27.499 | 1.00 | 34.01 |
| ATOM | 1681 | O | WAT | 447 | 38.643 | 6.449 | 25.935 | 1.00 | 36.56 |
| ATOM | 1682 | O | WAT | 448 | 32.925 | 5.503 | 23.694 | 1.00 | 34.87 |
| ATOM | 1683 | O | WAT | 449 | 36.725 | 28.997 | 25.274 | 1.00 | 30.86 |

TABLE 1-continued

Structure Coordinates for *S. aureus* pdf

| ATOM | 1684 | O | WAT | 450 | 33.363 | 29.455 | 26.675 | 1.00 | 37.40 |
|---|---|---|---|---|---|---|---|---|---|
| ATOM | 1685 | O | WAT | 451 | 41.451 | 27.420 | 25.703 | 1.00 | 33.62 |
| ATOM | 1686 | O | WAT | 452 | 29.410 | 26.542 | 26.305 | 1.00 | 29.99 |
| ATOM | 1687 | O | WAT | 453 | 36.755 | 35.395 | 27.932 | 1.00 | 31.87 |
| ATOM | 1688 | O | WAT | 454 | 38.358 | 33.650 | 29.807 | 1.00 | 27.03 |
| ATOM | 1689 | O | WAT | 455 | 37.465 | 31.045 | 29.786 | 1.00 | 24.00 |
| ATOM | 1690 | O | WAT | 456 | 36.203 | 38.857 | 29.055 | 1.00 | 33.74 |
| ATOM | 1691 | O | WAT | 457 | 43.139 | 26.818 | 23.216 | 1.00 | 42.86 |
| ATOM | 1692 | O | WAT | 458 | 44.010 | 27.925 | 26.702 | 1.00 | 35.47 |
| ATOM | 1693 | O | WAT | 459 | 42.654 | 24.489 | 23.829 | 1.00 | 36.86 |
| ATOM | 1694 | O | WAT | 460 | 41.901 | 30.150 | 29.907 | 1.00 | 28.79 |
| ATOM | 1695 | O | WAT | 461 | 26.772 | 28.402 | 27.845 | 1.00 | 24.54 |
| ATOM | 1696 | O | WAT | 462 | 26.549 | 25.016 | 24.992 | 1.00 | 30.41 |
| ATOM | 1697 | O | WAT | 463 | 24.198 | 25.675 | 25.291 | 1.00 | 29.34 |
| ATOM | 1698 | O | WAT | 464 | 18.389 | 23.209 | 26.099 | 1.00 | 27.72 |
| ATOM | 1699 | O | WAT | 465 | 15.792 | 17.751 | 27.506 | 1.00 | 35.38 |
| ATOM | 1700 | O | WAT | 466 | 18.177 | 19.068 | 27.187 | 1.00 | 29.61 |
| ATOM | 1701 | O | WAT | 467 | 20.277 | 34.110 | 40.402 | 1.00 | 39.33 |
| ATOM | 1702 | O | WAT | 468 | 22.420 | 34.685 | 35.945 | 1.00 | 32.47 |
| ATOM | 1703 | O | WAT | 469 | 25.586 | 36.936 | 38.120 | 1.00 | 30.14 |
| ATOM | 1704 | O | WAT | 470 | 22.975 | 32.962 | 41.300 | 1.00 | 37.30 |
| ATOM | 1705 | O | WAT | 471 | 22.668 | 19.271 | 25.898 | 1.00 | 29.84 |
| ATOM | 1706 | O | WAT | 472 | 18.891 | 9.006 | 33.972 | 1.00 | 36.50 |
| ATOM | 1707 | O | WAT | 473 | 24.180 | 8.334 | 27.833 | 1.00 | 29.82 |
| ATOM | 1708 | O | WAT | 474 | 26.583 | 4.932 | 30.103 | 1.00 | 31.47 |
| ATOM | 1709 | O | WAT | 475 | 35.276 | 12.918 | 19.062 | 1.00 | 29.07 |
| ATOM | 1710 | O | WAT | 476 | 37.941 | 14.051 | 18.038 | 1.00 | 30.43 |
| ATOM | 1711 | O | WAT | 477 | 38.446 | 16.323 | 16.217 | 1.00 | 33.99 |
| ATOM | 1712 | O | WAT | 478 | 38.163 | 8.369 | 18.377 | 1.00 | 28.75 |
| ATOM | 1713 | O | WAT | 479 | 42.854 | 7.090 | 21.196 | 1.00 | 35.78 |
| ATOM | 1714 | O | WAT | 480 | 43.719 | 8.314 | 25.189 | 1.00 | 18.37 |
| ATOM | 1715 | O | WAT | 481 | 44.810 | 8.599 | 19.951 | 1.00 | 33.64 |
| ATOM | 1716 | O | WAT | 482 | 47.966 | 7.671 | 21.852 | 1.00 | 31.71 |
| ATOM | 1717 | O | WAT | 483 | 45.820 | 13.136 | 19.737 | 1.00 | 32.03 |
| ATOM | 1718 | O | WAT | 484 | 31.751 | 17.094 | 18.635 | 1.00 | 30.24 |
| ATOM | 1719 | O | WAT | 485 | 27.993 | 14.973 | 20.979 | 1.00 | 33.51 |
| ATOM | 1720 | O | WAT | 486 | 26.220 | 11.398 | 22.499 | 1.00 | 33.95 |
| ATOM | 1721 | O | WAT | 487 | 28.510 | 14.814 | 17.996 | 1.00 | 35.70 |
| ATOM | 1722 | O | WAT | 488 | 33.549 | 20.609 | 17.456 | 1.00 | 30.90 |
| ATOM | 1723 | O | WAT | 489 | 27.960 | 13.392 | 23.087 | 1.00 | 26.06 |
| ATOM | 1724 | O | WAT | 490 | 40.175 | 20.917 | 14.980 | 1.00 | 37.89 |
| ATOM | 1725 | ZN | Zn | 500 | 26.949 | 20.605 | 41.894 | 1.00 | 12.48 |
| END | | | | | | | | | |

What is claimed is:

1. A crystal of *S. aureus* peptide deformylase of SEQ ID NO: 12 having the orthorhombic space group symmetry $C222_1$ and comprising a unit cell having dimensions a, b, and c; wherein a is about 90 Å to about 100 Å, b is about 116 Å to about 128 Å, and c is about 45 Å to about 50 Å; and wherein $\alpha=\beta=\gamma=90°$.

2. A crystal of *S. aureus* peptide deformylase of SEQ ID NO: 12 having the space group symmetry C2 and comprising a unit cell having dimensions a, b, and c; wherein a is about 85 Å to about 100 Å, b is about 35 Å to about 50 Å, and c is about 90 Å to about 110 Å; and wherein $\alpha=\gamma=90°$ and $\beta$ is about 90° to about 95°.

3. A crystal of *S. aureus* peptide deformylase of SEQ ID NO: 12 having the tetragonal space group symmetry $P4_1$ or $P4_22_12$ and comprising a unit cell having dimensions a, b, and c; wherein a and b are about 130 Å to about 190 Å, and c is about 30 Å to about 70 Å; and wherein $\alpha=\beta=\gamma=90°$.

* * * * *

SEQUENCE LISTING

<160> NUMBER OF SEQ ID NOS: 12

<210> SEQ ID NO 1
<211> LENGTH: 213
<212> TYPE: PRT
<213> ORGANISM: Staphylococcus aureus

<400> SEQUENCE: 1

```
Met Tyr Glu Tyr Leu Asn Asn Leu Phe Thr Val Ile Gln Leu Lys Gln
1               5                   10                  15

Ile Lys Ile Arg Lys Val Gln Tyr Met Leu Thr Met Lys Asp Ile Ile
            20                  25                  30

Arg Asp Gly His Pro Thr Leu Arg Gln Lys Ala Ala Glu Leu Glu Leu
        35                  40                  45

Pro Leu Thr Lys Glu Glu Lys Glu Thr Leu Ile Ala Met Arg Glu Phe
    50                  55                  60

Leu Val Asn Ser Gln Asp Glu Glu Ile Ala Lys Arg Tyr Gly Leu Arg
65                  70                  75                  80

Ser Gly Val Gly Leu Ala Ala Pro Gln Ile Asn Ile Ser Lys Arg Met
```

```
                    85                  90                  95
Ile Ala Val Leu Ile Pro Asp Asp Gly Ser Gly Lys Ser Tyr Asp Tyr
            100                 105                 110

Met Leu Val Asn Pro Lys Ile Val Ser His Ser Val Gln Glu Ala Tyr
            115                 120                 125

Leu Pro Thr Gly Glu Gly Cys Leu Ser Val Asp Asp Asn Val Ala Gly
    130                 135                 140

Leu Val His Arg His Asn Lys Ile Thr Ile Lys Ala Lys Asp Ile Glu
145                 150                 155                 160

Gly Asn Asp Ile Gln Leu Arg Leu Lys Gly Tyr Pro Ala Ile Val Phe
                165                 170                 175

Gln His Glu Ile Asp His Leu Asn Gly Val Met Phe Tyr Asp His Ile
            180                 185                 190

Asp Lys Asp His Pro Leu Gln Pro His Thr Asp Ala Val Glu Val His
            195                 200                 205

Gln His His His His
    210

<210> SEQ ID NO 2
<211> LENGTH: 168
<212> TYPE: PRT
<213> ORGANISM: Escherichia coli

<400> SEQUENCE: 2

Ser Val Leu Gln Val Leu His Ile Pro Asp Glu Arg Leu Arg Lys Val
1               5                   10                  15

Ala Lys Pro Val Glu Glu Val Asn Ala Glu Ile Gln Arg Ile Val Asp
            20                  25                  30

Asp Met Phe Glu Thr Met Tyr Ala Glu Glu Gly Ile Gly Leu Ala Ala
        35                  40                  45

Thr Gln Val Asp Ile His Gln Arg Ile Ile Val Ile Asp Val Ser Glu
    50                  55                  60

Asn Arg Asp Glu Arg Leu Val Leu Ile Asn Pro Glu Leu Leu Glu Lys
65                  70                  75                  80

Ser Gly Glu Thr Gly Ile Glu Gly Cys Leu Ser Ile Pro Glu Gln
                85                  90                  95

Arg Ala Leu Val Pro Arg Ala Glu Lys Val Lys Ile Arg Ala Leu Asp
            100                 105                 110

Arg Asp Gly Lys Pro Phe Glu Leu Glu Ala Asp Gly Leu Leu Ala Ile
            115                 120                 125

Cys Ile Gln His Glu Met Asp His Leu Val Gly Lys Leu Phe Met Asp
    130                 135                 140

Tyr Leu Ser Pro Leu Lys Gln Gln Arg Ile Arg Gln Lys Val Glu Lys
145                 150                 155                 160

Leu Asp Arg Leu Lys Ala Arg Ala
                165

<210> SEQ ID NO 3
<211> LENGTH: 169
<212> TYPE: PRT
<213> ORGANISM: Haemophilus influenzae

<400> SEQUENCE: 3

Met Thr Ala Leu Asn Val Leu Ile Tyr Pro Asp Asp His Leu Lys Val
1               5                   10                  15

Val Cys Glu Pro Val Thr Lys Val Asn Asp Ala Ile Arg Lys Ile Val
```

```
                20                  25                  30

Asp Asp Met Phe Asp Thr Met Tyr Gln Glu Lys Gly Ile Gly Leu Ala
            35                  40                  45

Ala Pro Gln Val Asp Ile Leu Gln Arg Ile Ile Thr Ile Asp Val Glu
        50                  55                  60

Gly Asp Lys Gln Asn Gln Phe Val Leu Ile Asn Pro Glu Ile Leu Ala
 65                  70                  75                  80

Ser Glu Gly Glu Thr Gly Ile Glu Gly Cys Leu Ser Ile Pro Gly
                85                  90                  95

Phe Arg Ala Leu Val Pro Arg Lys Glu Lys Val Thr Val Arg Ala Leu
            100                 105                 110

Asp Arg Asp Gly Lys Glu Phe Thr Leu Asp Ala Asp Gly Leu Leu Ala
            115                 120                 125

Ile Cys Ile Gln His Glu Ile Asp His Leu Asn Gly Ile Leu Phe Val
            130                 135                 140

Asp Tyr Leu Ser Pro Leu Lys Arg Gln Arg Ile Lys Glu Lys Leu Ile
145                 150                 155                 160

Lys Tyr Lys Lys Gln Ile Ala Lys Ser
                165

<210> SEQ ID NO 4
<211> LENGTH: 160
<212> TYPE: PRT
<213> ORGANISM: Bacillus subtilis

<400> SEQUENCE: 4

Met Ala Val Lys Lys Val Val Thr His Pro Ala Glu Val Leu Glu Thr
1               5                   10                  15

Pro Ala Glu Thr Val Thr Val Phe Asp Lys Lys Leu Lys Lys Leu Leu
            20                  25                  30

Asp Asp Met Tyr Asp Thr Met Leu Glu Met Asp Gly Val Gly Leu Ala
            35                  40                  45

Ala Pro Gln Ile Gly Ile Leu Lys Arg Ala Ala Val Val Glu Ile Gly
        50                  55                  60

Asp Asp Arg Gly Arg Ile Asp Leu Val Asn Pro Glu Ile Leu Glu Lys
65                  70                  75                  80

Ser Gly Glu Gln Thr Gly Ile Glu Gly Cys Leu Ser Phe Pro Asn Val
                85                  90                  95

Tyr Gly Asp Val Thr Arg Ala Asp Tyr Val Lys Val Arg Ala Phe Asn
            100                 105                 110

Arg Gln Gly Lys Pro Phe Ile Leu Glu Ala Arg Gly Phe Leu Ala Arg
            115                 120                 125

Ala Val Gln His Glu Met Asp His Leu Asp Gly Val Leu Phe Thr Ser
            130                 135                 140

Lys Ile Ser Lys Tyr Tyr Thr Glu Asp Glu Leu Ala Asp Met Glu Gly
145                 150                 155                 160

<210> SEQ ID NO 5
<211> LENGTH: 216
<212> TYPE: PRT
<213> ORGANISM: Mycoplasma pneumoniae

<400> SEQUENCE: 5

Met Thr Lys Ile Leu Pro Val Ser Thr Ile Ser Ile Phe Arg Ile Ile
1               5                   10                  15

Leu Ile Leu Pro Gln Ile Asn Met Glu Leu Leu Pro Thr Lys Ala Trp
```

```
                    20                  25                  30
Leu Val Leu Asp Asp Val Lys Glu Ile Asn Glu Pro Thr Lys Pro Val
                35                  40                  45

Gln Phe Pro Leu Asp Gln Ala Ser Leu Asp Cys Ile Ala Lys Met Met
         50                  55                  60

Ala Tyr Val Asp Ala Ser Tyr Asn Gly Asp Ala Glu Lys Tyr Gly Ile
65                  70                  75                  80

Ile Pro Gly Ile Gly Ile Ala Ala Asn Gln Ile Gly Tyr Trp Lys Gln
                    85                  90                  95

Met Phe Tyr Ile His Leu Met Asp Gly Gly Val Glu His Lys Cys Leu
                100                 105                 110

Leu Ile Asn Pro Lys Ile Ile Asn Leu Ser Ala Asn Lys Ser Phe Leu
            115                 120                 125

Lys Ser Gly Glu Gly Cys Leu Ser Val Pro Lys Met His Gln Gly Tyr
        130                 135                 140

Val Ile Arg His Glu Trp Ile Thr Ile Thr Gly Phe Asp Trp Leu Gln
145                 150                 155                 160

Gln Lys Glu Ile Thr Ile Thr Ala Thr Gly Leu Phe Gly Met Cys Leu
                    165                 170                 175

Gln His Glu Phe Asp His Leu Gln Gly Arg Phe Tyr Tyr His Arg Ile
                180                 185                 190

Asn Pro Leu Asn Pro Leu Phe Thr Asn Lys Glu Trp Lys Val Ile Asn
            195                 200                 205

Pro Ala Leu Pro Ser Asp Ser Glu
        210                 215

<210> SEQ ID NO 6
<211> LENGTH: 170
<212> TYPE: PRT
<213> ORGANISM: Staphylococcus aureus

<400> SEQUENCE: 6

Met Ala Ile Lys Lys Leu Val Pro Ala Ser His Pro Ile Leu Thr Lys
1               5                   10                  15

Lys Ala Gln Ala Val Lys Thr Phe Asp Asp Ser Leu Lys Arg Leu Leu
                20                  25                  30

Gln Asp Leu Glu Asp Thr Met Tyr Ala Gln Ala Ala Gly Leu Cys
         35                  40                  45

Ala Pro Gln Ile Asn Gln Ser Leu Gln Val Ala Ile Asp Met Glu
        50                  55                  60

Met Glu Gly Leu Leu Gln Leu Val Asn Pro Lys Ile Ile Ser Gln Ser
65                  70                  75                  80

Asn Glu Thr Ile Thr Asp Leu Glu Gly Ser Ile Thr Leu Pro Asp Val
                85                  90                  95

Tyr Gly Glu Val Thr Arg Ser Lys Met Ile Val Val Glu Ser Tyr Asp
                100                 105                 110

Val Asn Gly Asn Lys Val Glu Leu Thr Ala His Glu Asp Val Ala Arg
            115                 120                 125

Met Ile Leu His Ile Ile Asp Gln Met Asn Gly Ile Pro Phe Thr Glu
        130                 135                 140

Arg Ala Asp Arg Ile Leu Thr Asp Lys Glu Val Glu Ala Tyr Phe Ile
145                 150                 155                 160

Asn Asp Arg Ser His His His His His His
                165                 170
```

<210> SEQ ID NO 7
<211> LENGTH: 172
<212> TYPE: PRT
<213> ORGANISM: Staphylococcus aureus

<400> SEQUENCE: 7

```
Met Leu Thr Met Lys Asp Ile Ile Arg Asp Gly His Leu Arg Gln Lys
1               5                   10                  15
Ala Ala Glu Ile Glu Leu Pro Leu Thr Glu Lys Glu Thr Leu Ile
            20                  25                  30
Met Arg Glu Phe Leu Val Asn Ser Gln Asp Glu Ile Ala Lys Arg
        35                  40                  45
Tyr Gly Gly Val Gly Leu Ala Ala Pro Gln Ile Asn Ile Ser Lys Arg
    50                  55                  60
Met Ile Ala Val Leu Ile Pro Asp Asp Gly Ser Gly Lys Ser Tyr Asp
65                  70                  75                  80
Leu Val Asn Pro Lys Ile Val Ser Ser Val Gln Glu Ala Tyr Leu Pro
                85                  90                  95
Thr Glu Gly Cys Leu Val Asp Asp Asn Val Ala Leu Val His Arg His
            100                 105                 110
Asn Arg Ile Ile Lys Ala Lys Asp Ile Glu Gly Asn Asp Ile Gln Leu
        115                 120                 125
Arg Leu Lys Gly Tyr Pro Ala Ile Val Phe Gln His Glu Ile Asp His
    130                 135                 140
Ile Asn Gly Val Met Phe Tyr Asp His Ile Asp Lys Asp His Pro Leu
145                 150                 155                 160
Gln Pro His Thr Asp Ala Val Glu Val His His His
                165                 170
```

<210> SEQ ID NO 8
<211> LENGTH: 138
<212> TYPE: PRT
<213> ORGANISM: Escherichia coli

<400> SEQUENCE: 8

```
Ser Val Leu Arg Lys Val Ala Lys Pro Val Glu Val Glu Ile Gln
1               5                   10                  15
Arg Ile Val Asp Met Phe Glu Thr Met Tyr Gly Ile Gly Leu Ala Ala
            20                  25                  30
Thr Gln Val Asp Ile His Gln Arg Ile Ile Val Ile Asp Val Ser Glu
        35                  40                  45
Asn Leu Ile Asn Pro Glu Leu Leu Glu Ser Gly Glu Thr Gly Ile Glu
    50                  55                  60
Gly Cys Leu Ile Pro Glu Gln Arg Leu Val Pro Arg Ala Glu Lys Val
65                  70                  75                  80
Ile Arg Ala Leu Asp Arg Asp Gly Lys Pro Phe Glu Leu Glu Ala Asp
                85                  90                  95
Gly Leu Ile Ala Ile Cys Ile Gln His Glu Met Asp His Leu Val Gly
            100                 105                 110
Lys Leu Phe Met Asp Tyr Leu Ser Pro Leu Lys Gln Gln Arg Ile Arg
        115                 120                 125
Gln Lys Val Glu Lys Leu Asp Arg Leu Lys
    130                 135
```

<210> SEQ ID NO 9
<211> LENGTH: 6

-continued

```
<212> TYPE: PRT
<213> ORGANISM: Artificial
<220> FEATURE:
<223> OTHER INFORMATION: Amino Acid Residue
<220> FEATURE:
<221> NAME/KEY: MISC_FEATURE
<222> LOCATION: (2)..(2)
<223> OTHER INFORMATION: Any Amino Acid

<400> SEQUENCE: 9

Gly Xaa Gly Leu Ala Ala
1               5

<210> SEQ ID NO 10
<211> LENGTH: 5
<212> TYPE: PRT
<213> ORGANISM: Artificial
<220> FEATURE:
<223> OTHER INFORMATION: Amino Acid Residue

<400> SEQUENCE: 10

Glu Gly Cys Leu Ser
1               5

<210> SEQ ID NO 11
<211> LENGTH: 10
<212> TYPE: PRT
<213> ORGANISM: Artificial
<220> FEATURE:
<223> OTHER INFORMATION: Amino Acid Residue
<220> FEATURE:
<221> NAME/KEY: MISC_FEATURE
<222> LOCATION: (2)..(3)
<223> OTHER INFORMATION: Any Amino Acid
<220> FEATURE:
<221> NAME/KEY: MISC_FEATURE
<222> LOCATION: (7)..(7)
<223> OTHER INFORMATION: Any Amino Acid

<400> SEQUENCE: 11

Ile Xaa Xaa Gln His Glu Xaa Asp His Leu
1               5                   10

<210> SEQ ID NO 12
<211> LENGTH: 189
<212> TYPE: PRT
<213> ORGANISM: Staphylococcus aureus

<400> SEQUENCE: 12

Met Leu Thr Met Lys Asp Ile Ile Arg Asp Gly His Pro Thr Leu Arg
1               5                   10                  15

Gln Lys Ala Ala Glu Leu Glu Leu Pro Leu Thr Lys Glu Glu Lys Glu
            20                  25                  30

Thr Leu Ile Ala Met Arg Glu Phe Leu Val Asn Ser Gln Asp Glu Glu
        35                  40                  45

Ile Ala Lys Arg Tyr Gly Leu Arg Ser Gly Val Gly Leu Ala Ala Pro
    50                  55                  60

Gln Ile Asn Ile Ser Lys Arg Met Ile Ala Val Leu Ile Pro Asp Asp
65                  70                  75                  80

Gly Ser Gly Lys Ser Tyr Asp Tyr Met Leu Val Asn Pro Lys Ile Val
                85                  90                  95

Ser His Ser Val Gln Glu Ala Tyr Leu Pro Thr Gly Glu Gly Cys Leu
            100                 105                 110

Ser Val Asp Asp Asn Val Ala Gly Leu Val His Arg His Asn Lys Ile
        115                 120                 125
```

-continued

```
Thr Ile Lys Ala Lys Asp Ile Glu Gly Asn Asp Ile Gln Leu Arg Leu
    130             135             140

Lys Gly Tyr Pro Ala Ile Val Phe Gln His Glu Ile Asp His Leu Asn
145             150             155             160

Gly Val Met Phe Tyr Asp His Ile Asp Lys Asp His Pro Leu Gln Pro
                165             170             175

His Thr Asp Ala Val Glu Val His Gln His His His His
            180             185
```